US009176152B2

(12) United States Patent
Knutson et al.

(10) Patent No.: US 9,176,152 B2
(45) Date of Patent: Nov. 3, 2015

(54) METHODS AND APPARATUSES FOR DETECTION OF POSITIONAL FREEDOM OF PARTICLES IN BIOLOGICAL AND CHEMICAL ANALYSES AND APPLICATIONS IN IMMUNODIAGNOSTICS

(75) Inventors: Christopher Knutson, Woodridge, IL (US); Osman Akcakir, Plainville, MA (US); Haojun Fu, Naperville, IL (US)

(73) Assignee: Arryx, INC, Chicago, IL (US)

( * ) Notice: Subject to any disclaimer, the term of this patent is extended or adjusted under 35 U.S.C. 154(b) by 150 days.

(21) Appl. No.: 13/699,519

(22) PCT Filed: May 25, 2011

(86) PCT No.: PCT/US2011/000930
§ 371 (c)(1),
(2), (4) Date: Jul. 2, 2013

(87) PCT Pub. No.: WO2011/149526
PCT Pub. Date: Dec. 1, 2011

(65) Prior Publication Data
US 2013/0274119 A1     Oct. 17, 2013

Related U.S. Application Data

(60) Provisional application No. 61/348,072, filed on May 25, 2010, provisional application No. 61/347,946, filed on May 25, 2010.

(51) Int. Cl.
*G01N 33/80* (2006.01)
*G01N 33/50* (2006.01)
(Continued)

(52) U.S. Cl.
CPC ............ *G01N 33/80* (2013.01); *G01N 15/0211* (2013.01); *G01N 15/1463* (2013.01);
(Continued)

(58) Field of Classification Search
CPC ..... G01N 33/80; G01N 33/5029; G01N 33/53; G01N 33/543; G01N 15/0211; C40B 30/04
USPC ................... 435/7.1, 7.2, 7.21; 506/9; 356/39
See application file for complete search history.

(56) References Cited

U.S. PATENT DOCUMENTS
4,647,544 A    3/1987  Nicoli et al.
4,799,796 A    1/1989  Musha
(Continued)

FOREIGN PATENT DOCUMENTS
JP     2010-503866     2/2010
WO     02/37109 A2     5/2002
(Continued)

OTHER PUBLICATIONS
International Search Report (ISR), issued by the International Searching Authority on Dec. 23, 2011, in connection with International Application No. PCT/US11/00930.
(Continued)

*Primary Examiner* — Samuel Woolwine
*Assistant Examiner* — Kaijiang Zhang
(74) *Attorney, Agent, or Firm* — Jean C. Edwards, Esq.; Edwards Neils PLLC

(57) ABSTRACT

The present invention relates to methods and apparatuses for the detection of positional freedom of particles used in biological, biochemical, physical, biophysical, and chemical analyses. In particular, the present invention relates to methods and apparatuses which can detect and characterize a population of particles/cells based upon their detected mobility. In one embodiment consistent with the invention, detection of certain cells is based on differences detected in populations of cells that bind to a substrate and those that exhibit weaker binding forces. Initially, cells are settled on the substrate, and in the presence of gravitational, natural thermodynamic pressure fluctuations, and other random or applied forces, some of the particles may exhibit translational movement. Particle movement is detected, and measurements are computed, according to the methods and apparatuses of the present invention, to determine the binding of specific analytes.

49 Claims, 41 Drawing Sheets

(51) Int. Cl.
  *G01N 33/53*   (2006.01)
  *G01N 33/543*  (2006.01)
  *C40B 30/04*   (2006.01)
  *G01N 15/02*   (2006.01)
  *G01N 15/14*   (2006.01)
  *G06F 19/10*   (2011.01)
  *G01N 21/45*   (2006.01)

(52) U.S. Cl.
  CPC ...... *G01N33/5029* (2013.01); *G01N 33/54313* (2013.01); *G06F 19/10* (2013.01); *C40B 30/04* (2013.01); *G01N 21/453* (2013.01); *G01N 33/53* (2013.01); *G01N 2015/0216* (2013.01); *G01N 2015/1497* (2013.01)

(56) References Cited

U.S. PATENT DOCUMENTS

| | | | |
|---|---|---|---|
| 4,900,685 A | 2/1990 | Smith, III |
| 5,017,009 A | 5/1991 | Schutt et al. |
| 5,286,452 A | 2/1994 | Hansen |
| 5,532,814 A | 7/1996 | Cha |
| 5,589,401 A | 12/1996 | Hansen et al. |
| 5,599,668 A | 2/1997 | Stimpson et al. |
| 5,688,262 A | 11/1997 | Abraham |
| 5,707,799 A | 1/1998 | Hansmann et al. |
| 5,783,814 A | 7/1998 | Fairley et al. |
| 5,837,551 A | 11/1998 | Ekins |
| 6,075,558 A | 6/2000 | Tachibana et al. |
| 6,159,749 A | 12/2000 | Liu |
| 6,251,615 B1 | 6/2001 | Oberhardt |
| 6,310,687 B1 | 10/2001 | Stumbo et al. |
| 6,361,956 B1 | 3/2002 | Hänninen et al. |
| 6,368,553 B1 | 4/2002 | Lee |
| 6,406,848 B1 | 6/2002 | Bridgham et al. |
| 6,586,193 B2 | 7/2003 | Yguerabide et al. |
| 6,610,256 B2 | 8/2003 | Schwartz |
| 6,740,497 B2 | 5/2004 | Allbritton et al. |
| 6,770,488 B1 | 8/2004 | Carron et al. |
| 6,876,474 B2 | 4/2005 | Kreuzer et al. |
| 6,917,884 B2 | 7/2005 | Sammak et al. |
| 6,943,924 B2 | 9/2005 | Marquet et al. |
| 6,953,550 B2 | 10/2005 | Sheppard, Jr. et al. |
| 6,955,923 B2 | 10/2005 | Hartting |
| 6,961,481 B2 | 11/2005 | Lee et al. |
| 6,969,488 B2 | 11/2005 | Bridgham et al. |
| 6,979,574 B1 | 12/2005 | Kötitz et al. |
| 7,002,691 B2 | 2/2006 | Thomas et al. |
| 7,033,821 B2 | 4/2006 | Kim et al. |
| 7,042,639 B1 | 5/2006 | McDowell |
| 7,095,032 B2 | 8/2006 | Montagu et al. |
| 7,109,459 B2 | 9/2006 | Kam et al. |
| 7,122,384 B2 | 10/2006 | Prober et al. |
| 7,195,909 B2 | 3/2007 | Klenerman et al. |
| 7,221,490 B2 | 5/2007 | Coppola et al. |
| 7,255,995 B2 | 8/2007 | Yguerabide et al. |
| 7,268,939 B1 | 9/2007 | McDowell |
| 7,282,370 B2 | 10/2007 | Bridgham et al. |
| 7,301,133 B2 | 11/2007 | Weiss |
| 7,307,652 B2 | 12/2007 | Broemmelsiek |
| 7,312,090 B2 | 12/2007 | Lin et al. |
| 7,362,449 B2 | 4/2008 | Dubois et al. |
| 7,436,981 B2 | 10/2008 | Pace |
| 7,447,334 B1 | 11/2008 | Jiang et al. |
| 7,457,472 B2 | 11/2008 | Pace et al. |
| 7,460,240 B2 | 12/2008 | Akcakir |
| 7,463,366 B2 | 12/2008 | Dubois et al. |
| 7,498,551 B2 | 3/2009 | Werner et al. |
| 7,518,651 B2 | 4/2009 | Butterworth |
| 7,522,749 B2 | 4/2009 | Zitnick, III et al. |
| 7,532,214 B2 | 5/2009 | Lundström |
| 7,532,808 B2 | 5/2009 | Lainema |
| 7,542,588 B2 | 6/2009 | Ekin et al. |
| 7,547,554 B2 | 6/2009 | Odefey |
| 2002/0009723 A1 | 1/2002 | Hefti |
| 2002/0028471 A1 | 3/2002 | Oberhardt |
| 2003/0040607 A1 | 2/2003 | Sackstein |
| 2005/0098717 A1 | 5/2005 | Grier et al. |
| 2005/0239210 A1 | 10/2005 | Iida |
| 2007/0298433 A1 | 12/2007 | Sia et al. |
| 2008/0210869 A1 | 9/2008 | Gerritsen et al. |
| 2008/0250881 A1 | 10/2008 | Dona |
| 2009/0068671 A1 | 3/2009 | Chakrabarty |
| 2009/0290156 A1 | 11/2009 | Popescu et al. |
| 2011/0043607 A1 | 2/2011 | Grier et al. |

FOREIGN PATENT DOCUMENTS

| | | |
|---|---|---|
| WO | WO-02/087792 A1 | 11/2002 |
| WO | WO 2007/073345 A1 | 6/2007 |
| WO | WO 2008/034102 A2 | 3/2008 |
| WO | WO 2008034102 A2 * | 3/2008 |
| WO | WO 2009/059008 A1 | 5/2009 |
| WO | WO-2011/149525 A1 | 12/2011 |

OTHER PUBLICATIONS

Notice of Reasons for Rejection issued by the Japanese Patent Office on Jan. 20, 2015 in connection with Japanese Patent Application No. 2013-512599.

Notice of Reasons for Rejection issued by Japanese Patent Office on Mar. 17, 2015 in connection with Japanese Patent Application No. 2013-512598.

ISR and Written Opinion of the International Searching Authority issued on Aug. 26, 2011 in connection with International Application No. PCT/US2011/000929.

* cited by examiner

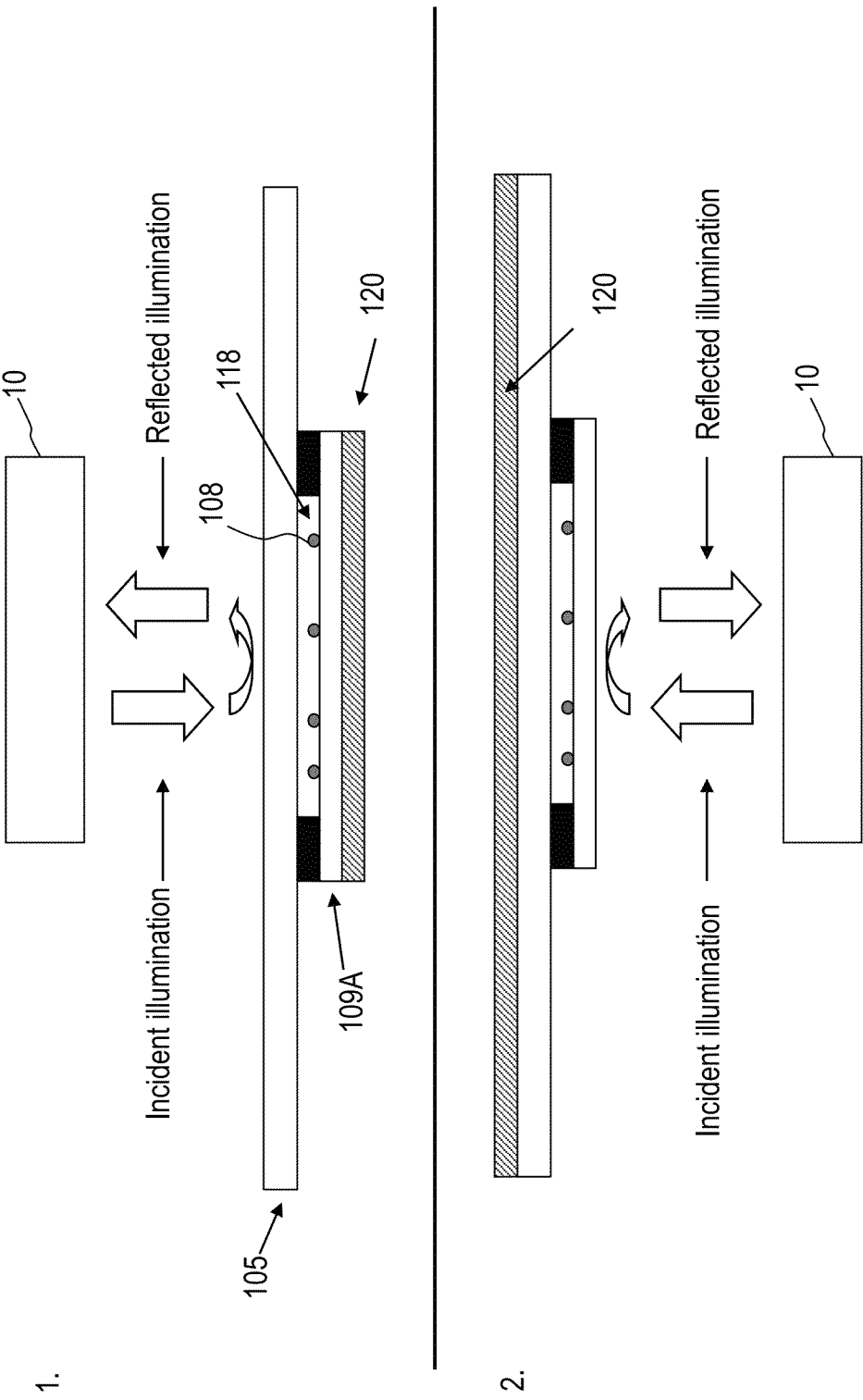

FIG. 1F
A.
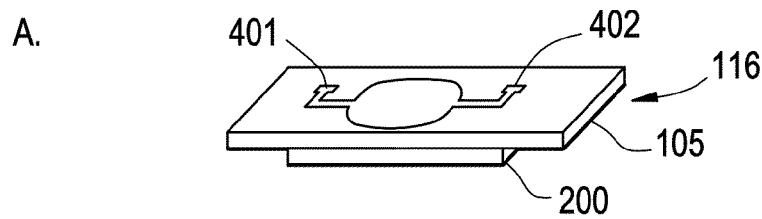
B.
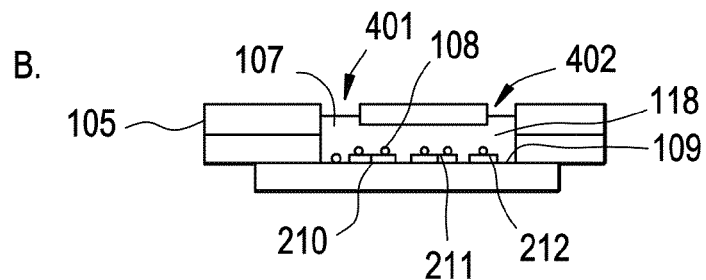
C.
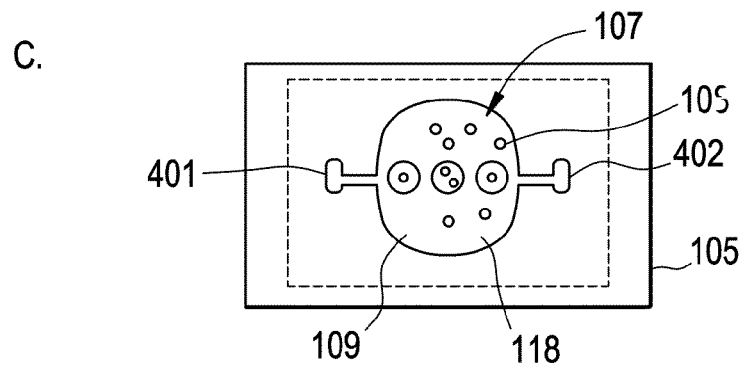
D.
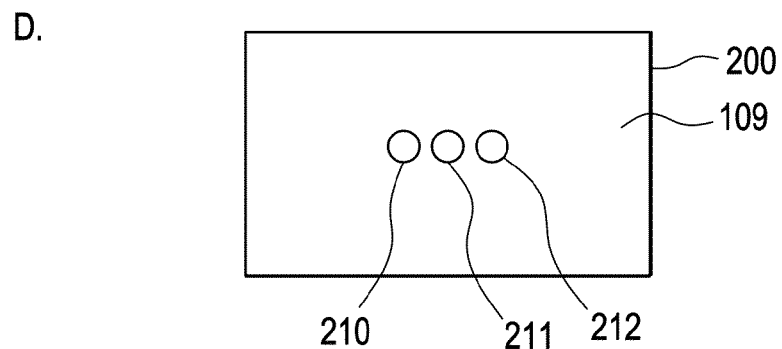

FIG. 1G
A.
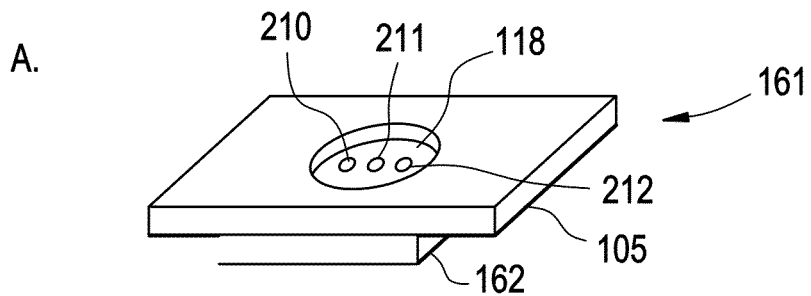
B.
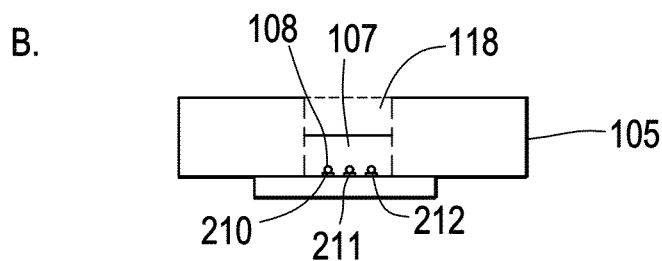
C.
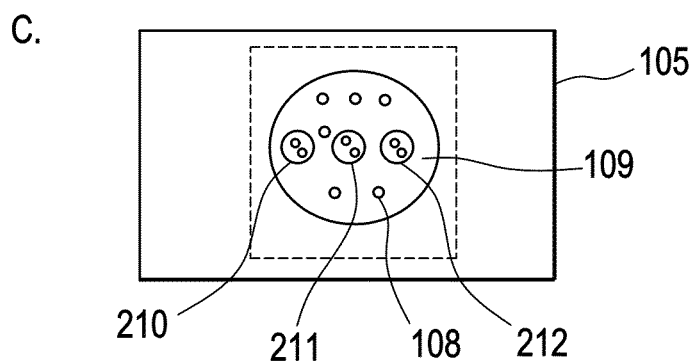

FIG. 1H
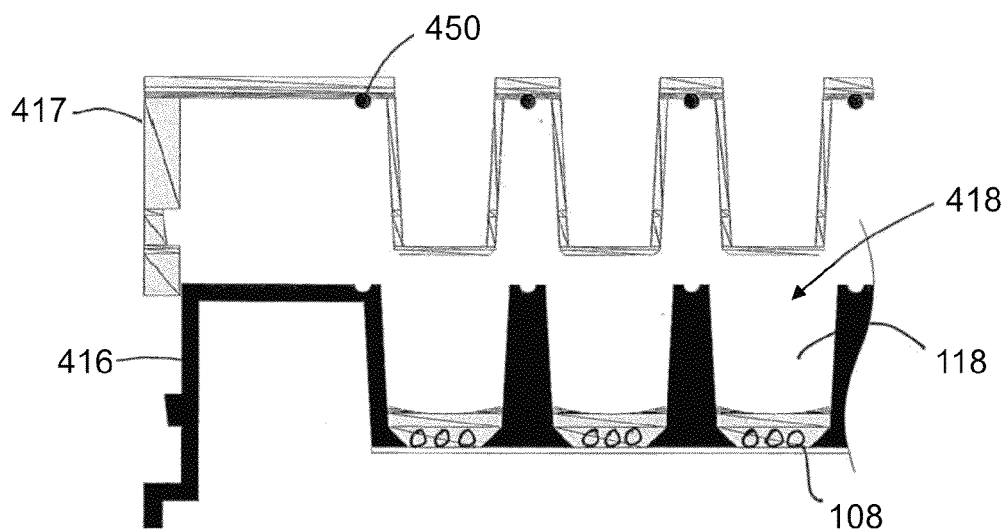
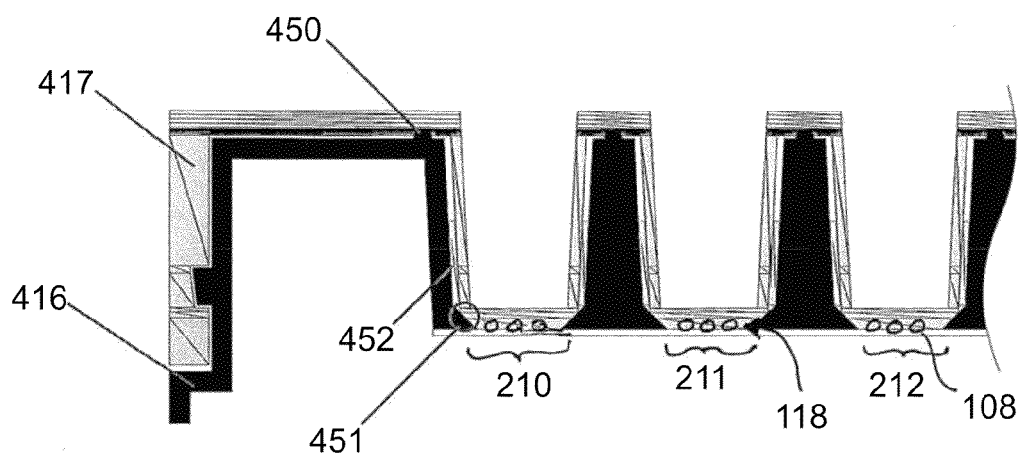
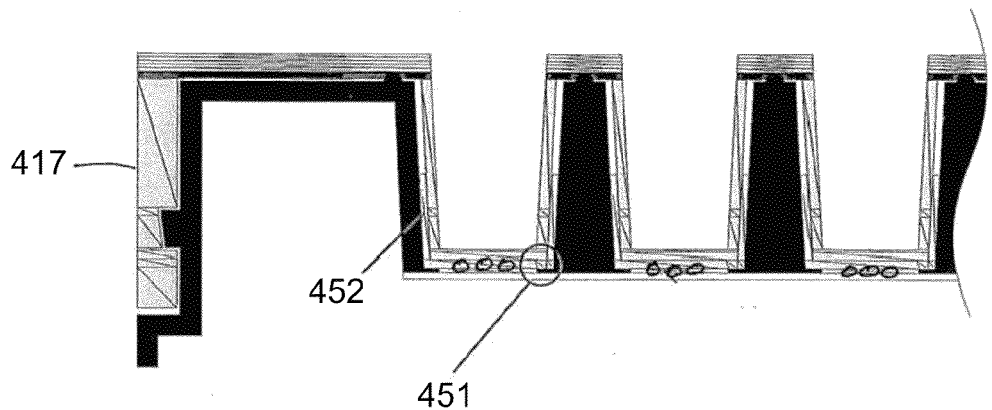

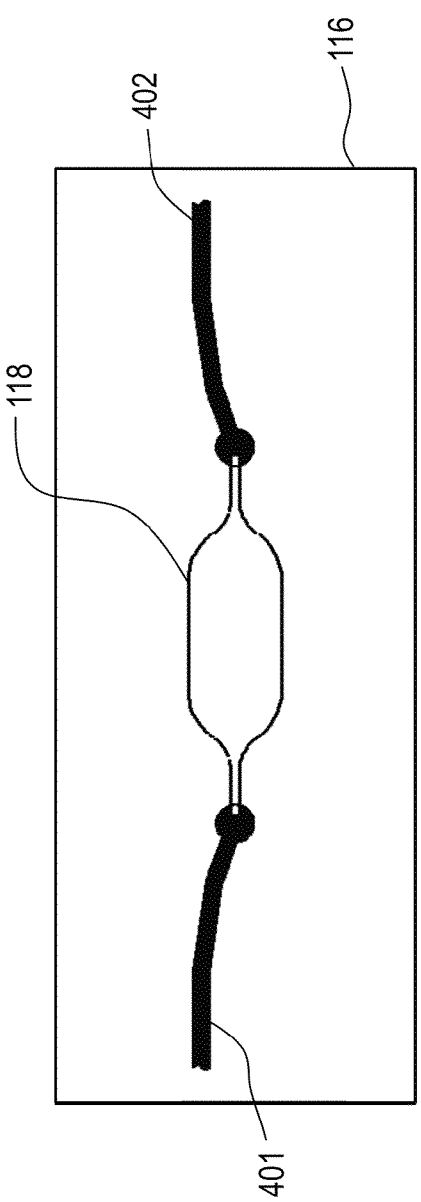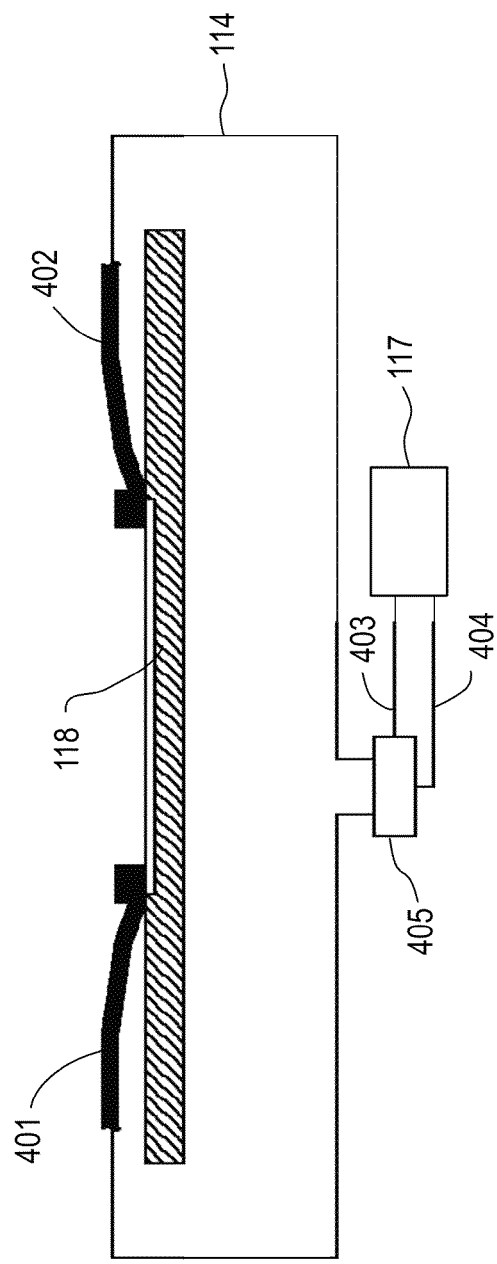
FIG. 2A

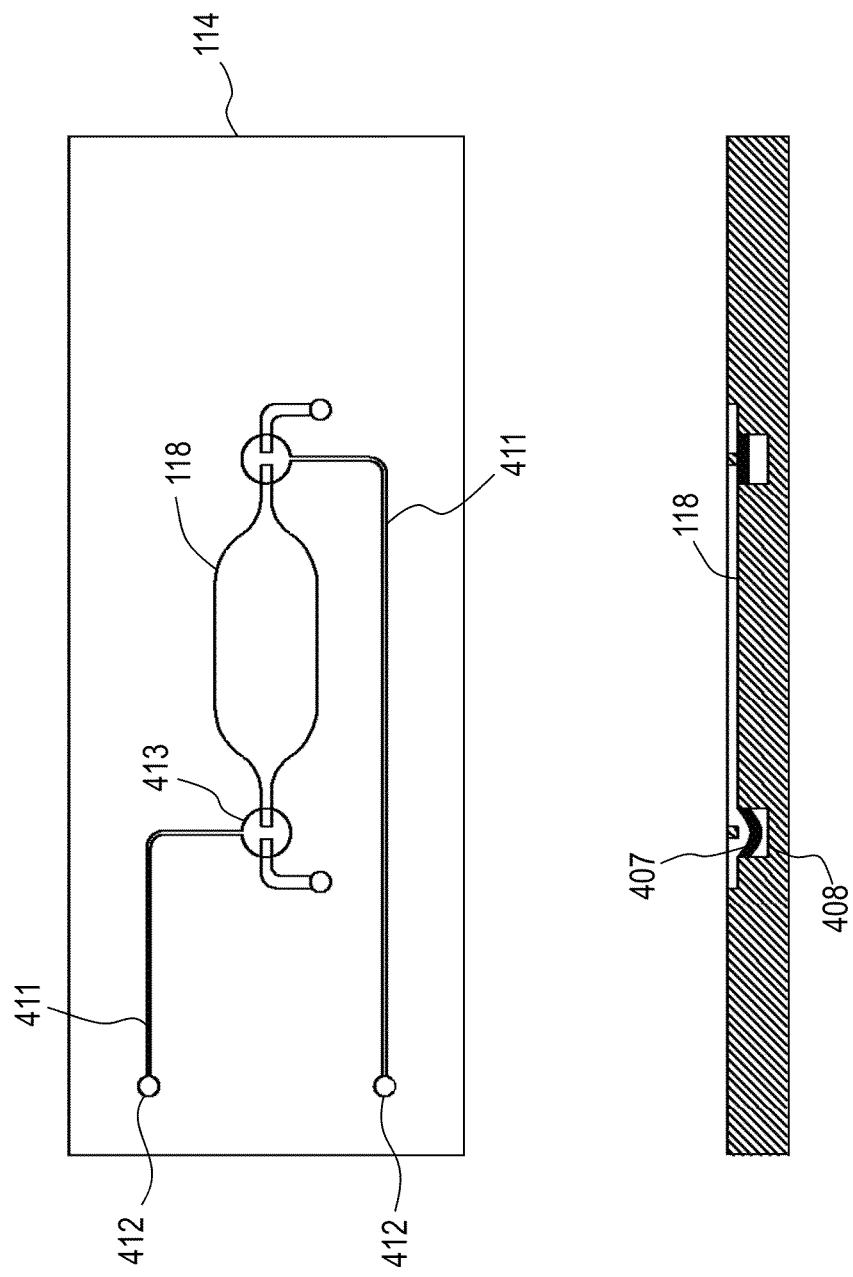

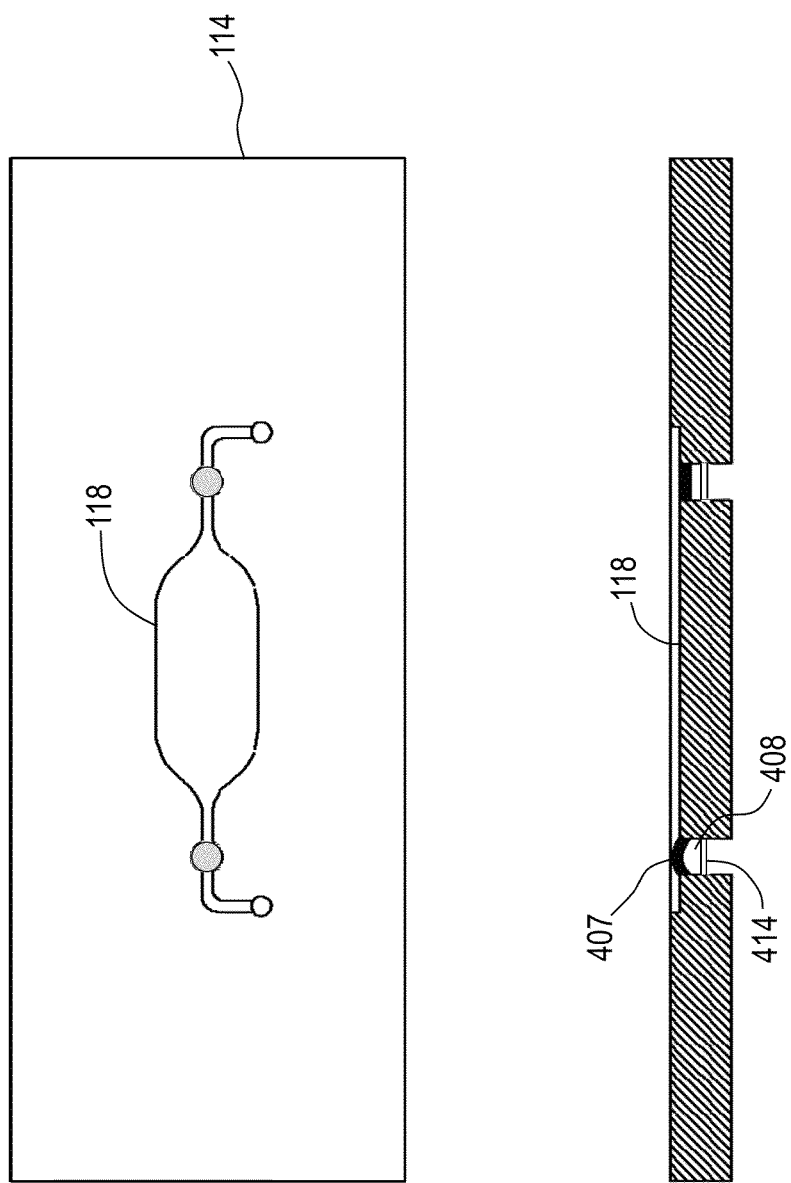

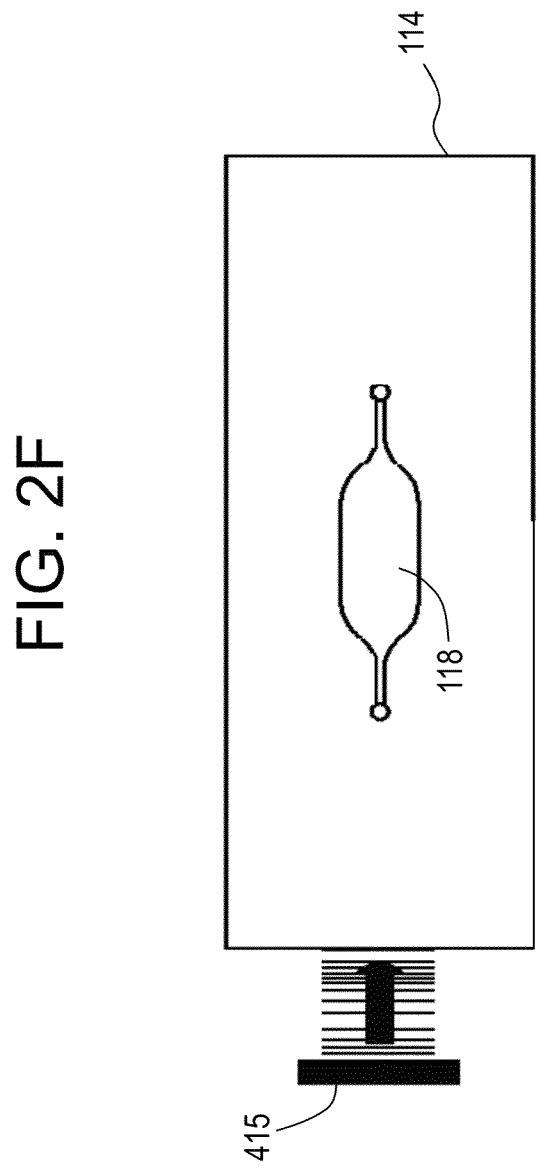

FIG. 2G
A.
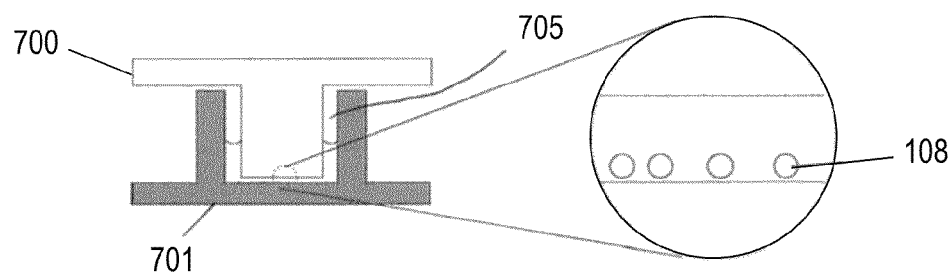
B.
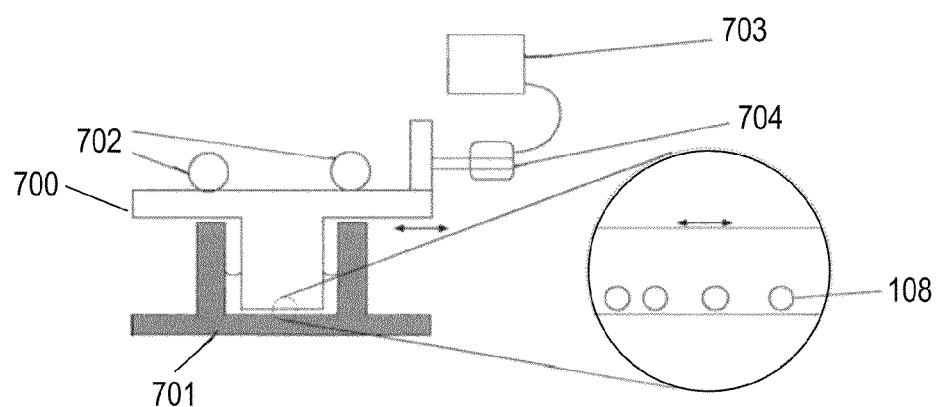
C.
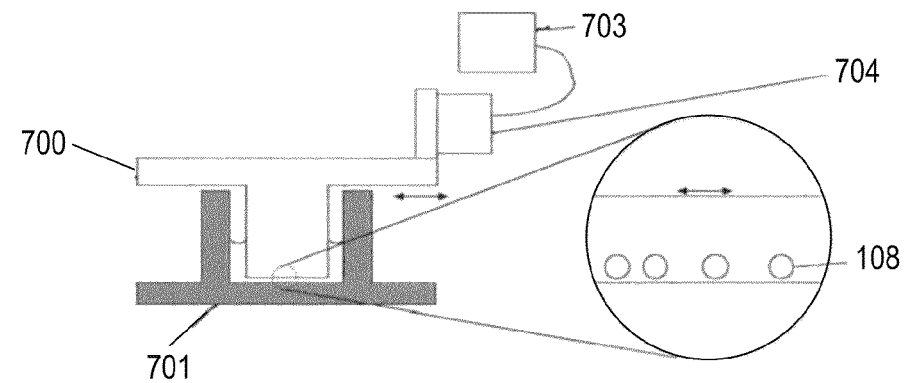

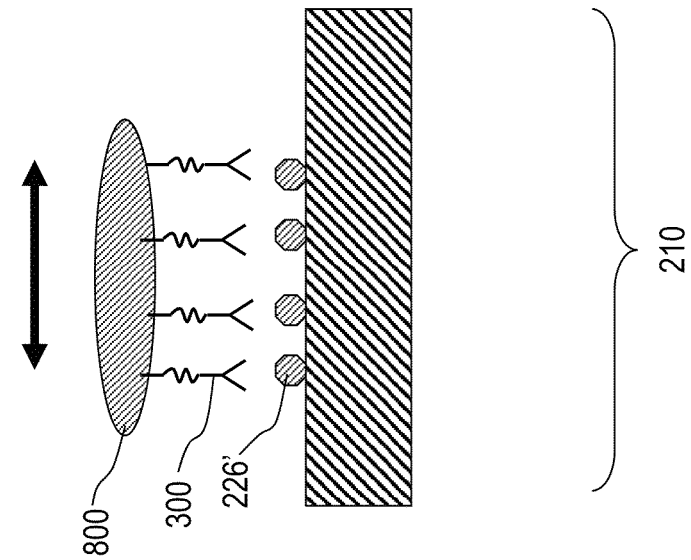
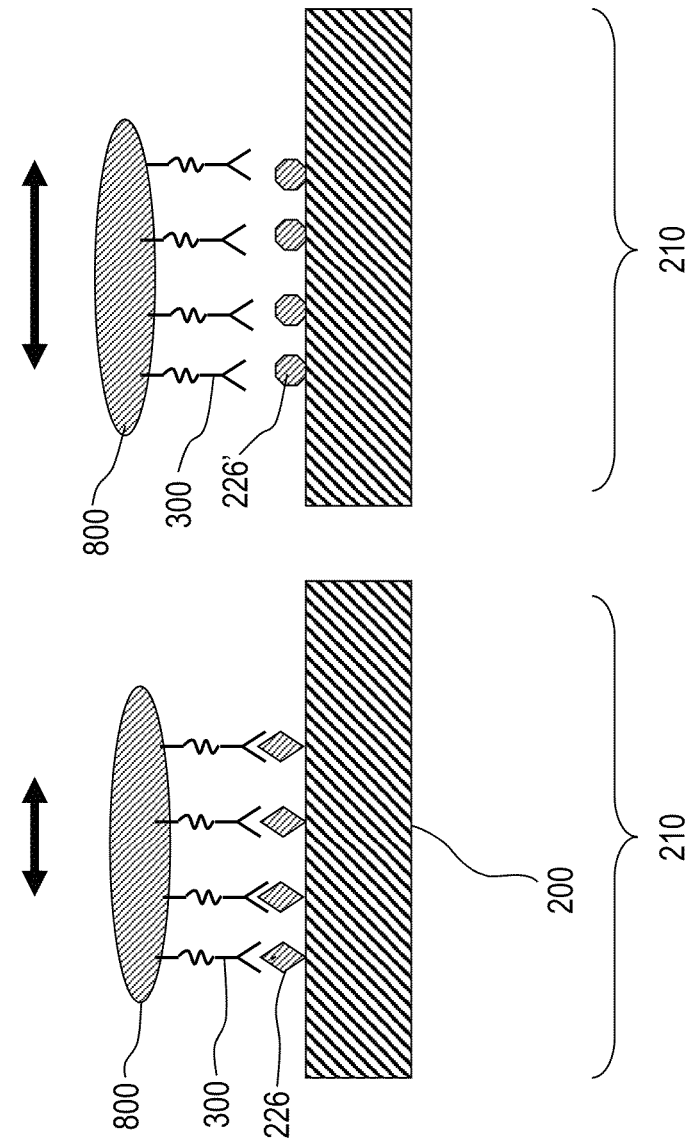

Standard VS Activated Cold: 4.8 micron silica

NSD value, brightfield illumination

FIG. 27
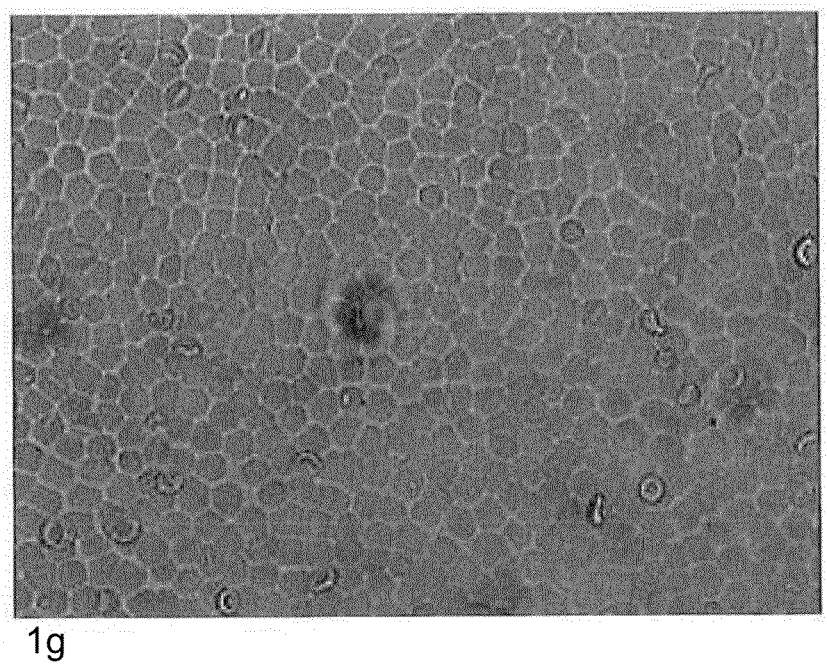
1g
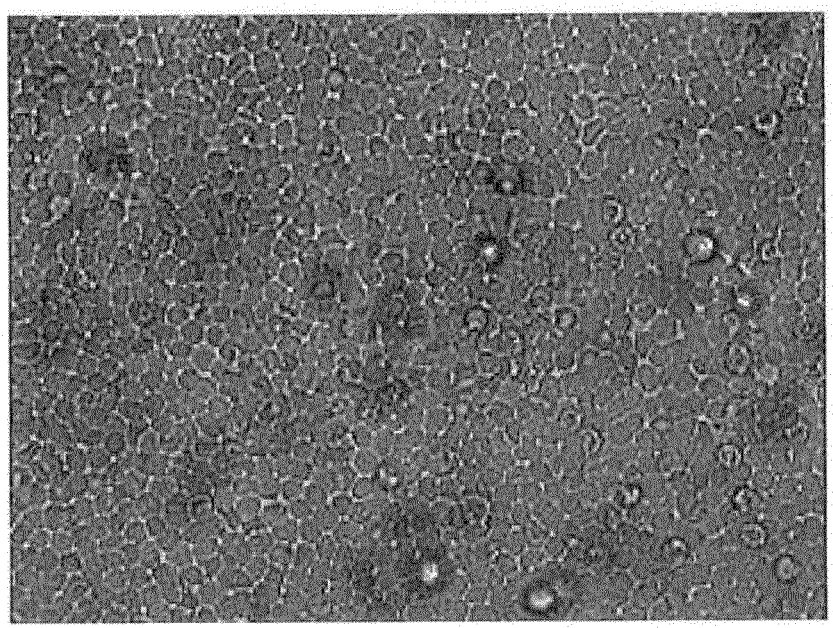
400g

Alba AB screening cells, 5 min centrifugation, saline rinse

METHODS AND APPARATUSES FOR DETECTION OF POSITIONAL FREEDOM OF PARTICLES IN BIOLOGICAL AND CHEMICAL ANALYSES AND APPLICATIONS IN IMMUNODIAGNOSTICS

CROSS-REFERENCE TO RELATED APPLICATIONS

The present invention is a 35 U.S.C. 371 National Stage Entry of PCT/US2011/000930, filed May 25, 2011, which claims priority from U.S. Provisional Patent Application Nos. 61/348,072, filed May 25, 2010, and 61/347,946, filed on May 25, 2010, the contents of all of which are herein incorporated by reference in their entirety.

BACKGROUND OF THE INVENTION

1. Field of the Invention

The present invention relates to methods and apparatuses for the detection of positional freedom of particles used in biological, biochemical, biophysical, physical, and chemical analyses. Major applications of the present invention include immunodiagnostics, such as blood typing and infectious disease screening.

2. Description of the Related Art

The use of arrayed molecules in formats such as microplates and biochips allows for an ever increasing amount of information to be retrieved about the natural world. Although many variants are known, use of such arrays typically involves immobilizing probes or analytes on a substrate and using a variety of techniques to measure the interaction of the immobilized molecules with other solution-phase molecules. Specific examples of such array techniques include immunoassays (e.g., enzyme-linked immunosorbent assays (ELISAs)) that are performed in microplates, commercial nucleic acid biochips and protein microarrays or biochips. Biochips most commonly use glass substrates, while microplates for ELISA are often constructed from gamma-irradiated polystyrene. Although arrays are typically "ordered", in the sense that patches of immobilized molecules are placed at defined locations with respect to each other or to reference features, so-called "solution-phase arrays" have also been commercialized. The solution-phase assay technology measures the binding of analytes to a suspension of beads. The suspension is created by mixing batches of particles that are co-labeled with binding probes and corresponding mixtures of two fluorescent identifier molecules in varying ratios. A flow cytometer detects bound fluorescently labeled analyte along with the identifier ratios.

In addition to the detection of individual molecules, particles (including biological cells) have been analyzed using array techniques. For example, it is known in the art to detect cell surface antigens through ELISA or flow cytometry. U.S. Pat. No. 6,251,615 to Oberhardt discloses testing cells using microscopy to detect cells bound to one of a plurality of capture surface regions with coupled antibody receptors.

However, a major limitation of conventional arrays is that long incubation times are usually required to reach a degree of binding that is sufficiently close to equilibrium to achieve the desired sensitivity. This may entail allowing samples or reagents to incubate in an ELISA microplate or biochip for many hours, and in some cases, longer than a typical business day of eight hours. Such delays can cause added expense, preclude use in emergency situations, and reduce data quality due to degradation of reagents and increases in non-specific (background) signal during the protracted incubation times.

Other limitations of conventional approaches include the need for analyte labeling steps and stringent washing steps, which introduce additional costs in terms of labor and equipment, and may impact data quality. Further, microplate based approaches use relatively large volumes of test samples and reagents.

One application for conventional arrays is in immunodiagnostics, such as to determine blood type. Blood typing entails determining the presence or absence of key surface antigens on human red blood cell (RBC) surfaces and/or determining the presence or absence of clinically relevant antibodies specific to RBC surface antigens. Conventional assays perform blood typing by detecting the agglutination of red blood cells (RBCs) upon the addition of the corresponding antibodies (see, for example, U.S. Pat. No. 4,894,347 to Hillyard et al.). Agglutination of a blood sample indicates a positive result for the antigen tested. Thus, blood typing methods are conducted in bulk to determine agglutination/adhesion, and indirectly measure the binding of the RBCs. Some methods for blood typing, referred to as "solid phase" methods, involve the immobilization of certain proteins or cells expressing certain proteins on a surface. These methods are generally done in bulk format. For example, a camera may detect whether most RBCs are on the walls of a well or at the bottom of a well by taking a single low-resolution image to see if the red color is at the central bottom portion of the well or along the edges. For strong signals and systems which are close to equilibrium, most cells may be found in similar states (most at the bottom, or most on the walls) giving rise to a reliable result for sufficient signal strength and incubation time.

Ensuring that blood typing is performed accurately is extremely important because RBCs from different individuals may have different antigens on their surfaces, and transfusion of whole blood or certain blood components from a donor having certain RBC antigens to a patient that lacks those antigens may cause an adverse transfusion reaction in the patient. This generally occurs if the patient has a natural immunization to the given antigens, which may occur with a non-matched ABO blood group, or if the patient has been immunized to blood antigens by prior exposure (e.g., Kell or Duffy group antigens). Thus, the potential for spurious results can occur due to possible immunization against blood cell antigens that is undetectable due to limits on measurement sensitivity or diminishing antibody concentration (titer) within an immunized patient's blood over time, or may also occur due to a possible variation in antibody titer and reactivity from person to person, or a potential variability in reagent specificity.

Present techniques for determining blood type are limited in their sensitivity, speed, and ability to test a sample for a large number of analytes. For example, the fact that conventional blood typing methods require agglutination or bulk surface binding, where most RBCs have to bind (and in many cases must bind strongly by forming multivalent attachments), limits the speed and sensitivity of the testing. Further, current technologies require a relatively large amount of blood (e.g., about 3 mL) for testing. The ability to type blood while utilizing a smaller volume would be of great utility, especially when dealing with newborns. The ability to reliably measure weaker binding levels, which have fewer bound cells and fewer attachments for each bound cell, would enable increased sensitivity (i.e., testing for lower titers with higher confidence), testing at much shorter times, or both benefits together.

With increased sensitivity, patient and donor blood can be more confidently matched. With increased speed, patients who have an urgent need for blood can be safely transfused with matched blood much more quickly. With increased capability for testing a large number of analytes, test costs can be reduced, additional tests can be adopted, and problems with specificity can be mitigated by testing against multiple related antibodies or reagent cells from multiple individuals. Expanding the test panel to include more tests of antigen variants or antibodies to these variants, can be valuable since variability is quite common due to genetic mutations and other variants, which is seen frequently in comparing populations with different ethnic backgrounds (and thus, genetic make-up), for example. If these advances can be made, the benefits could be extended to numerous other applications other than blood typing, including surface antigen characterization of stem cells, platelets, and cancer cells.

SUMMARY OF THE INVENTION

The present invention relates to methods and apparatuses for the detection of positional freedom of particles used in biological, biochemical, biophysical, physical, and chemical analyses. The methods and apparatuses of the present invention can detect and characterize a population of particles/cells based upon their detected mobility. In one embodiment consistent with the invention, analytic characterization of populations of cells is based on differences detected in populations of cells that bind to a substrate and those that exhibit weaker binding. Initially, cells are settled on the substrate, and in the presence of gravitational, Brownian, and other random or applied forces, some of the particles may exhibit translational movement. Particle movement is detected and measurements are computed to determine the presence and/or concentration of specific analytes.

Exemplary embodiments of the present invention feature methods for biological, chemical or biochemical analyses (i.e., assays) based on the discovery that the movement of particles associated with surfaces to which they are exposed, accurately measures the presence, absence or amount of an analyte on the particle, surface, or surrounding solution.

In particular, this movement, known as the "positional freedom" of the particle, and the microscopic measurement of this movement according to the methods and apparatuses of the present invention, characterizes the degree to which the particle—such as cells, viruses, or small polymeric and inorganic objects, such as microspheres or microbeads of various shapes and compositions—exhibits movement in relation to a binding surface (such as a substrate), or another particle. In particular, the positional freedom is reflected in a measurement of the positional fluctuation of the particle that is bound to, or associated with, a binding surface.

In embodiments of the present invention, a microscopy apparatus is used for carrying out the invention, and may utilize brightfield or darkfield microscopy, phase contrast microscopy, differential interference contrast (DIC) imaging or Nomarski microscopy, fluorescent microscopy, holographic microscopy, or any other microscopy techniques well known in the art.

In one embodiment, an in-line microscope apparatus designed to measure the mobility of particles (i.e., cells) in order to infer surface interactions (i.e., presence or absence of specific surface-particle interactions), and/or collective diffusion/visco-elastic properties of the particle dispersion (e.g., effective viscosity), is used. In another embodiment, a camera and a computer are included in the microscopy apparatus, in order to image different areas of the sample, and to assist in quantifying and analyzing the results obtained, to determine the binding reactions of the particles with capture surface regions on the substrate on which the particles are disposed.

Thus, the assay methods of the present invention may be implemented as a computer program product for use with the computer system.

In another embodiment consistent with the present invention, the microscopy apparatus includes a coherent light source (e.g., laser, superluminescent diode), where the coherent light is collimated by a collimator, and whose laser beam illuminates the sample. In this embodiment, the microscopy apparatus is operated according to well-known holographic microscopy techniques.

In another embodiment consistent with the present invention, a transparent, semi-transparent, or partially mirrored sample of particles and sample chamber in which the particles are disposed, with reflective coating, may be measured in reflection mode, involving the laser illumination (or alternative illumination source) to illuminate the sample from the collection side, with image formation occurring from the light reflected from the sample that is subsequently imaged onto the monitor of the computer system. This imaging method may also be referred to as reflected light imaging or epi-illuminated microscopy.

In one embodiment, the particles used in carrying out the methods of the present invention, may have a variety of physical and chemical attributes, and may be of different types, based on size, shape, and materials, yielding distinguishable images.

In one embodiment consistent with the present invention, the sample of particles used may further be modified by introducing reagents or non-reactive solutions onto the sample holder—before, during or after the measurements. The surface may be provided in a variety of devices, and in a variety of ways—i.e., in degrees of transparency and reflectiveness, and degrees of levelness or treatment with biomolecules etc.

In one embodiment, the sample of particles may be provided in a number of ways, or distinguished based on a label.

In one embodiment, when the particles are coated or otherwise have embedded fluorescent, or luminescent molecules or nanoparticles, which are distinguished by particle type based on fluorescent or luminescent emission spectrum, the microscopy apparatus shall be equipped with a fluorescent, luminescent excitation source, appropriate filters and dichroic elements as well as color detection capabilities (e.g., color camera and/or emission filter selections).

In one embodiment consistent with the present invention, the sample holder includes a simple microscope slide made of glass or plastic, with the particles being disposed or settled on its transparent surface.

In yet another embodiment consistent with the present invention, the transparent sample holder is a well plate (standard microtiter plate or custom well plate), or a simple passive microfluidic cartridge. The cover glass will be treated with the appropriate chemistry for the particular application desired.

In yet another embodiment consistent with the present invention, the microtiter plate may or may not have a customized configuration, including optically transparent caps, sample delivery zones, sample viewing zones etc. For example, the microtiter plate may be an open-well disposable with a cap or a lid. The cap is disposed in a well to provide a top surface during incubation and measurement steps.

In another embodiment consistent with the present invention, a simple microfluidic sample cartridge includes an inlet for introducing one or more solutions, and an outlet for air and solutions to exit the system as needed for the given assay.

In another embodiment consistent with the present invention, a microfluidic sample cartridge includes three regions, for example, on the cover glass or substrate, which are functionalized for a binding experiment (i.e., has three capture surface regions).

In one embodiment, the microfluidic cartridge may be an automated fluidic device, and the well plate may be a microtiter plate device, each being compatible with data acquisition and analysis (i.e., microscopy apparatus), as described herein. The instrumentation outlined herein may be integrated with a robotic microtiter plate handling machine for automated (and parallelizable) fluid delivery from sample containers to each well, sample mixing and incubation capabilities, as well as parallelized microtiter plate measurement capabilities, which may be programmable and automated. Thus, an assay may be designed to perform multiple tests on one or a number of samples, in a parallel fashion.

The chip design according to one embodiment consistent with the present invention, encompasses a disposable cartridge for immunodiagnostics, for example, on which ABO/Rh blood typing, Antibody Screening, and Plasma filtration, can be performed, in addition, Weak D antigen, Extended Phenotyping, Direct Antiglobulin Test (DAT), and Antibody Identification are performed.

The instrument in which the Filtration or other plasma separation disposables, ABO/Rh disposable, and Antibody Screening (AbS) disposables, are inserted for testing, is fully automated and accepts whole blood tubes and vials, and does not require manual reading of the results like conventional tests. Further, the present invention disposables do not require centrifuged blood as input (and thus, no external centrifugation since it separates plasma from whole blood on the disposable), and has reagents and controls in the disposable itself.

There are several embodiments consistent with the present invention, which provide activated methods which are used for applying forces to the physical sample holder or to the fluids within the sample, in order to determine the extent to which binding interactions occur. In particular, the physical force application means includes an abrupt or continuously periodic movement of the translation stage, fluid, or sample holder using external means such as caused by a pneumatic/hydraulic pressure oscillator, a piezoelectric hydraulic actuator, a piezoelectric stage oscillator, a pneumatic or hydraulic valving/perturbation device, a thermal actuator, an acoustic radiation device, and a well cap activation device.

Advantages of these activated methods include: 1) stronger (and thus more robust and confident) separation between bound and unbound particles; 2) greater robustness against illumination intensity variations, vibrations, slightly out-of-focus particles, imperfections in the flatness of the sample, imperfect leveling of the stage or sample, and other issues which introduce noise into a measurement, 3) potentially actively overcoming nonspecific binding (NSB), by differentiating between NSB and specific binding where NSB may have lower binding strength than the driving force of the activated method, and 4) encouraging faster exploration of configurations between a particle and the substrate, allowing for speedy binding and/or stronger binding—thereby speeding up the test measurements. Thus, these activation methods can be used to speed up the interaction and binding process, to differentiate the binding, and during the measurement step, to enhance the discrimination and confidence for each binding measurement. The intensity of the activation can be uniform, variable, or intermittent, and may be tuned at different times to optimally enhance the effects desired.

Prior to conducting the methods of the present invention, focusing of the microscopy equipment may be performed in order to achieve the best results. In contrast to traditional microscopy techniques, the use of a coherent source to illuminate the particles allows numerical processing of a single out-of-focus image of the sample to determine the correct focal plane of the particles in a quick fashion.

The methods of performing the present invention on the apparatuses described above, include introducing a population of microscopic particles into a chamber and settling the particles on a surface in order to measure any binding interactions. The present invention may employ various systems to settle the particles on the substrate. They include gravity, centrifugal, flow-based, diffusion-based, magnetic-based, and holographic tweezing based systems.

In the methods of the present invention, a solution containing particles is placed on a slide, or made to flow through a chamber of a well plate or microfluidics device, and over a substrate, and the particles settle on the surface according to gravity, centrifugal forces, etc. The particles are investigated to identify whether the particles bind to the capture surface regions on the substrate (or on other particles).

In one embodiment, the capture surface regions on the substrate include binding probe(s) which render the substrate capable of specifically interacting with a given analyte or other chemical entity. The analyte can be on the surface of the substrate, on a surface of the particle, or in the solution. In the present invention, a glass slide, coverslip, plastic, or silicon substrate may have multiple capture surface regions with specific probes to form a sensing array such as a DNA array, protein array or other microarray.

In one embodiment, the particles are caused to contact capture surface regions on the substrate. The contact may occur passively by settling of the particles by gravity, or by active means, such as through centrifugation, electrophoresis, activation methods described above, or by optical forcing, or moving the particles to the substrate using optical trapping techniques, among others. After contact between at least one of the particles and a corresponding capture surface region of the substrate, a specific binding interaction may occur between them if a specific chemical entity is present on the surface of the at least one particle. In that case, the binding between the particle and the surface creates a "surface-associated" particle, thereby creating a plurality of "tethers" between the particles and the capture surface regions. In other words, the specific binding interaction exhibits a characteristic avidity (i.e., cooperative or cumulative affinity due to multiple chemical/biochemical interaction analogous to the avidity of multivalent antibodies).

In one embodiment of the present invention, once bound, the particle does not rupture its bond to the capture surface region etc., but rather, the degree to which the particle exhibits positional freedom may be used to determine the presence, absence or amount of the analyte.

In one embodiment of the present invention, the particle fluctuation includes multiple, successive changes in the particle's motion. For example, the particle movement may change direction due to thermodynamic pressure fluctuations (as gives rise to Brownian motion for completely free particles), or due to cyclical application of forces in accordance with the activation methods described above. Such translational movement, or positional fluctuation, may result from thermodynamic fluctuations or other influences, e.g., oscillatory flows, convection, acoustic waves, or other forces (i.e., activation methods).

In one embodiment, the amount of particle motion is increased by the activation methods described above, in order to enhance the degree of movement, while the particle still remains bound to the capture surface region.

When the binding potential of the capture surface region is properly tuned to a particular affinity with the particle for a specified temperature range, measurements of the positional freedom of the particle reveal that the presence of specific binding interactions between the capture surface region and the particle is correlated with a reduced amount of positional freedom.

The particles are illuminated using the microscopy apparatus of the present invention, and bright-field, dark-field, phase contrast, differential interference contrast (DIC), holographic imaging, and other optical microscopy methods may be used. Images of the particles are collected by the camera and analyzed by the computer. A time-series of images of the particles in the field of view are acquired by the camera (at least N=2 images, but a higher number of images may provide greater precision). Important parameters which may be chosen include the time interval between images and the total time over which a particle is observed, in accordance with the type of particle and the imaging method as well as whether an actuation method is selected.

The particles to be analyzed in the images may be chosen based upon their size, shape, orientation, appearance, proximity to other particles, where they are located in the image, etc., and can be based upon one image or several images.

A measure of positional fluctuation is a quantitative measure of the response of a surface-associated particle to a stimulus, from which the positional freedom of the given surface-associated particle is inferred. How the particles move in response to small forces, such as random thermal forces (i.e., those that may give rise to Brownian motion for unbound particles in suitable circumstances), bulk motion of the suspending fluid caused by an applied pressure (i.e., from valving or otherwise controlling pressure at inlets, or by using a displacement such as a moveable membrane), induced by motion of the substrate/sample container, by acoustic vibration, and other forces from the activated methods described above, are observed and quantified.

The measure of positional fluctuation may be a categorical or qualitative measurement (e.g., a binary value). Alternatively, the measure of positional fluctuation may be a quantitative value. The measure of positional fluctuation may be a statistical measure that describes the time dependent positional evolution of a particle in a specified neighborhood and may be expressed as the variance, standard deviation, root mean square (RMS) travel, or autocorrelation function of the particle position associated with a time-series of observations.

Thus, a particle that is adhered to a capture surface region is determined to have the specific binding target of the capture surface region present on its surface (or otherwise present and available to enable binding of the particle to the surface region) if it fails to move greater than a certain degree after a certain amount of time or number of observations.

The measure of positional fluctuation may be derived from a recorded time-series of measurements of the position of the particle in the plane of the surface of the substrate, which may be expressed in terms of x, y if a Cartesian coordinate system is used. Some or all of the recorded observations may be stored in a tangible computer memory or database for later processing of positional freedom and determination of related values such as binding affinities. Alternatively, the observations may be processed continuously by the computer program.

Changes in positional freedom in the z-axis (i.e., the direction orthogonal to a plane defined by the surface of the substrate) may also, through coupled motion, influence the positional fluctuation measured from the x, y positional data. Alternatively, the motion in the z-axis may be measured directly by the computer program and used in the determination of positional fluctuation. Polar coordinates may also be used. The positional data of the time-series may be measured in relation to a fiduciary marking (e.g., of the first surface or microscope optics), of the first surface region, of a sample holder or microscope stage, or of other particles or microscopic objects. Optionally, the path of particles may be tracked and data about the path stored to the tangible computer medium according to particle tracking methods described below.

The measure of positional fluctuation of the particles may be determined for each particle individually (including through parallel processing of an image of multiple particles), or images of multiple particles may be manipulated mathematically or computationally in ways that do not require identification of individual particles. For example, an algorithm may be used to compute a total degree of movement within the series of images. Alternately, one algorithm may detect regions where movement occurs, and this may be used in conjunction with or independently from other information about the number of particles in the images.

Measures of positional fluctuation are carried out with the naked eye, or by using a microscopy apparatus. In another embodiment, the positional fluctuation is measured using a microscopy technique involving coherent illumination (holographic fluctuation microscopy). For example, holographic microscopy enables acquisition of high-resolution three-dimensional position data. Accordingly, confident determination of the presence or amount of analyte may be made more quickly, or a higher confidence or sensitivity may be achieved for a given data acquisition time.

The method of analysis includes finding a value of the positional freedom of the particles to determine the degree of binding. This degree of positional freedom can be inferred by measuring the degree of fluctuation movement of the particle from the sequence of acquired images. This may be done through a variety of methods including particle recognition and tracking, computing the average of multiple images, computing the average difference between successive image frames, and computing the pixel-wise variation in intensity throughout the time sequence of image. Typically, the computation is done in such a way as to characterize each particle with a measure of movement.

In one embodiment, calibration data is first obtained for one, two, or multiple samples. For a simple test with two possible outcomes, two control samples (or two sets of control samples where each set has similar nature) can be measured to obtain calibration data. For tests with more than two possible outcomes, such as a measurement where a continuously varying measure may be desired (e.g., measuring temperature, Ph, concentration of an analyte, etc.), multiple calibration samples may be used.

In one embodiment, two calibration samples are measured and a single (calibration) threshold value of positional freedom measurement is obtained. Measurements of the positional freedom of the particles in the test sample are compared to the threshold, and if they fall below the threshold, then binding interactions are inferred. If the particles have measurements above the threshold, then no binding interactions are inferred. Thus, a measurement of a number of particles in the test sample yields a count of the number of particles inferred to be more strongly bound and a count of those which are less strongly bound, which alternately can be expressed as a percentage which are strongly bound. By comparing these counts or this percentage to one or multiple reference values, a final measurement outcome can be called, such as "positive", "negative", or "inconclusive" for the given test.

In another embodiment, the set of positional freedom measurements of the particles include a positional freedom distribution. The positional freedom distribution may be obtained for reference samples (e.g., determined from many calibration runs on control samples) as well as for the test sample in question. The test distribution may be compared to the set of reference distributions to determine which control sample the test sample most closely resembles. This may be done numerically through a number of methods including projection, correlation, dot product, minimizing differences, integrating regions of the curves, or other methods. This method may yield a binary result (such as "positive" or "negative") or a non-binary result (such as 0 (negative), 1 (extremely weak), 1+, 2, 2+, 3, 3+, 4, 4+, or 5 (very strong)). Thus, the collection of fluctuation measurements can be compared to the collection of fluctuation measurements from reference samples of known character.

The present invention has applicability to at least the field of immunodiagnostics (which includes blood typing), and beyond that field, to other diagnostics including live cell assays for pharmaceuticals (i.e., for research past screening and diagnostic testing) and allergy testing (e.g., IgE antibody testing). In particular, applications include, forward typing, reverse grouping, and antibody screening (IgM and IgG class antibodies).

In other embodiments consistent with the present invention, methods and apparatuses disclosed herein are suitable for infectious disease screening (e.g., human immunodeficiency (HIV) virus, hepatitis B virus (HBV), syphilis, human T-lymphotropic virus (HTLV), hepatitis C virus (HCV), syphillis, etc.), by testing for antibodies to these infectious agents or in some cases testing for the agents themselves. Further, depending on the desired analysis, mixtures of probe types and specificities may also be used to detect the presence of cells that bear a unique combination of complementary antigens (e.g., certain cancer or stem cells).

In other exemplary embodiments, the methods of the present invention may include variants on the chemistry and techniques, including: bioinert moieties to reduce the probe density with a minimal or negative contribution to nonspecific binding interactions between the cells and the capture surface regions; direct assays where the analyte is coupled to the substrate; indirect assays, where there is a probe complex; competitive assays involving detecting an event associated with displacement or blocking of an analyte or reporter or other molecule; analyte specificity where the capture surface regions have specificities for different analytes; covalent tethers where a nucleic acid oligo extension and ligation assay may be used to covalently link specifically-formed tethers; the screening of molecule libraries; the elimination of a washing step because of the variations in positional freedom and resulting measurable positional fluctuation of the positive and negative particles; use of a sensing array identification; the use of control capture surface regions; the sizing of the particles used to enhance the analysis of positional freedom; control of the length of the tether or relation to a fiduciary reference, and use of a reference value, such that the particle is determined to have the specific binding target of the capture surface region present on its surface if it fails to move greater than a predetermined certain distance after a predetermined certain amount of time, or predetermined certain number of observations.

Further embodiments of the present invention are based on the discovery that for at least some probe-types, nonspecific binding of settled particles occurs at a different rate than specific binding. As a result, it has been discovered that one can measure a positional fluctuation signal based on early time points after settling of the particles. Tracking of the evolution of the positional fluctuation measurements over time may allow for improved discrimination of non-specific binding from specific binding. Alternately, the system may be thought of as having multiple effects which occur with different time evolutions (for example, with different characteristic timescales or progression rates) and by tracking the evolution over time, the level of each contribution may be determined. For example, in a simple case where nonspecific binding is found to occur rapidly compared to specific binding, the early positional fluctuation may be subtracted from a positional fluctuation measurement based on later time points. In other words, the computation of positional fluctuation may include a step in which the computer program operates to calculate a measure related to the time evolution of the particle position and optionally corrects for nonspecific binding that occurs with a greater kinetic time-constant than the time-constant for nonspecific binding. As noted above, this may be done through curve-fitting or other algorithms known in the arts of kinetic or molecular assay technology.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

The foregoing features of the invention will be more readily understood by reference to the following detailed description, taken with reference to the accompanying drawings.

FIG. 1D is a schematic diagram showing another embodiment consistent with the present invention, where a sample of particles and sample chamber with reflective coating may be measured in reflection mode.

FIG. 1F shows schematic diagrams of an exemplary microfluidic cartridge, according to one embodiment consistent with the present invention, with perspective view A, cross-sectional view B, top view C, and top view of the sensing array D.

FIG. 1G shows schematic diagrams of an exemplary open well sample cartridge, according to one embodiment consistent with the present invention, with perspective view A, cross-sectional view B, and top view C.

FIG. 1H shows a schematic diagram of a well plate with a cap which defines a specified gap between planar surfaces, according to one embodiment consistent with the present invention.

FIG. 2A shows a schematic diagram of a microfluidics device connected to an exemplary system for oscillating the fluid pressure (and thus fluid flow), according to one embodiment consistent with the present invention.

FIG. 2D shows a schematic diagram of a microfluidics device incorporating a pneumatically-driven (or hydraulically driven) system for oscillating the hydrodynamic pressures and flows, according to one embodiment consistent with the present invention.

FIG. 2E shows a schematic diagram of a microfluidics device connected to an exemplary thermal actuator, according to one embodiment consistent with the present invention.

FIG. 2F shows a schematic diagram of a microfluidics device connected to an acoustic source, according to one embodiment consistent with the present invention.

FIG. 2G shows schematic diagrams of a cap used in a cartridge with wells, with drawing A showing the well with the cap in place, drawing B showing the use of a linear solenoid actuator to oscillate the cap for activation, and drawing C showing a piezoelectric actuator which drives the cap movement for activation of the particle movement, according to embodiments consistent with the present invention.

FIG. 18A is a cross-section of a direct assay, where an analyte antigen is bound to (or captured by) a capture surface region and a particle with immobilized antibody probes is contacted with and bound to the capture surface region, and FIG. 18B shows a situation where the antibody does not recognize a non-binding antigen (i.e., no binding takes place), according to one embodiment consistent with the present invention.

FIG. 27 shows two slides under microscope, and with particles (i.e., red blood cells) under centrifuge at 1 g and 400 g (gravity), respectively, according to one embodiment consistent with the present invention.

DESCRIPTION OF THE INVENTION

Figure 1A:
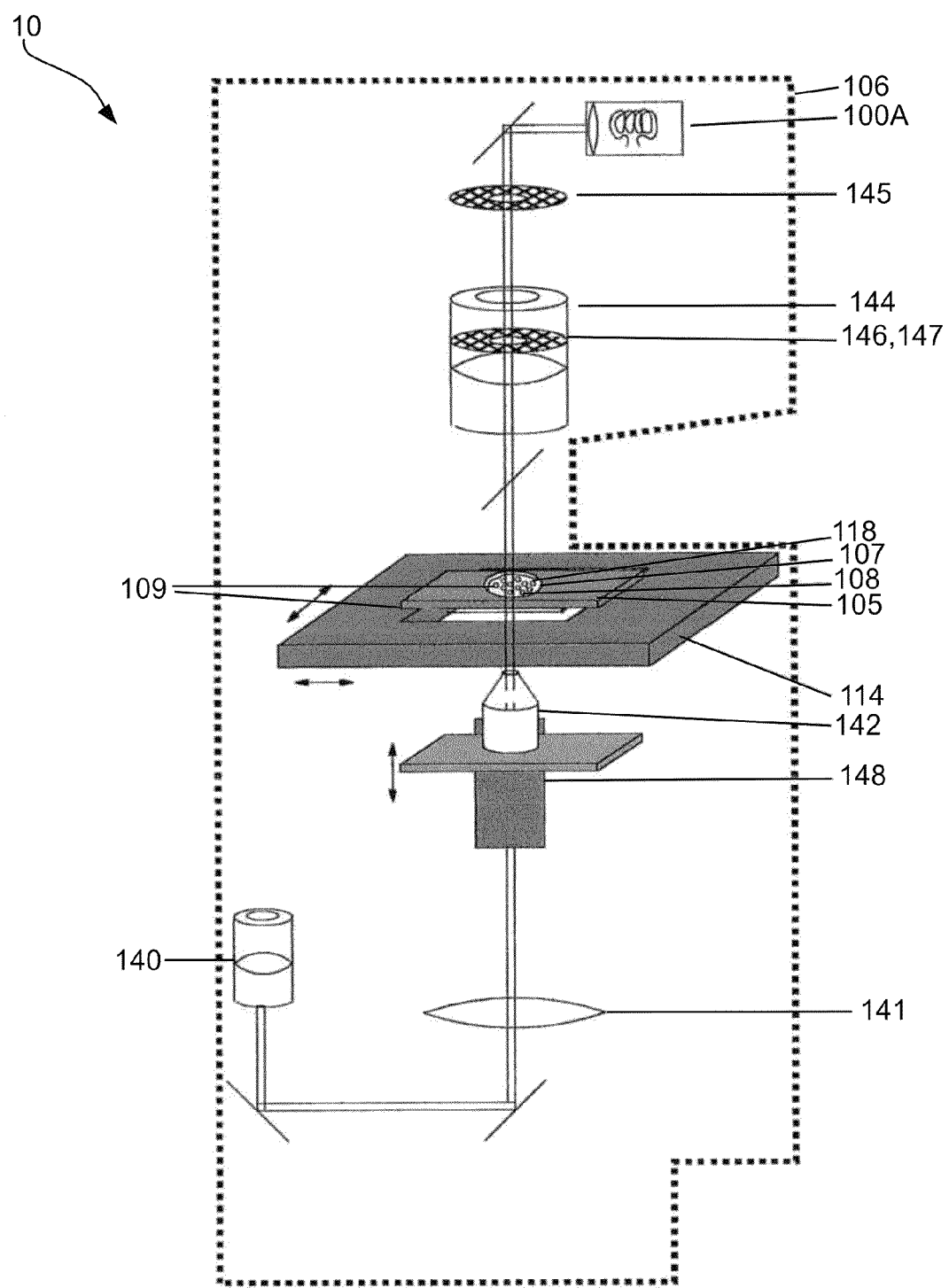
FIG. 1A is a schematic diagram showing a first embodiment of a microscopy apparatus consistent with the present invention, where the microscopy apparatus in its simplest form.

The present invention relates to methods and apparatuses for the detection of positional freedom of particles used in biological, biochemical, physical, biophysical, and chemical analyses. In particular, the present invention relates to methods and apparatuses which can detect and characterize a population of particles/cells based upon their detected mobility. In one embodiment consistent with the invention, detection of certain cells is based on differences detected in populations of cells that bind to a substrate and those that exhibit weaker binding forces. Initially, cells are settled on the substrate, and in the presence of gravitational, natural thermodynamic pressure fluctuations, and other random or applied forces, some of the particles may exhibit translational movement. Particle movement is detected, and measurements are computed, according to the methods and apparatuses of the present invention, to determine the binding of specific analytes.

Exemplary embodiments of the present invention feature methods for biological, chemical or biochemical analyses (i.e., assay), and relate to the discovery that the movement of particles associated with surfaces to which they are exposed, accurately measures the presence, absence or amount of an analyte on the particle, surface, or in the surrounding solution. Additionally, these measurements can be used to reveal environmental properties such as temperature, pH, or other environmental parameters.

In particular, this movement, known as the "positional freedom" of the particle, and the microscopic measurement of this movement according to the methods and apparatuses of the present invention, characterizes the degree to which the particle—such as cells, viruses, or small polymeric and inorganic objects, such as microspheres or microbeads of various shapes and compositions—exhibits movement in relation to a binding surface (such as a substrate), or another particle. In particular, the positional freedom is reflected in a measurement of the positional fluctuation of the particle that is bound to, or associated with, a binding surface.

In particular, the binding surface is that portion of a surface that is capable of analyte or particle binding. The binding surface (i.e., substrate or surface of another particle) may have regions known as "capture surface regions", where interactions take place between the particles and the binding surface, to accurately measure the presence, absence or amount of an analyte on the particle, the capture surface region, or in the surrounding solution, or to measure an environmental or system condition to which the degree of binding is sensitive. Thus, a "surface-associated particle" is a particle that is in close enough proximity to a capture surface region so that specific binding interactions between the particle and the capture surface region may take place under suitable conditions for binding, if specific binding partners are present.

Apparatuses

The following apparatuses may be used in order to accomplish the goals of the present invention. However, one of ordinary skill in the art would recognize that variations of the apparatuses described, or other types of apparatuses, may accomplish the desired methods.

Microscopy Apparatus

In embodiments of the present invention, a microscopy apparatus is used for carrying out the invention, and may utilize brightfield or darkfield microscopy, phase microscopy, differential interference contrast (DIC) imaging or Nomarski microscopy, fluorescent microscopy, holographic microscopy, or any other microscopy techniques well known in the art.

Embodiment 1

In one exemplary embodiment, and in the simplest form of the present invention, FIG. 1A shows a schematic diagram, showing an in-line microscope apparatus 10 designed to measure the mobility of particles (i.e., cells) in order to infer surface interactions (i.e., presence or absence of specific surface—particle interactions), and/or collective diffusion/visco-elastic properties of the particle dispersion (e.g., effective viscosity).

In the exemplary embodiment of FIG. 1A, the microscopy apparatus 10A, which can perform brightfield microscopy, includes an illumination source 100A (e.g., LED, incandescent, arc lamp) which illuminates a transparent sample holder 105 (i.e., microscope slide) of a microscope 106. The transparent sample holder 105 has a treated or untreated surface 109, on which a sample 107 bearing particles 108 (i.e., cells) is disposed. The microscopy apparatus 10 includes a supporting structure or base (not shown) which contains the illumination source 100, and may incorporate a collimating lens or other optics, an objective lens 142 and tube lens 141 (which together form an image of the sample 107), an ocular lens 140 (or binocular lens), a condenser 144 which directs light to pass through the sample 107, and a translation stage 114 which allows mechanical movement of the sample holder 105. Adjustment knobs (not shown) and a focus mechanism 148 perform focus adjustment. A field stop 145 adjusts that portion of the sample area 105 over which illumination light is directed. Additionally, the condenser 144 may incorporate not only a lens but also an iris, e.g. an aperture stop 146, to control the range of angles (e.g., numerical aperture) over which illumination light approaches the sample 107. Additionally, the condenser 144 may incorporate a phase ring 147 which can also be used to limit the angles at which light approaches the sample 107. The phase ring 147 may be used for phase contrast imaging when used with a suitable objective lens 142.

Additionally, the phase ring 147 or appropriate condenser 144 configuration can allow for darkfield microscopy in which the illumination light from the condenser 144 reaches the sample 107 at angles which are not collected by the imaging optics, creating a situation where the imaging optics only accepts light which is reflected, refracted, scattered, or otherwise has its angle of trajectory altered by the sample 107. In this embodiment, the apparatus 10 may include a phase ring 147 or aperture to illuminate the sample 107, in which higher angle (higher numerical aperture (NA)) rays are unable to reach the image plane due to the lower NA setup of the objective lens 142 or overall imaging system. Alternately, fluorescent or epifluorescent imaging may be done with suitable use of filters and illumination as is well-known in the art (not shown).

Finally, an oil immersion objective lens 142 and a special immersion oil may be placed on a glass cover (not shown) over the sample 107, to improve the resolution of the observed sample 107. Alternately, a different immersion fluid may be used such as water or glycerine, with an appropriately chosen objective lens 142. Generally, higher numerical aperture objective lenses provide the benefit of higher resolution. The benefit is balanced with the added effort of using liquid immersion fluids required for the highest NA objective lenses, as well as the benefit of having a large field of view available to lower magnification and NA objective lenses. For simplicity, an air objective lens 142 may be chosen.

Embodiment 2

Figure 1B:
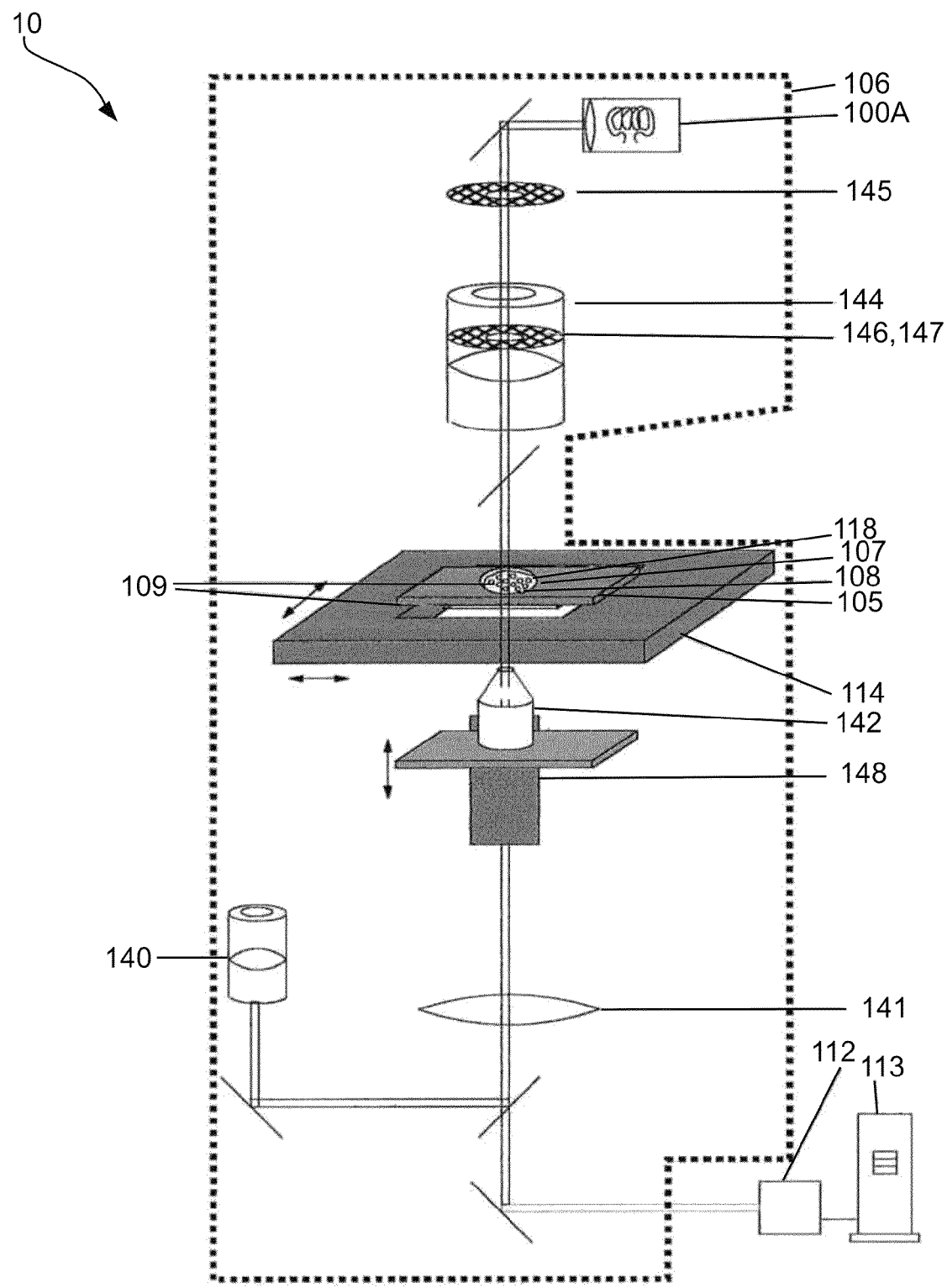
FIG. 1B is a schematic diagram showing a second embodiment of a microscopy apparatus consistent with the present invention, where the microscopy apparatus includes a camera and computer.

In another embodiment consistent with the present invention, a camera 112 and a computer 113 are included in the microscopy apparatus 10, as shown exemplarily in FIG. 1B. The cells/particles 108 may be imaged by the microscope objective 141, which with the tube lens 141 creates a magnified image of the cell/particles 108 on the CCD or CMOS camera 112, which is connected to a computer 113 for image processing etc. The camera 112 may include automatic zoom hardware and control mechanisms. Different areas of the sample 107 may be imaged by translating the sample 107 using a translation stage 114 (e.g., motorized microscope translation stage), which is well-known in the art. Various activated methods (discussed further herein) may be employed.

The sample holder 105 may also allow all or parts of the measured areas to be temperature controlled, allowing for example incubations to occur at optimal temperatures for biomolecular interactions to take place. Furthermore, the sample plane that is imaged by the microscope 106 may be adjusted by using the focus control adjustment knobs (which may be motor driven as well). Those of ordinary skill in the art would find that other enhancements to this or other microscopy apparatuses 10 may be used in order to achieve the desired results.

It is noted that although the present invention may be accomplished by viewing the binding reactions with the naked eye or with the ocular lens 140 of FIG. 1A, the use of the camera 112 and computer system 113, with the microscopy apparatus 10, is also useful in quantifying and analyzing the results obtained, to determine the binding reactions of the particles 108 with the surface 109.

With respect to the computer system 113, the system 113 includes display means (i.e., monitor, screen etc.), input means (i.e., keyboard, voice activated etc.), and may have processing and memory capabilities well known in the art. The computer system 113 may be in a client and/or server environment, or a distributed environment The assay methods of the present invention may be implemented as a computer program product for use with the computer system 113. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems.

It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Embodiment 3

Figure 1C:
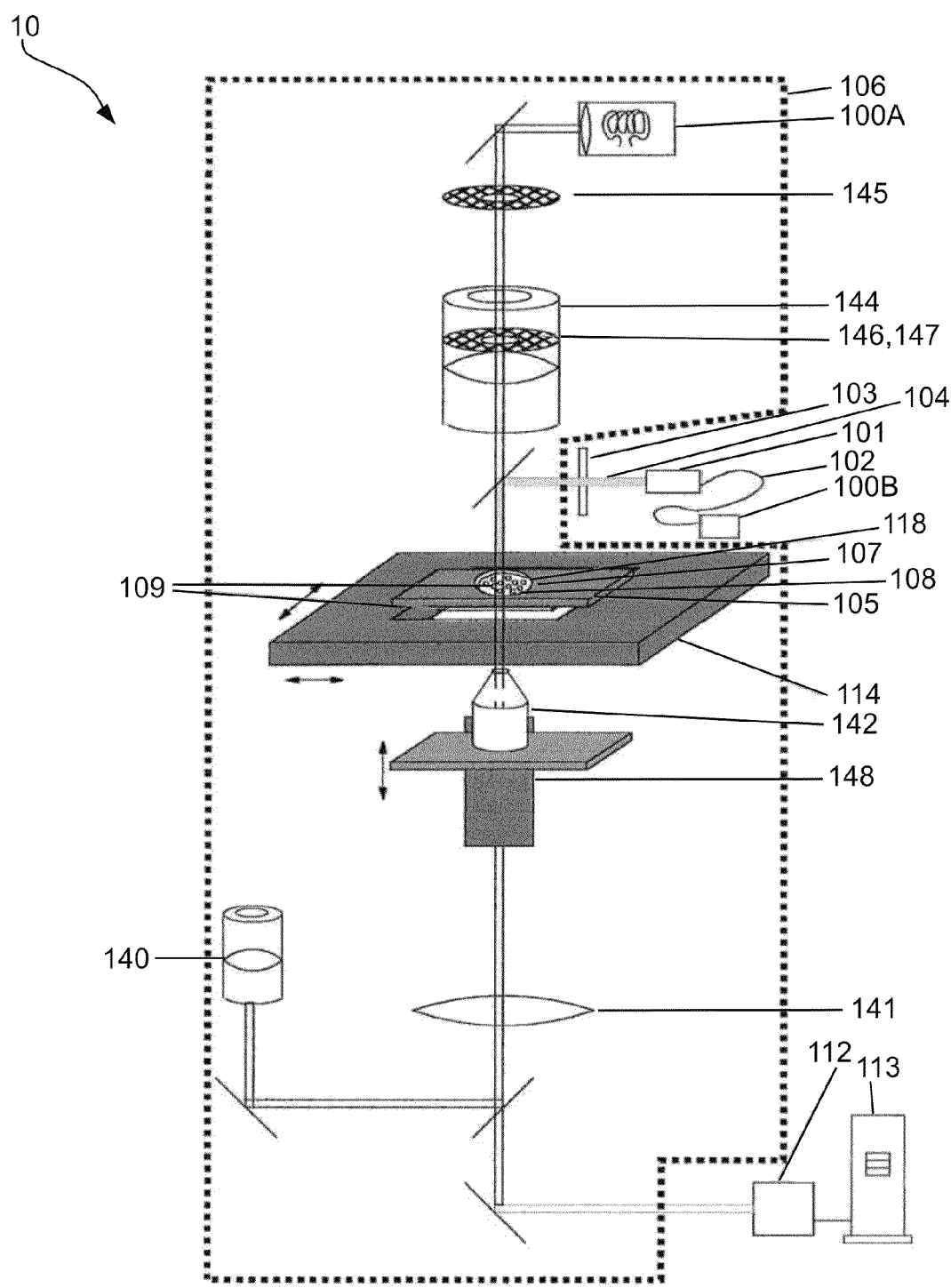
FIG. 1C is a schematic diagram showing a third embodiment of a microscopy apparatus consistent with the present invention, where the microscopy apparatus includes laser illumination, as well as a camera and computer.

In another embodiment consistent with the present invention, FIG. 1C shows a schematic diagram of an exemplary in-line microscope apparatus 10, which is also designed to measure the mobility of particles to infer surface interactions.

In the embodiment as shown in FIG. 1C, the microscopy apparatus 10 used for carrying out the present invention includes a coherent light source 100B (e.g., laser, superluminescent diode), where the coherent light is collimated by a collimator 101, and whose laser beam 104 illuminates a transparent sample holder 105 (i.e., microscope slide) of a microscope 106. The laser light 104 from the coherent light source 100 may travel to the collimator 101 as a "free space beam" or through an optical fiber (e.g., fiber optic patchcord 102). Optionally, a pinhole or iris/aperture 103 may be placed between the collimator 101 and the sample holder 105 to reduce the illuminated field and associated scattered light from illuminating an overly large area, thus acting as a field stop.

In this embodiment, the coherent laser source 100 used has a short coherence length (<400 µm), and operates at 660 nm. Well-known holographic microscopy techniques can be applied to this embodiment.

As with the previous two embodiments shown in FIGS. 1A and 1B, the cells/particles 108 may be imaged by a microscope objective 142 and tube lens 141, which allows the magnified pattern of the cell/particles 108 to be imaged on a CCD or CMOS camera 112, which is connected to a computer 113 for image processing etc. The camera 112 may include automatic zoom hardware and control mechanisms. As noted above, different areas of the sample 107 may be imaged by translating the sample 107 with a translation stage 114 (e.g., motorized microscope translation stage), which is well-known in the art. Methods and apparatuses of moving the translation stage 114 may also include the activated methods described further below. Also, as stated above, the sample holder 105 may also allow all or parts of the measured areas to be temperature controlled, allowing for example incubations to occur at optimal temperatures for biomolecular interactions to take place. Furthermore, the focal plane that is imaged by the microscope 106 may be adjusted by using the focus control 148 (which may be motor driven as well).

As stated above, the computer system 113 has hardware and software requirements, and processing and memory capabilities well known in the art, and may be in a client and/or server or distributed environment.

The assay methods of the present invention may be implemented as a computer program product for use with the computer system 113. As stated above, such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. As noted above, the medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems.

As stated above, it is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). As noted above, some embodiments of the invention may be implemented as a combination of both software (e.g., a computer program product) and hardware. Still other embodiments of the invention are implemented as entirely hardware, or entirely software (e.g., a computer program product).

Reflection Mode

In another embodiment consistent with the present invention, a transparent, semi-transparent, or partially mirrored sample of particles 108 and sample chamber 118 with reflective or partially reflective coating 120 (see FIG. 1D), may be measured in reflection mode, involving the laser illumination 100B (or alternative illumination source) (see FIG. 1C) to illuminate the sample 107 from the collection side, and image formation occurring from the light reflected from the sample 107 that is subsequently imaged onto the monitor of the computer system 113. Alternately, incoherent illumination could be used, such as brightfield, darkfield, fluorescence, or other imaging methods. When doing so, typically improved results are obtained when using polarization filters to reduce specularly reflected light off the smooth interfaces, such as the surfaces of optics and the sample chamber, as is well-known in the art.

Particles

The particles 108 used in carrying out the methods of the present invention, may have a variety of physical and chemical attributes, and may be of different types, based on size, shape, and materials, yielding distinguishable images. For example, a particle 108 may be a regularly shaped bead with some symmetry (e.g., spherical, prolate spheroid, oblate spheroid), or an irregularly shaped bead. A particle 108 may be made of one type of material or of multiple types of materials. A particle 108 may be solid, porous, or have a hollow core. A particle 108 may be fully or partially coated with other material(s). A particle 108 may be metallic or partly metallic. A particle 108 may be non-metallic or partly non-metallic. A particle's surface may be treated to apply a texture. A particle 108 may be a silica bead with linker molecules on the surface, or a silica bead with biomolecules or synthetic molecules attached to the surface. A particle 108 may also be a silica bead with biomolecules or synthetic molecules attached to the linker molecules on the surface. A particle 108 may be a bead coated with, or otherwise embedded with, a fluorescent or luminescent label molecule(s) covalently or non-covalently attached to it or integrated with it, which may also distinguish particle type based on fluorescent or luminescent emission spectrum. A particle 108 may be a bead coated or embedded with a combination of different fluorescent or luminescent label molecule(s) covalently or non-covalently attached to it or integrated with it, which may also distinguish particle type based on fluorescent or luminescent emission spectrum. A particle 108 may be a bead with a nanoparticle(s), or magnetic nanoparticle(s), or fluorescent nanoparticle(s), covalently or non-covalently attached to it or integrated with it.

In further example, a particle 108 may be a biological cell. A particle 108 may be a genetically engineered biological cell or a descendant of a genetically engineered biological cell. A particle 108 may be a cell that is treated with biomolecules and/or synthetic molecules. A particle 108 may be a cell that is treated with linker molecules. A particle 108 may be such a cell that is treated with biomolecules and/or synthetic molecules that attach to the linker molecules. A particle 108 may be a cell with a fluorescent or luminescent label molecule(s) covalently or non-covalently attached to it or integrated with it. A particle 108 may be a cell with a combination of different fluorescent or luminescent label molecule(s) covalently or non-covalently attached to it or integrated with it. A particle 108 may be a cell with a nanoparticle(s) covalently or non-covalently attached to it or integrated with it. A particle 108 may be a cell with a magnetic nanoparticle(s) covalently or non-covalently attached to it or integrated with it. A particle 108 may be a cell with a fluorescent nanoparticle(s)

covalently or non-covalently attached to it or integrated with it. A particle 108 may be a cell that naturally expresses or is genetically altered to express fluorescent protein(s). A particle 108 may be a cell which is coated with antibodies, proteins, or other molecules or materials.

Substrate Surface Preparation

In one embodiment consistent with the present invention, the sample 107 of particles 108 may further be modified by introducing reagents or non-reactive solutions onto the sample holder 105—before, during or after the measurements. For example, as shown in FIGS. 1A-1C, for the measurement of the surface interactions of the cells/particles 108, the transparent surface 109 (e.g., coverslip) of the sample holder 105 onto which the cells/particles 108 settle, may be provided with special treatment. Thus, the sample 107 disposed on the sample holder 105, may include a dispersion of particles 108 (i.e., cells) disposed on a treated or untreated transparent surface 109 (i.e., coverslip). The sample 107 of cells/particles 108 may be introduced into the sample holder 105 manually or through an automated fluidic device 116 (discussed later), the structure and operation of which is well known in the art.

The particles 108 may settle on the surface 109 to test particle-surface interaction. In one embodiment, the particles 108 may settle on the surface 109 due to gravitational forces. In another embodiment, the particles 108 may settle on the surface 109 due to centrifugal forces applied to a sample chamber 118 by a centrifuge (see FIG. 1F, for example). Further, in another embodiment, the particles 108 may settle on the surface 109 due to other forces applied to the particles 108 (discussed further herein).

In one embodiment consistent with the present invention, a centrifuge may be used to centrifuge the particles 108 (i.e., red blood cells) onto the surface 109 of the substrate 200, forming a more dense coating. FIG. 27 shows screen shots of two slides under microscope, with the particles (i.e., red blood cells) being deposited under centrifuge at 1 g and 400 g (gravity), respectively, according to one embodiment consistent with the present invention.

Figure 28:
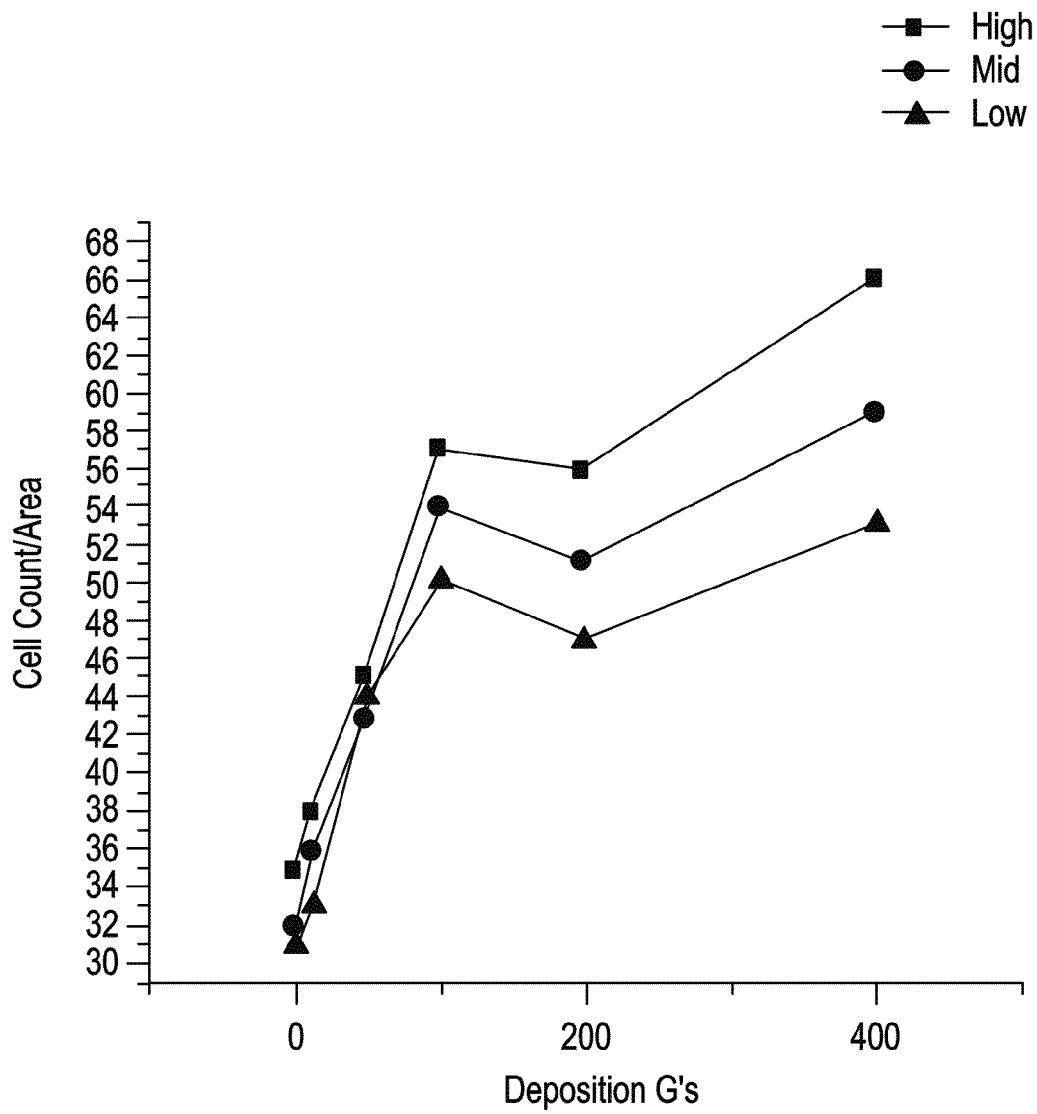
FIG. 28 is a graph showing the high, mid, and low data points which represent different ways of counting particles (i.e., red blood cells) per unit area, under centrifuge at 0-400 G's for five minutes, according to one embodiment consistent with the present invention.

FIG. 28 is a graph showing the high, mid, and low data points which represent different ways of counting particles (i.e., red blood cells in antibody screening) per unit area, under centrifuge at 0-400 G's for five minutes, according to one embodiment consistent with the present invention. From the graph, it can be seen that the trends are basically identical regardless of the method of counting. This embodiment has application to solid-phase blood typing.

The surface 109 may be provided in a variety of ways. In one embodiment, the surface 109 may be flat and transparent. Further, a surface 109 may be flat and partially transparent. Still further, a surface 109 may be a flat and fully or partially reflective. A surface 109 may also be a textured flat surface. A surface 109 may be treated with biomolecules or synthetic molecules. A surface 109 may be treated with linker molecules. A surface 109 may be treated with biomolecules or synthetic molecules linked to the linker molecules. A surface 109 may be differentially treated with a variety of molecules. A surface 109 may be differentially treated with a variety of linker molecules. A surface 109 may be treated with a mixture of molecules. A surface 109 may be part of a microfluidic device 116 (see FIG. 1F, for example). A surface 109 may be part of a microtiter plate or other device with one or more wells or chambers. A surface 109 may be part of a transparent or partially transparent sample chamber 118 (see FIG. 1F, for example). A surface 109 may be part of a reflective or partially reflective sample chamber 118 (i.e., reflective or partially reflective surface). A surface 109 may be sufficiently microscopically smooth to allow imaging of particles 108. A generally planar array of capture surface regions in a sensing array 200 (see FIG. 3) may also simplify optical detection.

Figure 1E:
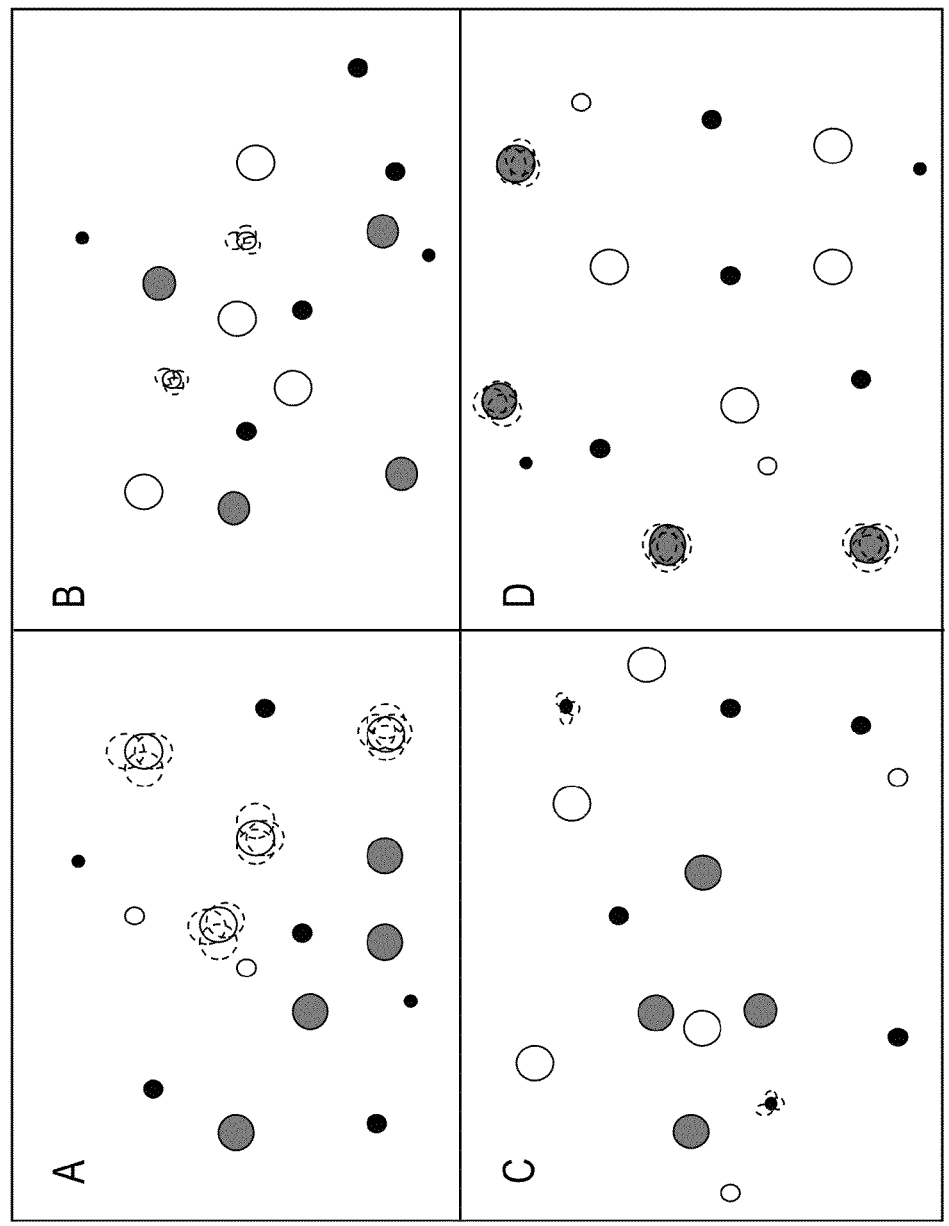
FIG. 1E is a schematic diagram of a top-down view of differentially treated surface areas of a sample holder surface, which each have a heterogenous mixture of particles, where each type of particle yields a differing interaction with the surface as observed through the mobility measure of the heterogenous population of particles.

In one example, FIG. 1E shows a top-down view of differentially treated surface areas (A, B, C and D) of a coverslip which each have a heterogeneous mixture of particles 108, where each type of particle 108 is distinguishable (by fluorescent label or holographic image characteristics, for example). Note that each surface 109 yields a differing interaction (i.e., different types of particles 108 exhibit higher mobility in each area) with respect to the mobility measure of the heterogeneous population of particles 108. FIG. 1E demonstrates how many different types of interactions may be probed simultaneously (i.e., multiplexed measurements) by using a distinguishable heterogeneity of particles 108 with or without differentially treated surface 109 areas, in accordance with the present invention.

Sample

In one embodiment, a heterogeneous population of particles 108 may be measured simultaneously, with each type of particle testing for different quantities or regimes in similar quantities (e.g., multiplexed measurements). All or some types of particles 108 may be distinguished based on a label (e.g., fluorescent, nanoparticle), particle image (due to different absorption, scattering, fluorescence, luminescence characteristics, fluorescence or luminescence emission profiles, fluorescent or luminescent decay lifetime, and/or particle position etc. (assuming controlled deposition of particle types)). All or some types of particles 108 may be distinguished by a multimodal collection of data of each particle 108. A homogenous population of particles 108 may be measured simultaneously.

In one embodiment, the sample 107 which includes particles 108 coated with biomolecule A, contacts the surface (i.e., solid-phase) which is coated with biomolecule B. The sample 107 solution may contain biomolecule A and may contain or not contain other types of biomolecules (e.g., biomolecule C, D, E, etc.). The sample measurement of this method yields information of biomolecular interactions between the particles 108 and the surface 109 in the presence of the solution for research, industrial and/or clinical purposes by an analysis of particle mobility in response to controlled or thermal forces.

In one embodiment consistent with the present invention, concerning a blood typing application, the particles 10 are cells/beads 108 with surface antigens which may be bound to a diffusing moiety present in the solution. Furthermore this moiety may simultaneously be able to bind to an appropriately treated surface (solid-phase). In this manner, the presence or quantity of the moiety in solution may be measured by measuring the mobility of appropriately coated particles 108 on appropriately treated surfaces 109 (solid-phase). The presence of such diffusing species may affect the mobility of the bound cells/beads 108 in a concentration-dependent way. This type of measurement may be used to determine the presence, absence and/or concentration of the freely diffusing target moiety which acts as a capture agent for the particles.

In the blood typing exemplary embodiment, if particular antigens are probed on the cell/particle surface, an appropriate surface treatment for the transparent surface 109 may include chemically modifying the surface 109 with a suitable linker molecule to be able to attach the appropriate antibody to the surface 109, to allow specific binding of the cell/particle 108 presenting the target antigen with the surface antibody on the transparent surface 109. Cells/particles 108 that do not have the target antigen on their surface 108a do not specifically bind to the surface of the transparent surface 109, in this case. In the case of measuring cell/particle 108 diffusional properties (e.g., effective diffusion coefficient, effective viscosity or visco-elasticity properties), for example (discussed later), an inert surface 109 could be used.

In one embodiment, when the particles 108 are coated or otherwise have embedded fluorescent, or luminescent molecules or nanoparticles, which are distinguished by particle type based on fluorescent or luminescent emission spectrum, the microscopy apparatus 10 shall be equipped with a fluorescent, luminescent excitation source, appropriate filters and dichroic elements as well as color detection capabilities (e.g., color camera 112 and/or emission filter selections). The introduction of different types of particles 108 with each type being uniquely coated may allow multiplexing the measurements (i.e., measurement of multiple types of interactions simultaneously). Unlike in many traditional fluorometric multiplexed measurements, a separate washing step is not needed, since it is not the presence of a given particle 108 that marks a positive binding interaction, it is the mobility measurement of particle that indicates positive binding.

Sample Holders and Fluidic Devices

The following, along with the instrumentation described earlier, are the means for determining a mobility of the particles in the sample.

Embodiment 1

In one embodiment consistent with the present invention, the sample holder 105 includes a simple microscope slide made of glass or plastic, with the particles 108 being disposed or settled on its transparent surface 109 (see FIGS. 1A-1C). Typically a cover slip will be placed over the sample.

Embodiment 2

In yet another embodiment consistent with the present invention, the transparent sample holder 105 includes a simple passive microfluidic cartridge 116 (see FIG. 1F). In this embodiment, the closed sample microfluidic cartridge 116 includes two ports (i.e., inlet 401, outlet 402) and a chamber 118 therebetween (see drawing A). A sensing array 200 is bonded underneath with capture surface regions 210, 211, 212, and is treated with the appropriate chemistry for the particular application desired. The sample solution 107 of particles 108 is introduced into the inlet 401 and the particles settle onto the surface 109, and capture surface regions 210, 211, 212 of sensing array 200 (see drawings B-D). Binding interactions may be observed using the microscopy apparatus 10.

Embodiment 3

In yet another embodiment consistent with the present invention, the transparent sample holder 105 includes a well plate (standard microtiter plate or custom well plate or other cartridge with wells). In this embodiment, the open well sample cartridge 161 includes a transparent sample holder 105 with an opening in the center for a chamber 118 (see FIG. 1G, drawing A). A cover glass 162 is bonded underneath. The cover glass 162 will be treated with the appropriate chemistry for the particular application desired. A cap (like cap 417 in FIG. 1H, for example) may be disposed over the opening to the chamber 118. A sample solution 107 of particles 108 is disposed in the chamber 118 and settles on the surface 109, including capture surface regions 210, 211, 212 (see FIG. 1G, drawings B-C), and binding interactions may be observed using the microscopy apparatus 10.

Embodiment 4

In another embodiment consistent with the present invention, the microtiter plate of Embodiment 3 or suitable alternative with wells, may or may not have a customized configuration, including optically transparent caps, sample delivery zones, sample viewing zones etc. For example, the microtiter plate or alternate cartridge with wells may be an open-well disposable with a cap or a lid. In particular, a cap 417 may be used with a microfluidics well plate 416 (see FIG. 1H) to allow the present invention to be performed therewith. The cap 417 is disposed in a well 418 to provide a top surface during certain incubation and/or measurement steps. Optionally, gaskets 450 may be used to create a seal between the cap 417 and the well plate or other cartridge with wells 416. Seals may also be formed at positions 451 or other positions, for example, to keep the cap 417 in place, and an overflow reservoir 452 allows excess solution to have a place to go when displaced from the well chamber 118.

Particles 108, such as probe red blood cells, are disposed in the bottom of the well 416. The cap 417 in the well 418 defines a fixed space (approx. 100 microns, for example) between the capture surface region 210 etc., and the bottom surface of the cap 417 which forms the well chamber 118 ceiling. The benefit of the cap 417 being disposed in the well 418 is that the fluid height is very short and thereby: 1) allows the sedimentation of particles/RBCs 108 to occur very quickly, 2) suppresses three-dimensional flows which may interfere with sedimentation, binding, or measurement, 3) eliminates or minimizes the free surface where evaporation can occur and where vibrations may induce surface waves and bulk convection, 4) suppresses unintended flow of the fluid during manual or robotic movement of the microfluidics plate, and other important benefits.

Embodiment 5

In another embodiment consistent with the present invention, a simple microfluidic sample cartridge 116 includes an inlet 401 for one or multiple solution, and an outlet 402 (see FIG. 1F, drawing A, for example). The microfluidics cartridge 116 is made by cutting two thin sheets of plastic with the top layer having two openings for said inlet 401 and outlet 402, and a center opening 118 for a sample chamber. The second layer will have a pattern thereon, with channels entering the center chamber 118. The two layers are bonded together and a cover glass 200 with the appropriate chemistry thereon, is bonded underneath. Solution is added to the inlet opening 40 and flows through the channels to the middle sample chamber 118 where it contacts the cover glass 200 with capture surface regions 210-212, and to the exit channel and outlet 402. If the appropriate amount of fluid is introduced, the solution flows by itself and stops when it arrives inside the chamber 118 or arrives at the outlet 402. Alternately, the fluid may be actively pumped through the device.

Embodiment 6

Figure 3:
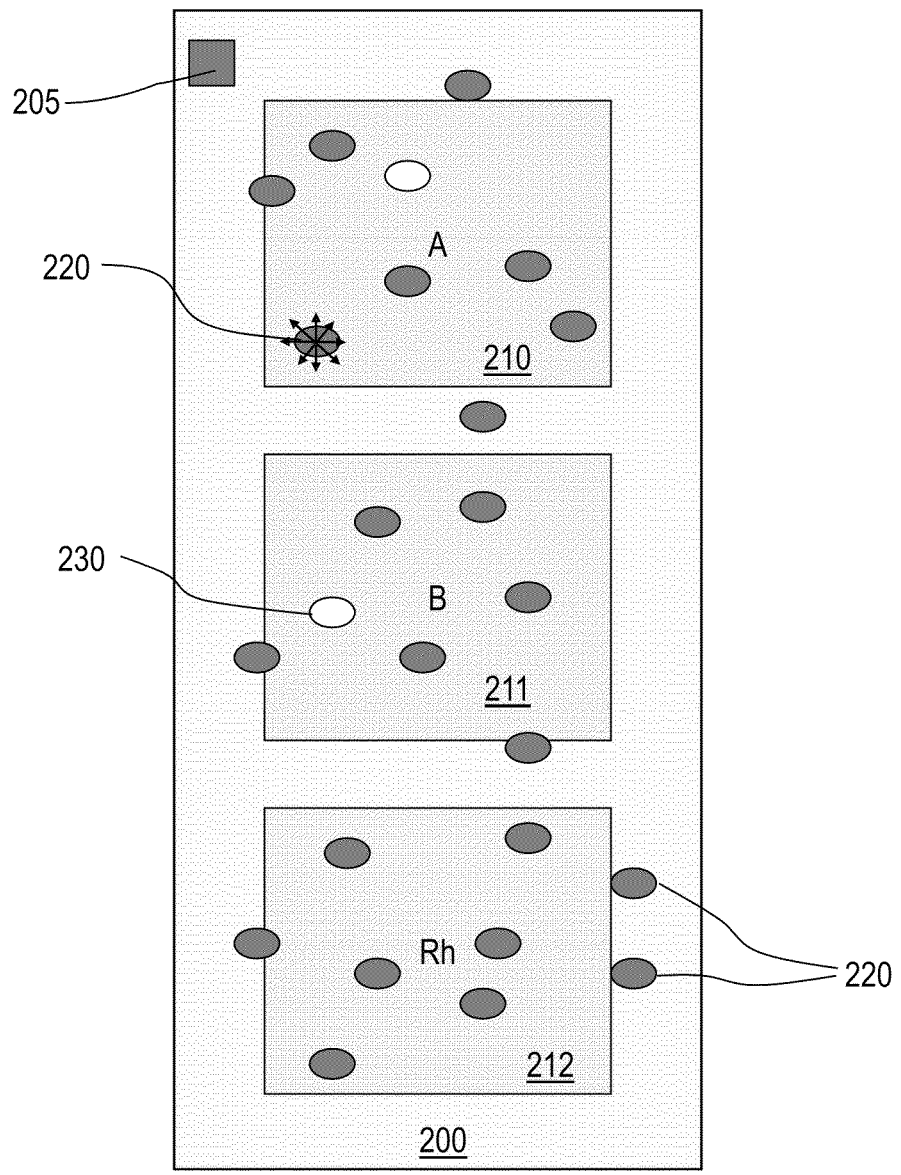
FIG. 3 is a schematic diagram of a sample holder or substrate of a microfluidics device, including a sensing array with particles disposed on multiple capture surface regions, according to one embodiment consistent with the present invention.

In another embodiment consistent with the present invention, a microfluidic sample cartridge 116 includes three regions 210, 211, 212 on the cover glass or substrate 200, which are functionalized for a binding experiment (i.e., has three capture surface regions 210, 211, 212) (see FIG. 3, for example). This is the example used for blood typing experiments discussed further herein.

Additional Embodiments

The microfluidic cartridge may be an automated fluidic device or a well-type device, each being compatible with data acquisition and analysis (i.e., microscopy apparatus 10), as described herein. The particles 108 are flowed into the sample chamber 118 of the microfluidic device, or introduced into the well device by a robotic pipeting apparatus which introduces a number of samples 107 (particles 108, with solution) into different wells. In the well device, each well may have a unique surface chemistry, indexed by position, allowing multiple tests to be performed, such as independent binding assays, ultimately allowing a single sample 107 (or a plurality of samples 107) to be tested with a plurality of surfaces 109.

The instrumentation outlined herein may be integrated with a robotic machine for automated (and parallelizable) fluid delivery from sample containers to each well, sample mixing and incubation capabilities, as well as parallelized measurement capabilities, which may be programmable and automated. Thus, an assay may be designed to perform multiple tests on one or a number of samples 107, in a parallel fashion. In addition, multiple microfluidic or well devices may be measured in a parallel fashion with a suitably parallelized optical train and detection set-up. A robotic apparatus may feed microfluidic or well devices into the detection area for measurement in an automatic fashion, allowing many samples to be measured without user intervention.

Measurements in a given sample chamber, microfluidic sample chamber or well device, may be repeated after the addition of solutions, particles or mixtures, or the exchange of solutions, particles or mixtures, and/or incubations at different temperatures.

Titration measurements may be performed in a given sample chamber, microfluidic sample chamber(s) or cartridge well(s) by introducing additional analytes into the chamber/well solution(s).

Further, kinetic experiments may be performed in a given sample chamber, microfluidic sample chamber(s) or microtiter plate well(s) by following the time-course of the particle mobility measurements (e.g., normal standard deviation (NSD), discussed further herein). This may be done with or without the introduction of additional analytes into the chamber/well solution(s).

Disposables and Instrumentation

Figure 24:
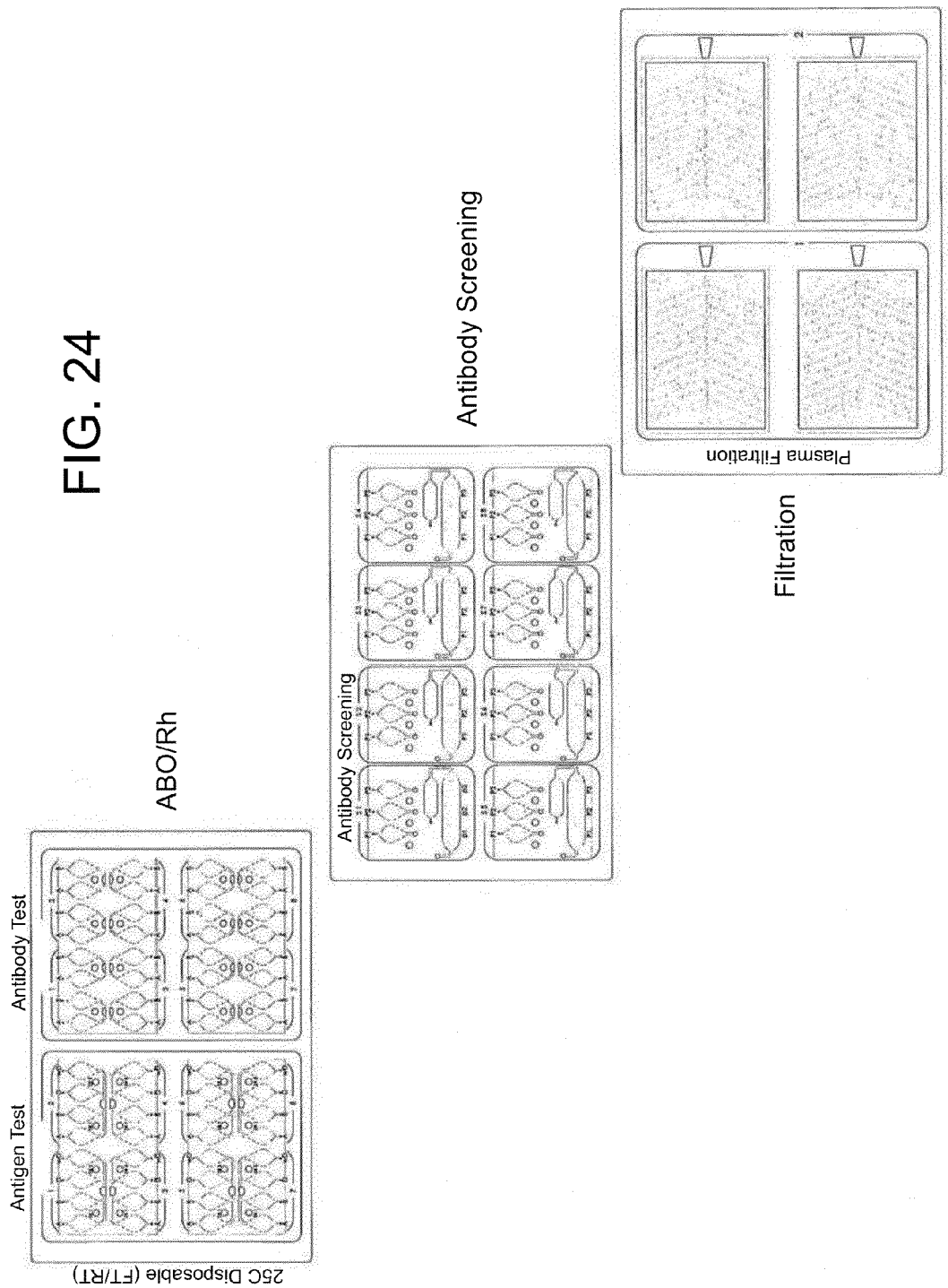
FIG. 24 is a top plan view of a schematic illustration of disposables used to perform immunodiagnostic tests according to embodiments consistent with the present invention.
Figure 25:
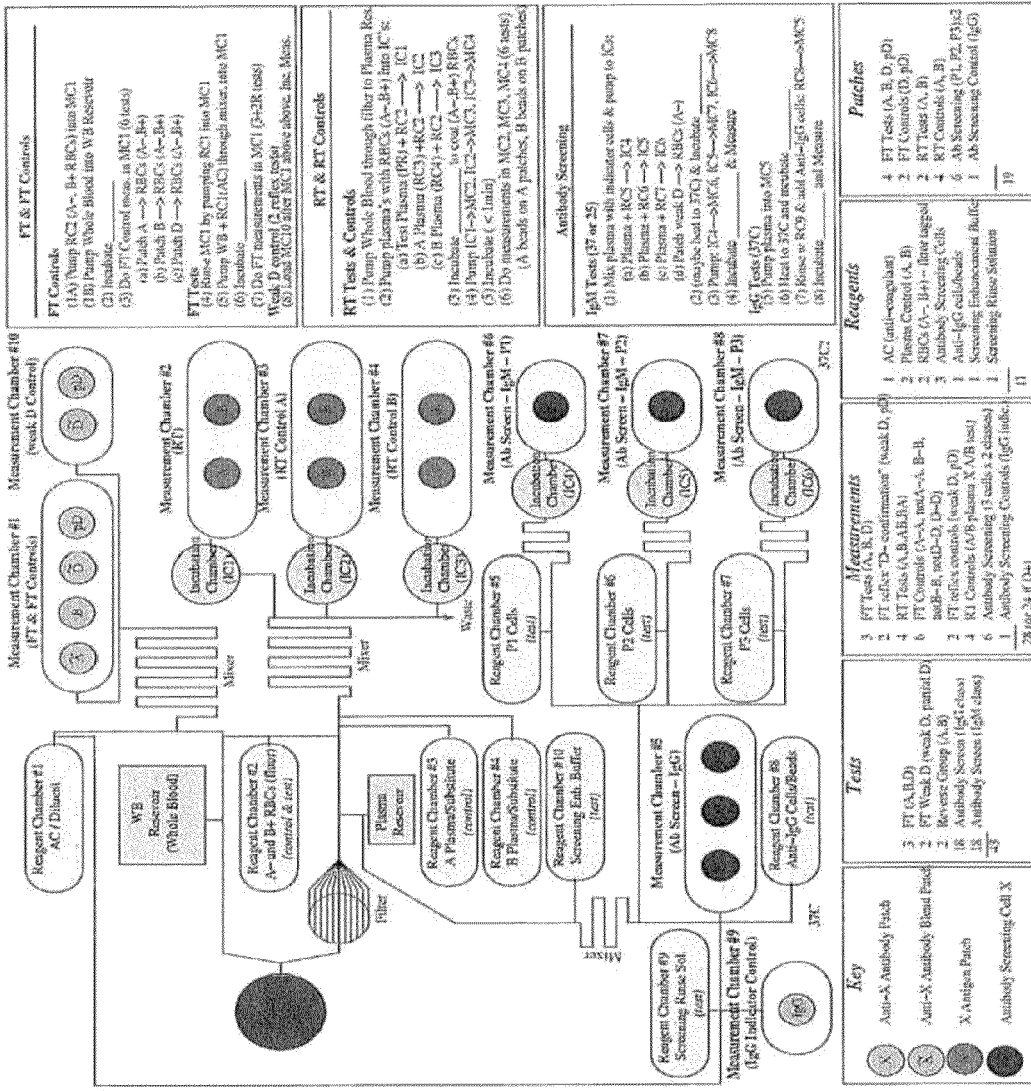
FIG. 25 is a flow chart showing the process steps involved in carrying out blood type testing.

The chip design according to one embodiment consistent with the present invention, encompasses a disposable cartridge for immunodiagnostics, for example, on which ABO/Rh blood typing, Antibody Screening, and Plasma filtration or separation, can be performed, in addition to Weak D antigen, Extended Phenotyping, Direct Antiglobulin Test (DAT), and Antibody Identification may be performed (see below for further explanation of these Applications). The disposable designs are shown in FIG. 24, which shows an ABO/Rh cartridge for forward typing and reverse grouping blood testing (8 samples), a cartridge for Antibody Screening (8 samples), and one for Filtration (2 samples). The flowchart of FIG. 25, shows an overview of the process steps for forward typing, forward typing controls, reverse grouping, reverse grouping controls, antibody screening, and antibody screening controls. These process steps may be performed in a variety of configurations including active disposables or simple passive disposables as shown. The testing itself shown in the flowchart, is explained further below with respect to the Applications of the present invention. While only one set of process steps are shown, there are many ways to alter these process steps to achieve similar results or to optimize for certain performance or other characteristics.

Figure 26:
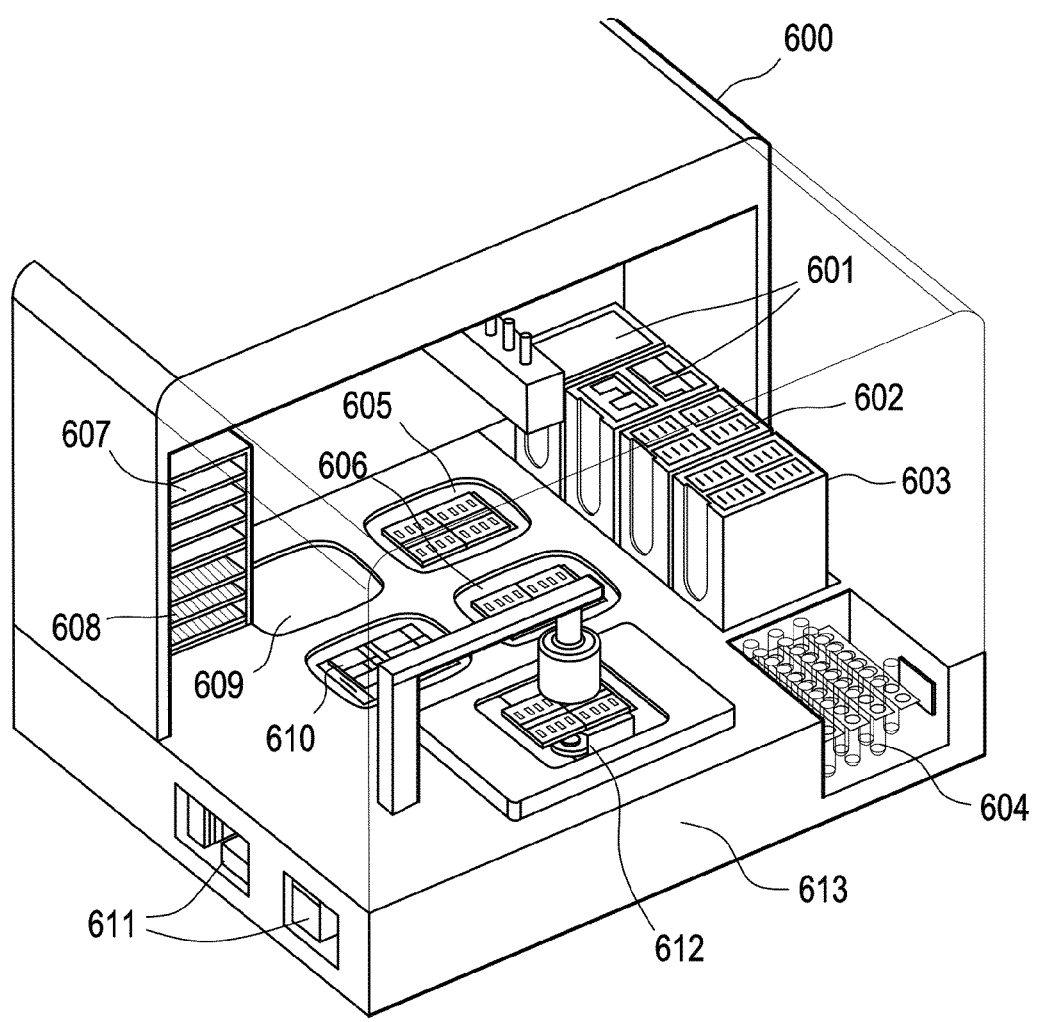
FIG. 26 is a perspective view of an instrument according to one embodiment consistent with the present invention, in which the disposable of FIG. 24 are inserted.

The instrument 600 in which the Filtration disposables 601, ABO/Rh disposable 602, and Antibody Screening (AbS) 603 disposables, are inserted for testing, is shown in FIG. 26, according to one embodiment consistent with the present invention. The disposables 601, 602, 603 are inserted into specified areas, and the instrument 600 can accommodate 80 cartridges of Filtration disposables 601 (160 samples), 100 cartridges of ABO/Rh disposables (800 samples), and 100 cartridges of AbS disposables (800 samples).

The instrument 600 has a section for tube racks (with barcode reader) 604, a pipetting station for stat tests 605, a pipetting station for non-stat tests 606, a 37° C. incubation area 607, a 25° C. incubation area 608, a stat filtration station 609, a non-stat filtration area 610, a snap-in liquid cartridge area 611, an illumination area where the testing is performed 612, and a reader for reading the results 613.

The instrument 600 of the present invention is fully automated and computer controlled, and accepts whole blood tubes and vials (see tube racks 604), and does not require manual reading of the results like conventional tests. Further, the present invention disposables do not require centrifuged blood as input (and thus, no external centrifugation since it separates plasma from whole blood on one of the disposables), and has some reagents and optionally some controls in the disposable itself. Thus, whatever processing is necessary, such as plasma extraction, solution mixing, and cell dilution, is all done by the combined computer-controlled instrument and disposable, and without user interaction.

A single test takes 10 minutes and batches of 12 tests can be performed per hour. Thus, with the disposables used with the present invention, applications such as blood typing and screening, can be performed much faster than conventional methods.

Activated Methods and Apparatuses

There are several embodiments consistent with the present invention, which provide activated methods which are used for applying forces to the translation stage 114, particles 108, or fluid surrounding the particles 108, in order to determine whether binding interactions occur. In particular, the physical force application means includes an abrupt or continuously periodic movement of the translation stage 114, particles 108, or fluid surrounding the particles 108, using external activating means such as any of the following.

a) Pneumatic/Hydraulic Pressure Oscillator

FIG. 2A shows a disposable measurement chamber 118 of a microfluidics device 116, with an inlet 401 and an outlet 402, connecting to an exemplary pneumatic or hydraulic pressure pump 117 which includes high and low pressure sources 403, 404, respectively. Solenoid valve(s) 405 produce a series of pneumatic/hydraulic pressure pulses to the sample 107 in the chamber 118 at a given frequency.

Figure 23:
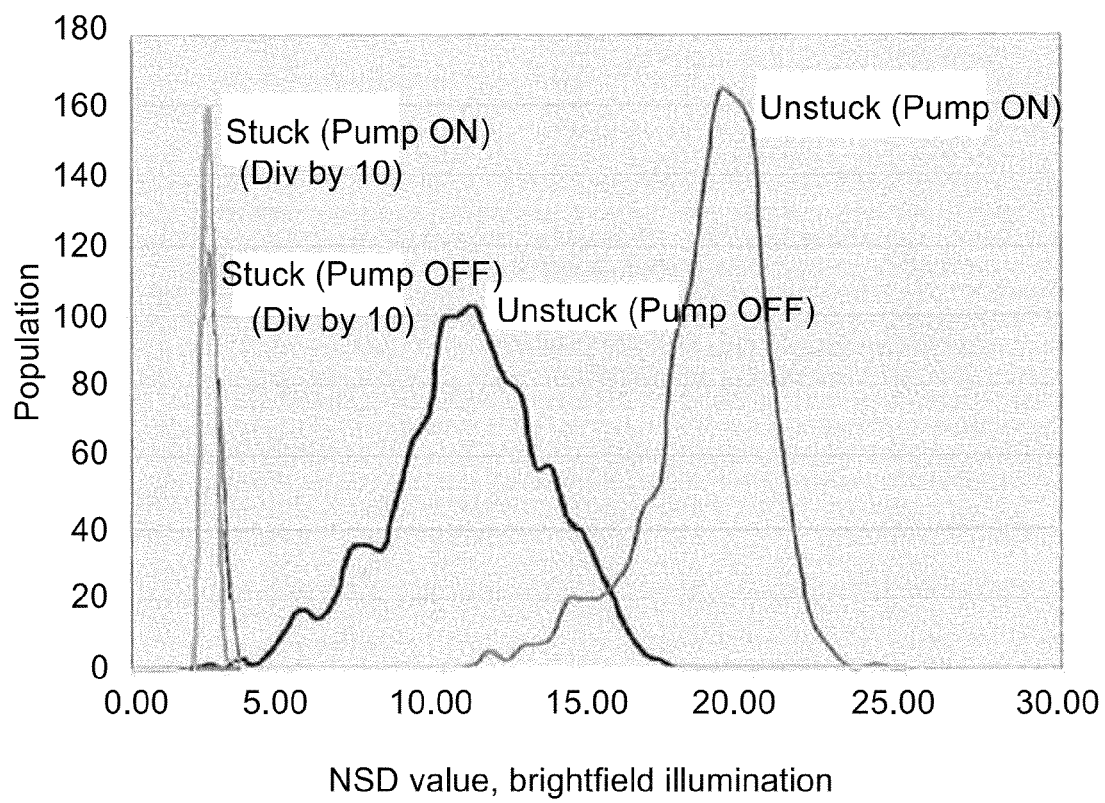
FIG. 23 is a graph of the distribution of bound and unbound particles, according to one embodiment consistent with the present invention, showing the distribution of normalized standard deviation measurements as measured with brightfield illumination using both thermal activation as well as using activation with an instrument as in FIG. 2A.

In an experiment conducted under brightfield illumination, with a 4× magnification objective lens, freely-diffusing or bound silica beads (4.8 μm) were suspended in water inside a chamber 118, across which an oscillating pressure differential was applied. The oscillating pressure differential gently perturbs the fluid surrounding the particles 108, resulting in a net force on the particles 108 which is greater than random thermal forces, thus, resulting in a greater difference in the behavior of bound and unbound particles 108. As shown in FIG. 23, the distribution of measured normalized standard deviation (NSD) values for activated unbound beads has a higher mean and narrower width, whereas for the bound beads it is largely unchanged (see below for further explanation of NSD methods). The tails of the distributions of bound and unbound overlap somewhat without activation, while with the activated sample there is a large space which separates the tails of the two distributions. Thus, the bound beads can be more easily and reliably distinguished from the unbound beads. In situations where measurement uncertainty or noise may be a concern, this amplified signal can greatly improve confidence level.

b) Piezoelectric Hydraulic Actuator

Figure 2B:
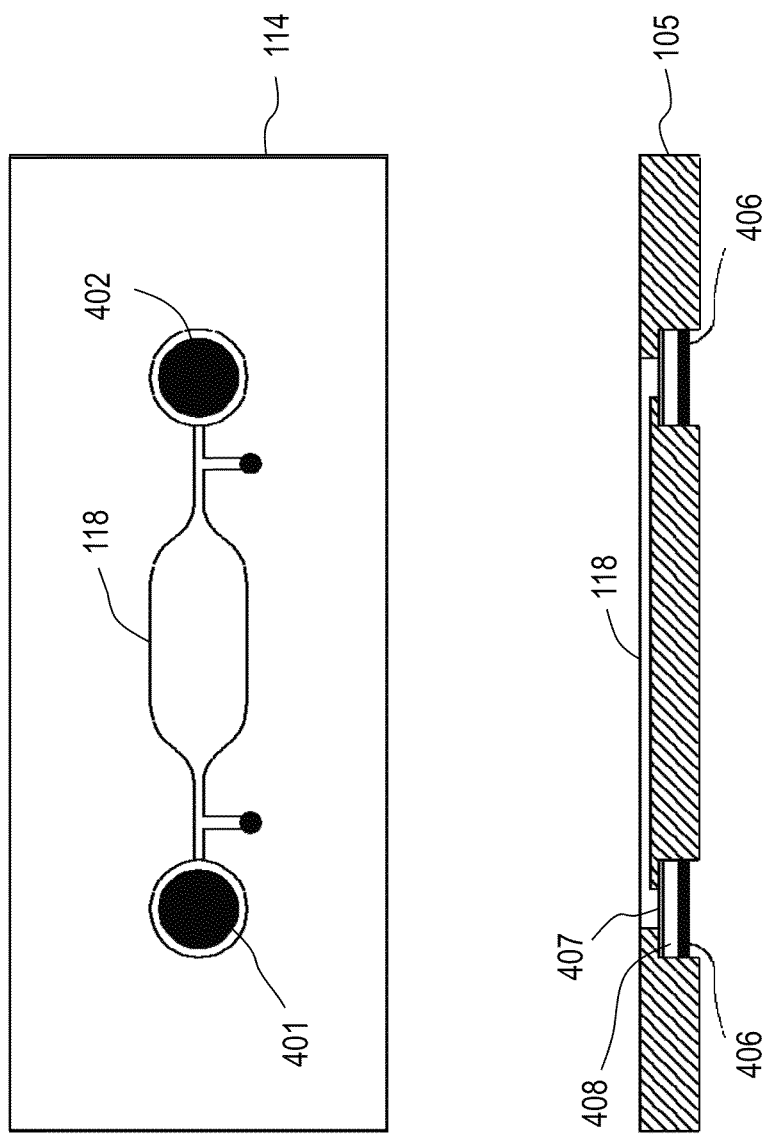
FIG. 2B shows a schematic diagram of a microfluidics device with an exemplary piezoelectric-hydraulic actuator, according to one embodiment consistent with the present invention.

FIG. 2B shows a disposable measurement chamber 118 of a microfluidics device 116, with an inlet 401 and an outlet 402, connecting to an exemplary piezoelectric-hydraulic actuator 406 to produce oscillatory flow to the sample 107 in the chamber 118 at a given frequency and amplitude. A diaphragm membrane 407 may optionally use a hydraulic oil or gaseous media 408 which allows the peizoelectric-hydraulic actuator 406 to actuate.

c) Piezoelectric Stage Oscillator

Figure 2C:
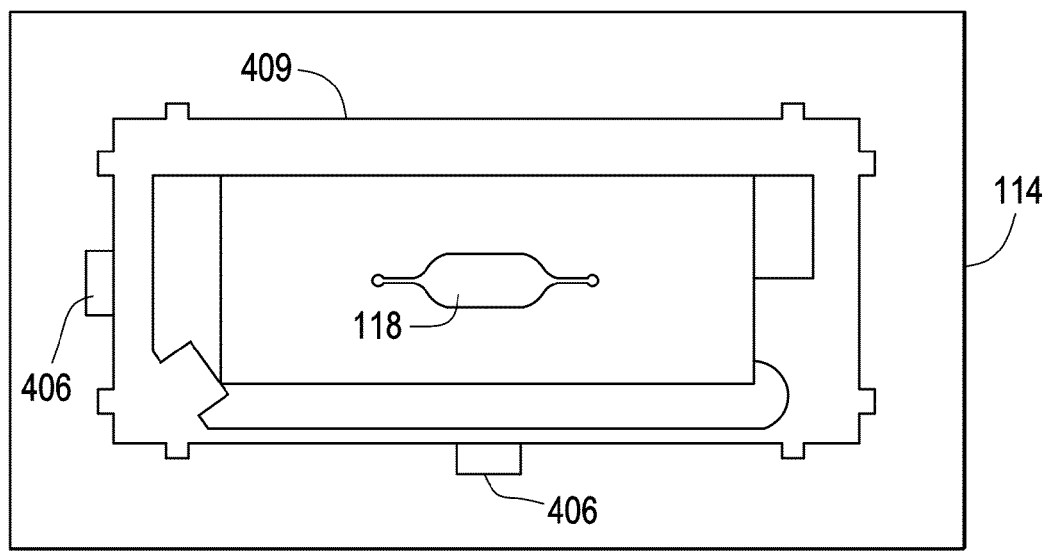
FIG. 2C shows a schematic diagram of a microfluidics device connected to an exemplary piezoelectric stage oscillator, according to one embodiment consistent with the present invention.

FIG. 2C shows an exemplary piezoelectric stage oscillator including a translation stage insert 409 attached to the piezo actuators 406 which can convert control signals into oscillatory motion of the insert 409. The movement of the insert 409 then becomes transferred into periodic motion of the particles 108 inside the measurement chamber 118.

d) Pneumatic or Hydraulic Valving/Perturbation

FIG. 2D shows an exemplary pneumatic or hydraulic valving/perturbation device where an on-chip diaphragm membrane 407 is driven by pressurized or vacuum system(s) through pneumatic/hydraulic control line(s) 411 and port(s) 412. A membrane valve 413 includes the diaphragm membrane 407 which is moved to valve or pump the sample 107, causing flow.

e) Thermal Actuator

FIG. 2E shows an exemplary thermal actuator which contains heating element(s) 414, diaphragm membrane 407 and gaseous material (or other high thermal expansion material) 408 sealed in between. The volume of the thermoloid material can change significantly when the temperature increases or decreases, thus moving or retracting the membrane 407 to oscillate the sample 107 inside the measurement chamber 118.

f) Acoustic Radiation

FIG. 2F shows an exemplary acoustic source 415 (i.e., sonic or ultrasonic emitter) which propagates an acoustic wave through the measurement chamber 118, causing periodic oscillating movement of the sample 10 or fluid surrounding the sample inside the chamber 118. This may be done as shown, or with alternate orientations of the acoustic source relative to the sample 107. For example, the acoustic source 415 may be placed along the other side or the top of the sample 107. The system may be driven in such a way as to set up standing wave patterns, so as to avoid standing wave patterns, or so as to have sweeping standing wave patterns which go through a variety of states over time or at once by emitting at multiple or numerous frequencies at once.

g) Well Cap Activation

In this embodiment, an "open well sample cartridge" has been designed, which includes a plastic cartridge 116 formed by cutting holes through a sheet of plastic, and bonding a substrate 162 underneath, which has a plurality of patches or capture surface regions 210, etc. (see FIG. 1G, for example). The cap 700 (see FIG. 2G, drawing A) is made from a piece of transparent plastic which overhangs the edges of the well 705. The cap 700 is polished on the top and bottom to provide good optical quality. The bottom of the cap 700 should be a prescribed distance from the top of the substrate 701. This distance should preferably be at least 25 μm, but less than 1 mm. The particles 108 are confined between the substrate 701 and the bottom of the cap 700.

The well cap 700 can be used with a mechanism 704 for sliding the cap back and forth in the well 705. The well cap activation mechanism can be implemented in a variety of ways, including using a linear solenoid actuator 704 (see drawing B), where the well cap 700 is connected via a wire to a solenoid coil (e.g., loudspeaker) driven by a function generator (not shown). A controller 703 controls the current over time (and thus, the forcing over time). A motion guide 702 can be included in the system, to restrict the motion along one linear axis without cap 700 rotation, although other appropriate methods may be used to do so.

In another embodiment consistent with the present invention, the well cap 700 rigidly attaches to a mount and a piezoelectric actuator 704 drives the cap 700 left-right (see drawing C). Any appropriate actuator may be used to achieve more precise movement.

The use of a cap 700 greatly reduces convection, evaporation, sloshing of a fluid during transport, susceptibility to vibrations, non-uniform sedimentation of particles, unintended rolling of particles along the bottom surface (i.e., capture surface regions), and other unwanted confounding effects. The use of a cap also constrains the height of the system, thereby reducing the amount of time over which the particles sediment to the surface, since the faster the particles fall, the sooner they interact with the capture surface regions, and measurements can be taken.

Thus, in either embodiment of the well cap 700, the waveform (a triangular wave is simplest since there is constant velocity over most times), frequency (approximately 1 Hz, within a decade or so), and amplitude (approximately 200 microns, within a factor of 5 or 10), can all be controlled. Thus, the amount of movement as well as the magnitude of the applied forces, can be all controlled. A force can be inputted to discriminate between specific binding (SB) and non-specific binding (NSB)—i.e., if NSB is weaker than SB, one obtains a force which disrupts the weaker NSB bonds and not the stronger SB bonds. Thus, the sample 107 can be jostled to better separate bound and unbound particles/cells 108. This results in making the determination of binding much more robust against measurement noise like focusing, illumination, dust, or defects. Further, because unbound particles move around more when the mechanism 419 is utilized, it helps particles 108 that should have found a binding site during the measurement period, but have not done so, find a binding site on the substrate. This mechanism can also be used continuously or intermittently during the incubation stage, and activation can be performed either during the measurement period, or not.

Although the above embodiments have been described, one of ordinary skill in the art would know there are other activated methods and apparatuses which could be realized in order to apply physical forces to the sample 107 in the measurement chamber 118.

Advantages of these activated methods include: 1) stronger separation between bound and unbound particles; 2) greater robustness against illumination intensity variations, vibrations, slightly out-of-focus particles, imperfections in the flatness of the sample, imperfect leveling of the stage or sample, and other issues which introduce noise into a measurement, 3) potentially actively overcoming nonspecific binding (NSB), by differentiating between NSB and specific binding where NSB may have lower binding strength than the driving force of the activated method, and 4) encouraging faster exploration of configurations between a particle and the substrate, allowing for speedy binding and/or stronger binding—thereby speeding up the test measurements.

Methods

Focusing Background

Prior to conducting the methods of the present invention, focusing of the microscopy equipment may be performed in order to achieve the best results. Achieving a sharp image in a typical light microscope often requires focus precision on the single-micron scale. Lower numerical apertures can give rise to less sharp images and larger depth of focus, requiring somewhat less focus precision, and choice of appropriate algorithms can also reduce tolerances on focus somewhat. However, focus tolerances are still typically on the micron- or tens-of-microns scale.

Traditional focusing techniques require multiple focus shifts, and a comparison of the images acquired at these different focal positions. By applying a focus measure to each image, a determination may be made as to whether the focus shifts are approaching the true focal position or not. In most cases, this can be a slow process given the focus precision required in microscopy applications. Further, the measurement of multiple fields of view, sample chambers, microfluidic chambers, or microtiter well plates, may require multiple refocusing events. The fact that the sample is physically moved multiple times to determine the focus, makes such techniques time consuming. To increase the throughput of such a measurement system, focusing time should be kept to a minimum.

Holographic Focusing

In contrast to traditional microscopy techniques, the use of a coherent source 100B to illuminate the particles 108 allows numerical processing of a single out-of-focus image of the sample 107 to determine the correct focal plane of the particles 108 in a quick fashion (see FIG. 1C). Illuminating the sample 107 of particles 108 in a transparent sample chamber 118, for example, with a coherent source 100B, allows imaging of the particles' 108 diffraction pattern even when significantly out of focus. A numerical solution to focusing allows quick focusing over a long-range of out-of-focus distances. Numerical focusing involves the propagation of the out-of-focus image to different distances which allows the focus to be determined numerically. By associating a focus measure with each numerically propagated image, an extremum in the focus measure may be found, allowing a single stage movement to position the sample in the required focal position. This is in contrast to the traditional focusing methods which require comparatively slow physical scans of a sample through different focal distances to determine the focal position according to some focus measure.

Thus, the acquired out-of-focus diffraction pattern may be numerically propagated over a range of distances to determine the distance that maximizes the focus measure (see W. Li et al., J. Opt. Soc. Am. A, Vol. 24, No. 10, 3054-62, 2007, for example). Once this distance is numerically determined, a single stage movement may be performed to position the sample 107 to the required focal position.

A dedicated focusing camera (not shown) may be used in acquiring images upon which the numerical propagation calculations are performed. In one embodiment, this camera may be placed at an imaging plane different to that of the camera 112 used for mobility measurement. Thus, focusing calculations are performed from images collected from this separate focusing camera which is positioned in a plane that is out-of-focus compared to the measurement camera 112.

It is also possible to use a single camera 112 for both focusing as well as mobility measurement. An image for focusing purposes may be collected after controlled defocusing of the sample 107.

Figure 10:
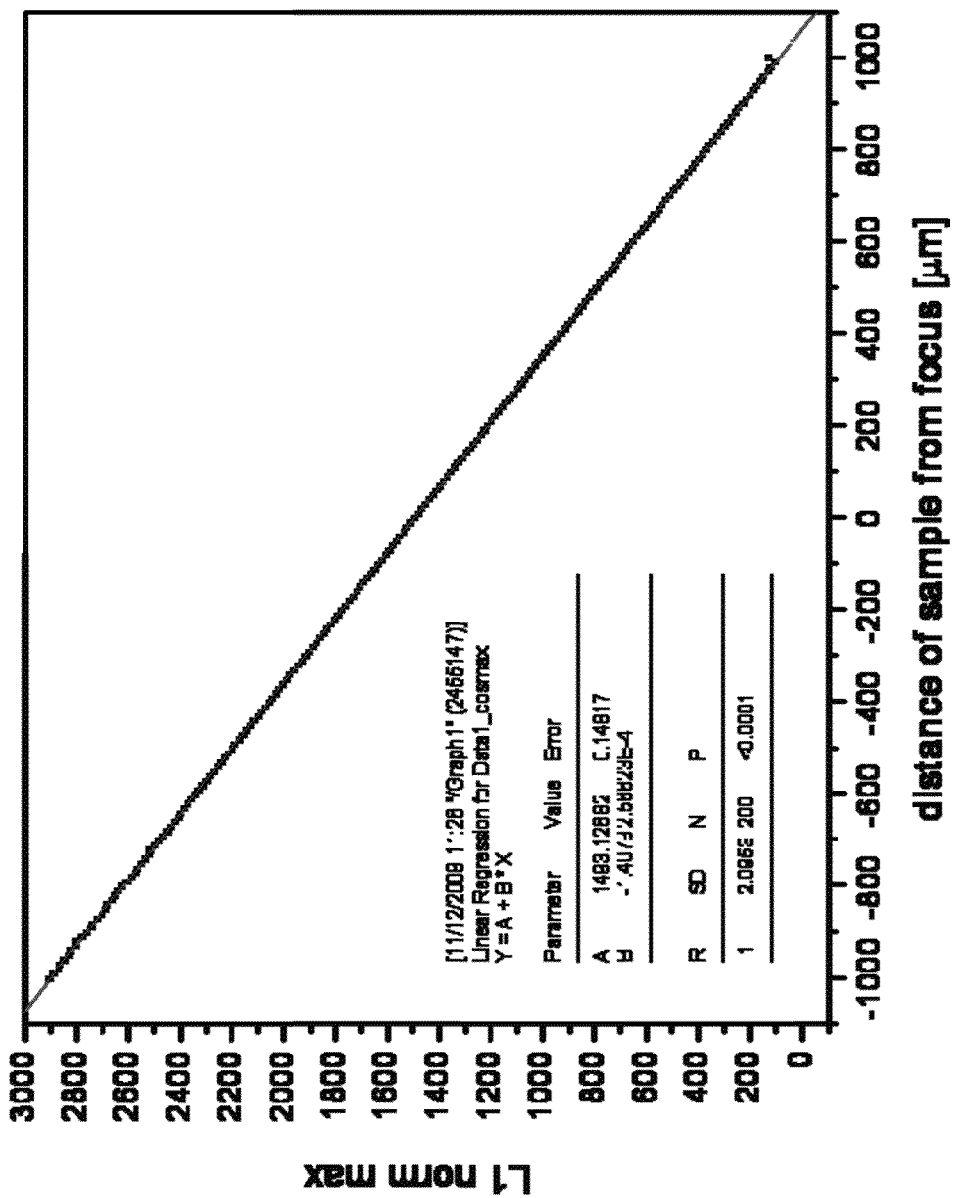
FIG. 10 illustrates a calibration curve of the coherent illumination "L1 norm" method for calculating the out-of-plane z position of the best focus for a sample which predominantly is located in a certain z plane, according to one embodiment consistent with the present invention.

FIG. 10 illustrates a calibration curve generated from numerically propagating images from a calibration sample 107 (see FIG. 1C) that was scanned from 1 mm above the true focus position to 1 mm below the true focus position. The images were collected on a dedicated focusing camera that was displaced 1 mm away from the focus position. The objective lens 142 used had a low-magnification and low-numerical aperture objective. Calibration curves may also be generated with different objective lenses 142 and CCD positions as well. The x-axis of the calibration curve shows the actual distance the calibration sample 107 was moved, with respect to the focal position, and the y-axis value indicates the location of the peak of the focal measure of the numerically propagated out-of-focus image. For samples 107 that are defocused significantly far from the focal position, more than one numerical focus iteration may be required to attain the desired focusing accuracy. More generally, more than one refocus step may be employed to ensure the desired precision, especially in cases where a medium interface (e.g., an air-glass interface or glass-water interface) occurs between the true focus position and the out-of-focus position.

Figure 11:
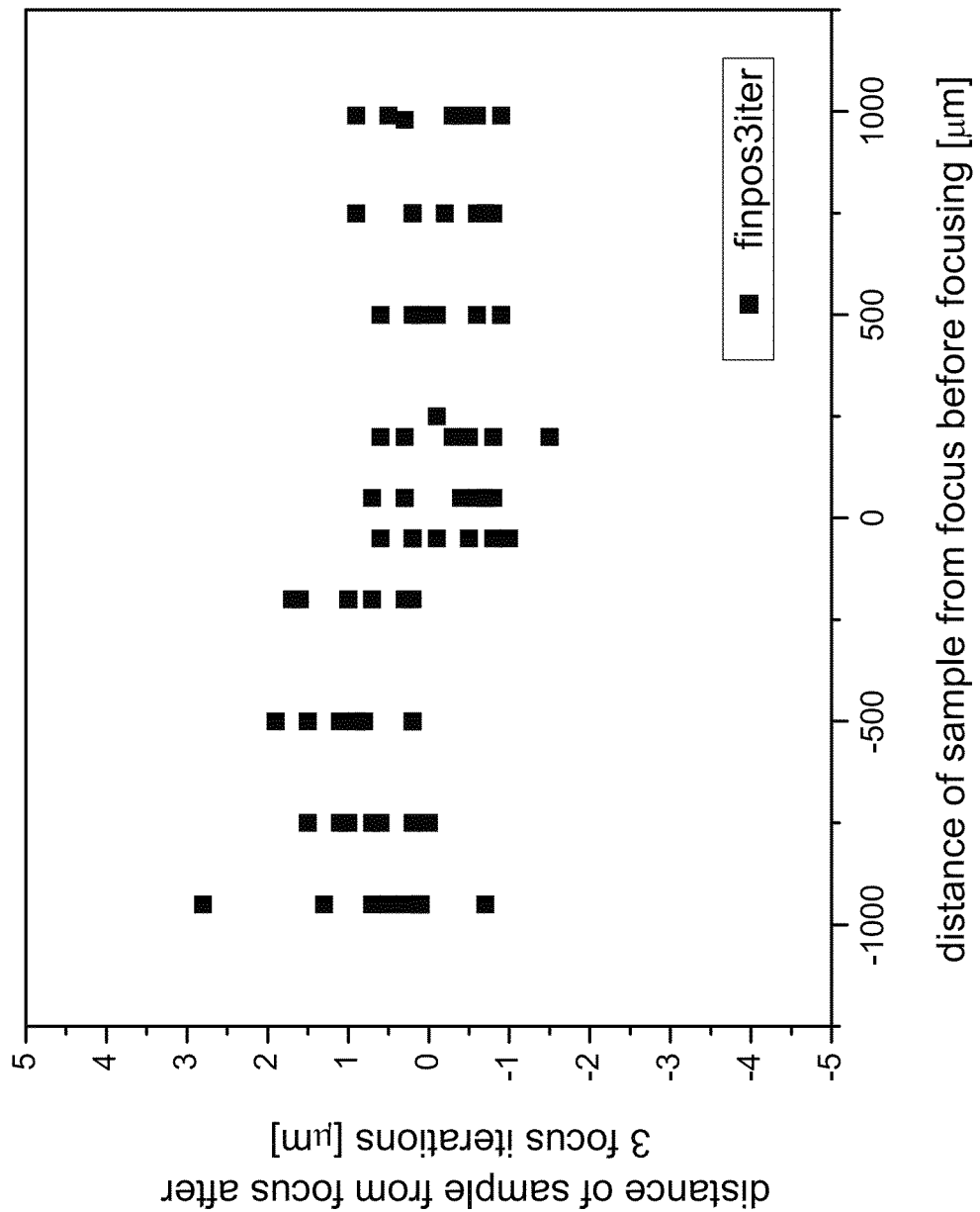
FIG. 11 illustrates the focusing performance using the calibration curve of FIG. 10 when three focusing iterations are performed for a range of initial starting positions, according to one embodiment consistent with the present invention.

FIG. 11 illustrates the focusing performance using the calibration curve of FIG. 10 when three focusing iterations are performed for a range of initial starting positions ranging from +1 mm to −1 mm. The true focal position was determined visually and has an error of approximately ±1 µm. The values of the final position with respect to the focal-plane are accurate to within the estimated error of the visually determined focal position measurement.

Settling

The methods of performing the present invention on the apparatuses described above, include introducing a population of microscopic particles into a chamber and settling the particles on a surface in order to measure any binding interactions.

The present invention may employ various systems to settle the particles 108 on the substrate 200. They include gravity, centrifugal, flow-based, diffusion-based, magnetic, and holographic tweezing systems, well known in the art.

Gravity-Based System

In one embodiment the particles are large enough and of sufficient density to settle quickly on the substrate in response to gravity. For this purpose, the particles 108 may be greater than 500 nm, with particles as large as 1 µm being utilized. In this embodiment, the slide or chamber is inverted, and unbound particles (i.e., cells/colloids) are allowed fall from the surface 109. The particles 108 are allowed to sediment into contact with a patterned substrate 200. The slide or chamber can be monitored in real-time, or the particles can be allowed to fall for a set time, and then the slide or chamber is examined for bound material (i.e., image analysis is performed). Advantages of this system are that there is no need for external reagents, there are few moving parts, and it is cost effective, with no external force mechanism being required.

Centrifugal-Based System

In one embodiment, a centrifugal-based system is used, and is similar to the gravity-based system above, except that a centrifugal force is used to remove the particles from the surface 109. The slide or chamber is rotated and after a set time, the centrifugal system is stopped and binding is examined (i.e., image analysis is performed). This system has the same advantages as the gravity-based system, with the additional advantage that a very large dynamic range can be performed.

Flow-Based System

In one embodiment, a flow-based system is used, where solution is flowed past the particles bound to the surface 109, and the viscous drag force is used to probe binding. Flow is generated with a syringe pump, or an electrophoretic flow (using an individual test, for example). The detection system may include a flow-cytometer setup, or simple CCD/image analysis may be used to monitor particle removal. Calibration may be required with this system. This system has the advantages of being relatively inexpensive, has a very large dynamic range, and is very fast.

Diffusion-Based System

In one embodiment, a diffusion-based system is utilized, where particles 108 are allowed to sediment to the functionalized surface 109 and the amplitude of Brownian motion is measured using imaging analysis. Advantages of this system are that it is cost-effective, with no external force mechanism required, no external reagents needed, and no moving parts.

Magnetic-Based System

In one embodiment, a magnetic-based system is used, where particles (i.e., cells, paramagnetic colloids) are allowed to sediment to a functionalized surface 109. In the case of cells, functionalized magnetic colloids are then dispersed into solution which bind to the cell surface. A magnetic field gradient is then applied (either bulk or with a probe outside of the sample cell). Unbound cells/colloids are removed and binding is monitored using imaging analysis or a feedback loop on the B field microscope. Advantages include the potential for non-imaging based detection, a relatively large dynamic range, the potential for bulk and microscopic applied fields, and that it is fast.

Holographic Optical Tweezing

In one embodiment, holographic optical tweezing, according to known methods, can optically trap and move the particles onto the surface of the chamber 118. Image analysis is performed to detect binding interactions. The advantages include few moving parts, no external reagents, and a continuously adjustable applied force.

Binding Techniques

FIGS. 1A-1C show microscopy apparatuses 10 for performing the present invention. A solution containing particles 108, is placed on a slide, or made to flow through a chamber 118 of a well plate or microfluidics device 116, and over a substrate 200, and the particles settle on the surface 109 according to gravity, centrifugal forces, etc. (as describe above). The particles 108 are investigated to identify whether the particles 108 bind to the capture surface regions 210, 211, 212 etc. on the substrate 200 (or on other particles 108) (see FIG. 3).

In one embodiment, the capture surface regions 210 etc., on the substrate 200 include binding probe(s) which render the substrate 200 capable of specifically interacting with a given analyte or other chemical entity. A "probe" is a molecular entity, particle, or assembly of molecular entities that has a specific binding preference (a "specificity") for a given target particle, molecule, assembly, ligand, or moiety thereof. The analyte can be on the surface of the substrate 200, on a surface of the particle, or in the solution. The capture surface region 210 etc. may include probes that are part of complexes; e.g., immobilized molecules with one or more covalently or non-covalently bound molecules or particles. The substrate 200 may also include an array of probes, or a plurality of elements of a set, disposed at discrete spatial positions on the substrate 200, whether at one or multiple instances of time, and whether regularly spaced, periodically spaced, or otherwise. A substrate or sensing array 200 may include a plurality of capture surface regions 210, 211, 212 etc., which may have varying specificities.

The surface of the particle 108 will include entities such as a "chemical species", which is any molecule, molecular assembly, macromolecule, macromolecular assembly or moiety. The term "chemical species" expressly includes biological and non-biological macromolecules such as peptides, proteins, carbohydrates, glycoproteins, antibodies, nucleic acids, polymers, drug complexes, and the like.

In the present invention, a glass slide 105, coverslip, plastic, or silicon substrate may have multiple capture surface regions 210 etc. with specific probes to form a sensing array 200 such as a DNA array, protein array or microarray. Any scale of capture surface region 210 etc., is within the scope of the present invention. More particularly, the capture surface region 210 may be in the range of micrometers to centimeters, and may be larger than a particle 108, in which case it may interact with multiple particles 108 in the solution. Moreover, the scale need not be uniform throughout a sensing array 200.

Although examples described herein are stated in terms of a planar substrate 200, the capture surface region 210 etc. may also be a surface of a nonplanar substrate or a second particle; for example, smaller particles may be observed to interact with larger particles coated to form a capture surface region 210.

In one embodiment, the solution containing the particles 108 is flowed into a chamber 118 over the substrate 200, and the particles 108 are caused to contact capture surface regions 210, 211, 212 etc. on the substrate 200. As stated above, the contact may occur passively by settling of the particles by gravity, or by active means, such as through centrifugation, electrophoresis, activation methods described above, or by optical forcing, or moving the particles to the substrate using optical trapping techniques, among others. The capture surface region 210 etc. or larger portion of the substrate 200 may be bounded by a water-impermeable barrier to keep the solution over the substrate 200. For example, the substrate 200 may include walls forming wells 418, or the capture surface regions 210 etc. may be bounded by hydrophobic regions, as known in the art of microfluidics devices.

After contact between at least one of the particles 108 and a corresponding capture surface region 210 etc. of the substrate 200, a specific binding interaction may occur between them if a specific chemical entity is present on the surface of the at least one particle 108. In that case, the binding between the particle 108 and the surface 109 creates a "surface-associated" particle. For most analytical purposes, the binding interaction will be noncovalent, but specific covalent binding interactions are also contemplated. Further, where multiple probe molecules are presented by the capture surface region(s) 210 etc., this interaction with the particles 108 may be multivalent.

As described in more detail below, for analysis of molecules in the solution, the specific chemical entity may be provided on the surface on the substrate 200 (so it will typically be present), whereas for the analysis of particle surfaces (e.g., a cell surface), the presence or amount of the specific chemical entity is generally unknown except, of course, in the case of a control or calibration reaction.

Due to settling of the particles 108 in the solution, under gravity or another method, contact or proximity with the capture surface regions 210 etc. may be ensured. In cases where the required binding partner species are found on the capture surface region 210 and the particle surface, the particle's proximity to the surface 109 acts to ensure that the partner chemical species will be in close proximity to encourage rapid binding interaction. This is advantageous in comparison to any conventional assay in which free molecular diffusion is required and may occur, limiting the opportunities for binding to a surface. Thus, this method may be advantageous in both the speed to achieve binding as well as the degree of binding achieved.

In one embodiment, each of the particles 108 bears an ensemble of molecules that are complementary to an ensemble of binding molecules on the capture surface region 210 etc. (e.g., a receptor-ligand or probe-target pair). As a result, a plurality of specific binding reactions will occur between the particle 108 and a capture surface region 210 etc., thereby creating a plurality of "tethers" 400 between the particle 108 and the capture surface region 210 etc. In other words, the specific binding interaction exhibits a characteristic avidity (i.e., cooperative or cumulative affinity due to multiple chemical/biochemical interaction analogous to the avidity of multivalent antibodies). The complementary binding partners of the tethers 400 may be affixed to the particle 108 and surface with a binding strength that exceeds the strength of the specific binding reaction (e.g., covalently linked or linked through a strong non-covalent interaction such as a biotin-avidin interaction). The above may involve an ensemble having multiple particles 108 binding to either one capture surface region 210 etc., or to multiple capture surface regions 210, 211, 212 with corresponding affinities for different chemical entities.

Particle Fluctuation

In one embodiment of the present invention, once bound, the particle 108 does not rupture its bond to the capture surface region 210 etc., but rather, the degree to which the particle 108 exhibits positional freedom may be used to determine the presence, absence or amount of the analyte.

In one embodiment of the present invention, the particle fluctuation includes multiple, successive changes in the particle's motion. For example, the particle 108 movement may change direction due to Brownian motion, or due to cyclical application of forces in accordance with the activation methods described above. Such translational movement, or positional fluctuation, may result from thermodynamic fluctuations or other influences, e.g., Brownian motion, convection, acoustic waves or other forces (i.e., activation methods). In a particular embodiment, the motion of the particles 108 is the result of forces that will approximately cancel out over a long enough time; i.e., the net force exerted on the particle 108 will be approximately zero. Examples of forces that cancel include random and non-random forces, such as periodic forces. For example, the positional fluctuation may arise solely from the fluctuations in pressure or movement from thermal energy.

In one embodiment, the amount of particle motion is increased by the activation methods described above, in order to enhance detection, while the particle 108 still remains bound to the capture surface region 210 etc. In this embodiment, the particle 108 may move, without substantial rolling, on the capture surface region 210 etc. In another embodiment, this bonding/lack of rolling may be maintained even though motion is stimulated through application of forces, as described above with respect to the activation methods, to thereby increase the sensitivity of the measurement. As noted above, the forces from the activation methods are selected to increase motion without rolling/rupturing the specific binding of the particle 108 to the capture surface region 210.

When the binding potential of the capture surface region 210 etc. is properly tuned to a particular affinity with the particle 108 for a specified temperature range, measurements of the positional freedom of the particle 108 reveals that the presence of specific binding interactions between the capture surface region 210 etc. and the particle 108 is correlated with a reduced amount of positional freedom. The specified temperature range may be, for example, 0° to 40° C., or more particularly, 20° to 40° C., to most accurately perform the measurements. The temperature of the substrate 200 and adhered particles 108 may be held in this specified range using a thermal control mechanism (e.g., a commercially available temperature-controlled microscope stage), a water bath, an incubator, an air-jet of controlled temperature, or other methods.

In the present invention, measurements of the presence, absence, or amount of an analyte in the chamber 118 may be made under such conditions of binding potential. After settling on the substrate 200 due to gravity or other means (i.e., centrifugal, optical trapping, etc.), the particles 108 may exhibit apparently random translational movement due to the influence of local pressure fluctuations in the solution. Such translational movement refers to a positional fluctuation of the center of mass of the particle 108, which is distinct from rotation in that rotation refers to motion about the center of mass of the particle 108 concerned.

Image Acquisition & Processing

The particles are illuminated using the above microscopy apparatus 10 (FIGS. 1A-1C), and bright-field, dark-field, phase contrast, differential interference contrast (DIC), holographic imaging, and other optical microscopy methods may be used. One advantage of laser illumination (see FIG. 1C) is its higher contrast, but bright-field has the advantage of its robustness and lack of noise from the scattering of artifacts. DIC and phase contrast microscopy have the advantage of not exhibiting the normal speckle and artifacts associated with monochromatic interference.

Images of the particles 108 are collected by the camera 112 and analyzed by the computer 113. Forces may be applied to the particles 108, including random thermal forces and other applied forces, including the activated methods described above. A time-series of images of the particles in the field of view are acquired by the camera 112 (at least N=2 images, but a higher number of images may provide greater precision). Important parameters which may be chosen include the time interval between images and the total time over which a particle is observed, in accordance with the type of particle and the imaging method.

The particles 108 to be analyzed in the images may be chosen based upon their size, shape, orientation, appearance, proximity to other particles, where they are located in the image, etc., and can be based upon one image or several images. The significance of the statistical sampling of particle binding interactions depends on the number of particles measured, with increased statistical significance achieved with the larger the numbers of particles analyzed. While some systems may yield high confidence levels with N less than 100, other systems may require N of 1,000 to 10,000 or even greater.

Measures of Positional Fluctuation

A measure of positional fluctuation is a quantitative measure of the response of a surface-associated particle 108 to a stimulus, from which the positional freedom of the given surface-associated particle 108 is inferred. How the particles move in response to small forces, such as random thermal forces (i.e., Brownian motion), bulk motion of suspending fluid caused by an applied pressure (i.e., valves) induced by motion of the substrate/sample container, by acoustic vibration, and other forces from the activated methods described above, are observed and quantified.

The measure of positional fluctuation may be a categorical or qualitative measurement (e.g., a binary value). Alternately, the measure of positional fluctuation may be a quantitative value. For example, the measure of positional fluctuation may be obtained by measuring variations in light scattered from one or more particles 108 in a specified "neighborhood" (described below) of the capture surface region 210 etc. for a specified time. The measure of positional fluctuation may be a statistical measure that describes the time dependent positional evolution of a particle 108 in a specified neighborhood and may be expressed as the variance, standard deviation, root mean square (RMS) travel, or autocorrelation function of the particle position associated with a time-series of observations.

The "neighborhood" of the capture surface region 210 etc., may be predetermined and programmed into the computer 113 as a region within a boundary (e.g., a circular or square region) around the position of a known particle 108 in a capture surface region 210 etc., in which the motion is observed. Choosing the size of the neighborhood of the capture surface region 210 etc. may require a statistical analysis (i.e., from calibration data), and may be specified to contain all the likely positions of a particle 108 for a given experimental time, and may be specified to be small enough to maximize sensitivity of the positional freedom measurement, depending on the measuring technique used.

The positional fluctuation is observed within a specified area (neighborhood) of the capture surface region 210 etc., which encompasses an expected range of positions of a particle 108 over a period of observation time. Thus, a particle 108 that is adhered to a capture surface region 210 etc. is determined to have the specific binding target of the capture surface region 210 present on its surface if it fails to move greater than a certain distance after a certain amount of time or number of observations.

The measure of positional fluctuation may be derived from a recorded time-series of measurements of the position of the particle 108 in the plane of the surface of the substrate 200, which may be expressed in terms of x, y if a Cartesian coordinate system is used. Some or all of the recorded observations may be stored in a tangible computer memory or database for later processing of positional freedom and determination of related values such as binding affinities. Alternately, the observations may be processed continuously by the computer program.

Changes in positional freedom in the z-axis (i.e., the direction orthogonal to a plane defined by the surface of the substrate 200) may also, through coupled motion, influence the positional fluctuation measured from the x, y positional data. Alternately, the motion in the z-axis may be measured directly by the computer program and used in the determination of positional fluctuation. Polar coordinates may also be used. The positional data of the time-series may be measured in relation to a fiduciary marking (e.g., of the first surface or microscope optics), of the first surface region, of a sample holder or microscope stage, or of other particles or microscopic objects. Optionally, the path of particles may be tracked and data about the path stored to the tangible computer medium according to particle tracking methods described below.

The measure of positional fluctuation of the particles 108 may be determined for each particle individually (including through parallel processing of an image of multiple particles), or images of multiple particles 108 may be manipulated mathematically or computationally in ways that do not require identification of individual particles 108. For example, successive images of multiple particles may be acquired at two or more times and a digital comparison (e.g., image differencing) of the images used to parameterize a time-dependent autocorrelation function or time-dependent probability function.

Measures of positional fluctuation are carried out with the naked eye, or by using a microscopy apparatus 10 described above. In another embodiment, the positional fluctuation is measured using a microscopy technique involving coherent illumination (holographic fluctuation microscopy, using the apparatus of FIG. 1C). For example, holographic microscopy enables acquisition of high-resolution three-dimensional position data. Accordingly, confident determination of the presence or amount of analyte may be made more quickly, or a higher confidence or sensitivity may be achieved for a given data acquisition time.

Thus, in one embodiment, after loading a sample 107 onto a sensing array 200, mounting the array 200 into the apparatus 10, and after allowing the particles to settle and contact the capture surface regions, analysis may be initiated manually, or by pressing a button (physical or via a GUI), to initiate a computer program.

In any of the apparatuses utilized, images are taken by the camera 112 and viewed on a monitor or screen which form part of the computer system 113. Any computational analyses described herein, may be conducted as part of a computer program(s) which forms part of the microscopy apparatus 10 described herein. The computer program is run by the computer 113, and all data obtained by the microscopy apparatus 10 can be processed and saved in the computer's memory or an external database.

In an automated measurement apparatus, once analysis is begun, the computer program of the microscopy apparatus 10 will automatically focus on a capture surface region 210, etc. The computer program will then automatically find one or more particles 108 and then select them for immediate analysis. Optionally, the computer program will utilize the apparatus 10 to image the particle 108 to determine if it meets a specified set of criteria.

The apparatus 10 may use pattern recognition routines, size and shape data (e.g., detection of objects within a specified appearance range for a red blood cell or other particle) absorbance data (e.g., detection of red color in a red blood cell), fluorescence microscopy data (e.g., presence of a dye or labeled antibody), and other spectral data or other non-spectral measurements to make this determination.

A time-series of images is acquired (at least N=2, with more images being preferred) by the camera 112, and the time elapsed between images and the length of time series is determined by the computer 113 by particle type, imaging method, and the particles being measured. The field of view should contain many particles for observation and measurement. Additionally, multiple fields of view may be sampled, either within a single capture surface region 210 etc., or in multiple capture surface regions 210, 211, 212. For some analysis techniques, only 1 or 2 frames need by stored in memory at a given time.

Detection modes that may be employed include digital video microscopy (included automated microscopy), use of a quadrant photodiode, microscopy with coherent illumination, measurements of scattered light, holographic microscopy and evanescent wave techniques.

For subsequent analysis, the computer program will record, in computer memory, database, or other computer readable medium, the capture surface region 210, etc., with which it was associated. The identity of the capture surface region may be determined from machine-readable markers, from knowledge of the cartridge orientation with respect to reference markings or other method. The selection and analysis of particles 108 is repeated with the above-described optional autofocus step, until a termination threshold is met. The threshold may be, for example, a given number of particles 108 analyzed in total, a given number of particles 108 analyzed in each capture surface region 210, 211, 212, elapsing of a maximum time, or surpassing of a statistical measure of error.

Binding Detection Algorithms

The method of analysis includes finding a value of the positional freedom of the particles to determine the degree of binding. This degree of positional freedom can be inferred by measuring the degree of fluctuation movement of the particle from the sequence of acquired images. This may be done through a variety of methods including particle recognition and tracking, computing the average of multiple images, computing the average difference between successive image frames, and computing the pixel-wise variation in intensity throughout the time sequence of image. Typically, the computation is done in such a way as to characterize each particle with a measure of movement.

In one embodiment, an analysis of the statistical distribution of the pixel intensity values is calculated for each particle, from which one obtains the distribution of positional freedoms and thus the distribution of binding degrees of the particles. Statistics on the shape of the probability distribution of particle fluctuation measures are processed to indicate the nature of the binding interaction. In processing this distribution, one may use the integrated probability distribution, the fraction of particles with a measured positional freedom above/below a threshold value, how or whether the distribution changes between subsequent measurements, moments of the probability distribution (mean, variance, etc.), comparison of distribution to reference/calibration distributions, or other analysis to characterize the degree of binding. The measure of interest (such as the temperature, viscosity, pH, concentration of an analyte, character of a particle, etc.) may be inferred from the degree of binding or from direct analysis of the movement distributions.

The methods for determining positional fluctuation include, without limitation, 1) the displacement of particles 108 which can be measured using particle tracking methods, etc., 2) statistical measures of the time evolution of the particle position such as the variance (standard deviation) calculated for a set of particle positions observed at a plurality of times within the specified period of time, and 3) measures of physical phenomena resulting from variations in positional fluctuation, such as fluctuations in light intensity in a neighborhood of a particles 108 or ensemble of particles 108 due to light scatter by the particle 108 or particles 108 under suitable illumination.

In one embodiment, the positional fluctuation is measured from a sequence of N images of size W×H, taken by camera 112, by computing the pixel-wise standard deviation of the N images using computer 113. Thus the first pixel in the output image is the standard deviation of the first pixel in the N input images, and so on, for each pixel in the W×H output image. Alternately, the first pixel in the output image may be given a normalized value by the computer program, such as by assigning it the standard deviation of the first pixels in the N input images divided by the mean of the first pixels in the N input images. For each particle observed in the input image sequence, this output image is summed or averaged in a defined neighborhood (area of the capture surface region) of the particle. Thus, a measure of positional fluctuation is assigned to each particle.

In another embodiment, the sequence of N input images is used to generate a sequence of N−1 intermediate images which are computed by the computer program, as the absolute value of the pixel-wise difference in successive input images. A final output image is determined by averaging these N−1 intermediate images. Individual particle fluctuation values are assigned by averaging or summing the values of the output image in the defined neighborhood of each particle.

In another embodiment, an object recognition computer program is employed to recognize the precise locations of the particles of interest in each of the N frames. Tracking algorithms are employed by the computer program, to yield the tracked positions of the M particles found through the N frames. Individual particle fluctuation values are assigned by calculating the root-mean-squared value of the inter-frame movement, dx(t) and dy(t).

In another embodiment, the tracked positions of the M particles over N frames are used by the computer program, to compute the exact real-space interframe displacements of the M particles over the N−1 frame intervals. These M particle displacements are averaged at each of the N−1 frame intervals to yield the average particle movement at each of the N−1 frame intervals, dx_av(t) and dy_av(t). For a system which experiences random forcing, thermal activation, or through a random activation method, the average particle movement should approximate to zero in the absence of vibrations or impulses to the system. In real systems, vibrations, impulses, or other unintended situations can give rise to significant correlated movement observable through dx_av(t) and dy_av(t). The inter-frame movement, dx(t) and dy(t) of a given particle is calculated by the computer program, and a corrected inter-frame movement dx'(t) and dy'(t) is computed by subtracting off the correlated movement: dx'(t)=dx(t)−dx_av(t), dy'(t)=dy(t)−dy_av( )t. Thus, unintended correlated movement which is not associated with the random nature of the actuation is subtracted.

In another embodiment, tracked positions are employed and the average interframe displacements dx_av(t) and dy_av(t) are computed by the computer program and used to indicate an error condition in cases where the average (i.e., correlated) interframe displacements achieve an unacceptably high level, which may indicate a degree of unintended vibration or impact to the system that could give rise to a false reading, instrument damage, or other adverse result.

In other embodiments, the tracked positions are used in conjunction with an activation method (described above) to yield a more precise set of particle fluctuation values under well-controlled activation, which may access higher degrees of forcing or more periodic or controlled forcing than may be available through random thermal activation.

In one such embodiment, activation is achieved through one of the methods described above to achieve multiple forcing intervals, where the forcing is uniform within a given interval. Particle tracking methods are employed by the computer program to identify the response to a given prescribed force by identifying a particle's position during a given forcing interval. Doing this in multiple intervals can yield measurements of the particle's position response to multiple forcing levels or directions, giving more complete information about the nature and degree of binding and giving rise to a more precise measure of its particle fluctuation measurement.

Outcome Determination

In one embodiment, calibration data is first obtained for one, two, or multiple samples 107. For a simple test with two possible outcomes, two control samples can be measured to obtain calibration data. For tests with more than two possible outcomes, such as a measurement where a continuously varying measure may be desired (e.g., measuring temperature, pH, concentration of an analyte, etc.), multiple calibration samples may be used.

In one embodiment, two calibration samples are measured and a single (calibration) threshold value of positional freedom measurement is obtained. Measurements of the positional freedom of the particles 108 in the test sample 107 are compared to the threshold, and if they fall below the threshold, then binding interactions are inferred. If the particles 108 have measurements above the threshold, then no binding interactions are inferred. Thus, a measurement of a number of particles 108 in the test sample 107 yields a count of the number of particles 108 inferred to be more strongly bound and a count of those which are less strongly bound, which alternately can be expressed as a percentage which are strongly bound. By comparing these counts or this percentage to one or multiple reference values, a final measurement outcome can be called, such as "positive", "negative", or "inconclusive" for the given test.

In another embodiment, the set of positional freedom measurements of the particles 108 include a positional freedom distribution. The positional freedom distribution may be obtained for reference samples (e.g., determined from many calibration runs on control samples) as well as for the test sample in question. The test distribution may be compared to the set of reference distributions to determine which control sample the test sample most closely resembles. This may be done numerically through a number of methods including projection, correlation, dot product, minimizing differences, integrating regions of the curves, or other methods. This method may yield a binary result (such as "positive" or "negative") or a non-binary result (such as 0 (negative), 1 (extremely weak), 1+, 2, 2+, 3, 3+, 4, 4+, 5 (very strong)). Thus, the collection of fluctuation measurements can be compared to the collection of fluctuation measurements from reference samples of known character.

Further, the curve obtained could be processed before the comparison is performed. For example, since the low end of the curve is of the most interest, all the distributions (i.e., the test distribution and the reference distributions) could be multiplied by a function which is highest at positional freedom of 0 and decreases towards 0 for higher measures of positional freedom. Such scaled distributions thus place higher weight at the low end of the curves. This may be advantageous for situations in which one wants to emphasize the importance of a small number of strongly bound particles in the presence of a large number of weakly bound particles.

Alternately, if one has a large number of more strongly bound particles 108 and a small number of more weakly bound particles 108, the distributions may be scaled by a function which is low for smaller positional freedom measurements and increases for higher positional freedom measurements. A similar weighting effect may be achieved by incorporating this weighting into the calculation of the distribution properties and their resemblance to each other. Thus, the measured distributions may be processed in a variety of ways to yield the reported outcome of the test, and the details of the processing and judgment should be adjusted to emphasize the most important and differentiating features of the distributions.

Methods such as those described above may be useful for a range of systems, however, for a particular system one should look at the set of control distributions (as well as the characteristics of measurement error) to further optimize the judgment criteria and to gauge confidence intervals or possible reporting of "inconclusive" results. Further, note that the above measurement and comparison steps may be computerized and automated by computer 113.

Applications—Immunodiagnostics

Blood Typing

The present invention has applicability to at least the field of immunodiagnostics (which includes blood typing), and beyond that field, to other diagnostics including live cell assays for pharmaceuticals (i.e., for research past screening and diagnostic testing). In particular, one exemplary embodiment of the present invention includes determining blood typing.

BACKGROUND

There are 30 human blood groups recognized by the International Society of Blood Transfusion (ISBT), with the most important being the ABO blood-group system in human-blood transfusion. The blood groups include A, B, AB, and O. The second most significant blood-group system is the Rh system. Across the 30 blood groups, there are over 600 blood-group antigens, with the Rh system having currently 50 antigens, the most significant being the D antigen.

Thus, red blood cells (RBCs) have many antigens on their surfaces, some of which may be associated with blood "type" (Groups A, B, AB, and O), and the most common antigens, known as the A, B, and D antigens, give rise to one's ABO Rh blood type commonly discussed on the donor cards for people who donate blood (e.g., A−, A+, B−, B+, O−, O+, Rh+, Rh−).

Testing for those surface antigens is commonly called either "forward typing" (FT) or "ABO/Rh antigen typing". This is performed on every blood donor and potential donor recipient, typically at least twice for redundancy. If and only if, a person does not have the A antigen on their RBCs, they will have the Anti-A antibody in their plasma. Similarly, if and only if a person does not have the B antigen on their RBCs, they will have the Anti-B antibody in their blood plasma. In other words, if the person has the A antigen alone on their RBCs (and thus, Anti-B antibodies are present), their blood type is Group A, and if they have the B antigen alone on their RBCs (and only Anti-A antibodies present), they have Group B blood. Group AB will have both A and B antigens on the RBCs, but no antibodies present, and Group O will have no antigens on the RBCs and both Anti-A and Anti-B antibodies present.

"Reverse grouping" (RG) or reverse typing, refers to determining whether a person's plasma has the Anti-A and/or Anti-B antibodies in it. Effectively, this is redundant information to the forward type, and is thus, another check on the result of the forward type. There are many details, but for the most part, this is a simple correspondence. Thus, to do a full "ABO/Rh blood type", forward typing is performed to look for the A, B, and D antigens on RBCs, and the Anti-A and Anti-B antibodies in the plasma by reverse grouping.

As stated above, there are many other antigens on RBCs, but the focus is most strongly on A, B, and D antigens because they are clinically most important—i.e., if there is no match, the transfused patient will likely experience a transfusion reaction, which may be fatal. However, there is a list of 18 other antigens, out of over 600 antigens, which fall into a second tier of importance after A, B, and D, based upon their clinical significance (people will likely experience transfusion reactions if antibodies/antigens are not matched). If tests are performed for these antigens, it is called "extended phenotyping" or "antigen characterization", depending on whether one looks indiscriminately for all 18 (extended phenotyping), or targets specific ones of interest (antigen characterization).

When one is born, one does not normally have antibodies to these 18 antigens independent of whether one expresses the antigens on their RBCs or not. However, if one is exposed to any of these 18 RBC surface antigens, they can develop antibodies to these antigens—i.e., "immunization". This can happen through pregnancy (one may be exposed to one's child's blood and thus antigens on the child's RBCs) or through a blood transfusion. If a person in transfused, they will likely be given blood that has some of these 18 antigens which they do not have, and their body may have an immune response to those antigens (i.e., start producing antibodies). This is not consequential unless the person is exposed to more blood (i.e., a separate transfusion) having an antigen to which they have an immunity. The second time, the immune response can be strong and/or the antibodies can attack the transfused blood, destroying the donor RBCs and giving rise to various clinical problems. For these reasons, anyone who receives a blood transfusion is screened to determine whether they have antibodies to these 18 antigens. This is called "antibody screening" (AbS).

A person is screened as positive or negative for one or more "unexpected antibodies" from these 18 antibodies. If they screen positive, it is then necessary to determine the specificity(ies) of the(se) antibody(ies). This process is called "antibody identification" (AbID). Thus, a patient sample that presents positive AbS, will undergo an AbID to identify the specificity of the antibodies that are present. Then the hospital or lab must find blood which does not have the corresponding antigens using extended phenotyping or antigen characterization measurements on a number of ABO/Rh compatible blood units. Finally, before transfusion, the hospital does a "crossmatch" which in the U.S., typically requires that the patient and donor blood are mixed together to look for a reaction (agglutination of the RBCs). If the crossmatch passes, the blood is released for transfusion.

In the broadest sense, therefore, blood typing is searching for some number of RBC surface antigens along with some number of antibodies to RBC surface antigens. Technology which can identify the presence/absence of antigens (or receptors/binding sites) on cells and the presence/absence/concentration of antibodies (or possibly other molecules) in solution, is valuable in medical diagnostic screening and testing, pharmaceuticals, etc.

As stated above, in the prior art, the most common historical method for such testing is to mix RBCs with plasma or serum solution with antibodies and look for cell aggregation (hemaglutination or clotting). For example, to perform the FT test of RBCs for the A or B antigen, the RBCs are mixed with a solution of Anti-A or Anti-B antibodies, respectively, to determine if there is hemaglutination. If there is hemaglutination, the person has Group A or Group B blood, respectively. If the RBCs agglutinate when mixed with both Anti-A and Anti-B antibodies (or anti-AB), then the person has Group AB blood. However, if the RBCs do not stick together when mixed with either Anti-A or Anti-B antibodies, then the person has Group O blood.

If there is no hemaglutination after the first test (i.e., for A antigen), then a second test is required to determine if there is B antigen, and a third test for D antigen (Rh), to determine blood type—to complete a full forward type test. For example, with Rh typing, if the RBCs agglutinate when mixed with an Anti-Rh serum, then the person has Rh-positive blood. If the blood does not clot when mixed with an anti-Rh serum, the person has Rh-negative blood.

Reverse grouping tests are similar. Hemaglutination is looked for when RBCs with known antigen profiles are added to a sample of plasma or serum. For example, if the blood sample agglutinates only when RBCs with the A or B antigen are added to the sample, the person has Anti-A or Anti-B antibodies, respectively, and thus, has Group A or B blood, respectively. If the blood sample agglutinates when RBCs having either A or B antigen are added to the sample, the person has Group O blood. If the blood cells agglutinate when the sample is mixed with both types of blood (containing A and B antigens), then the person has Group AB blood.

To perform the AbS test, typically a panel of RBCs from 2 or 3 people is used (i.e., 3 persons). There are several variants in how it is performed, but essentially, the test plasma is mixed with one of the cell types to look for agglutination, and then repeated for the other cell types.

Exemplary Embodiment—Forward Typing

Figure 4:
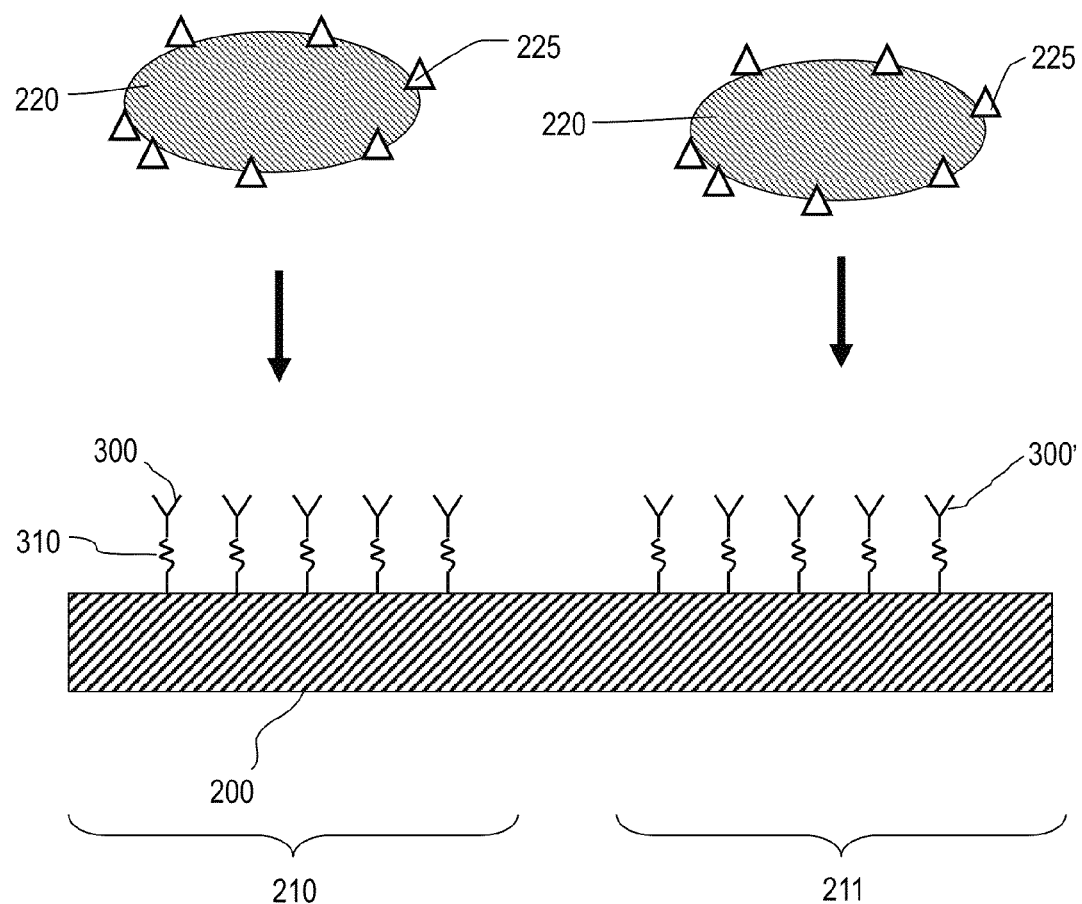
FIG. 4 is a schematic diagram in cross-section, showing red blood cells having surface antigens, which will be detected by the sensing array, to determine the patient's blood type (forward typing), according to one embodiment consistent with the present invention.
Figure 5:
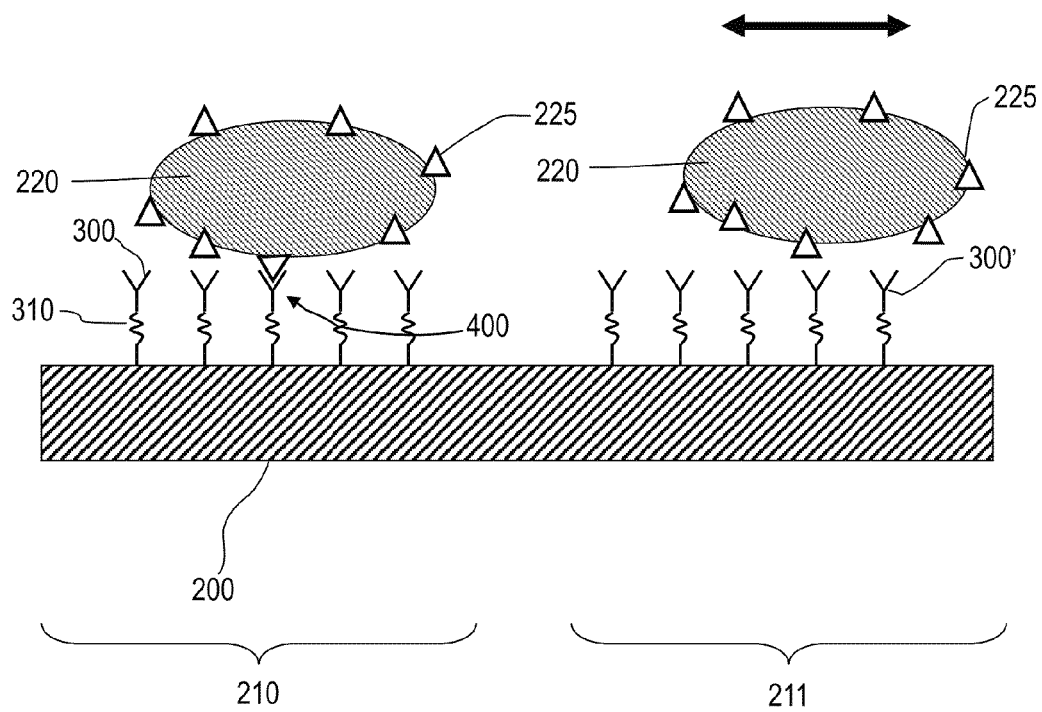
FIG. 5 is a schematic diagram in cross-section, showing the red blood cells of FIG. 4 after settling and association with the probes, and showing specific binding reactions, according to one embodiment consistent with the present invention.

FIGS. 3-5 schematically illustrate an exemplary embodiment of the present invention, to identify blood type by determining the positional freedom of blood cells disposed on a sensing array 200, using the microscopy apparatus of FIGS. 1A-1C, for example. In particular, the sensing array 200 is a glass microscope slide, prepared by techniques well known in the art, including cleaning and silanizing the slide 200 with a functional linker 310 capable of binding probes or probe complexes on capture surface regions 210, 211, 212 (i.e., patches) containing antibodies. As described above, probes are a particle, molecular entity, or assembly of molecular entities, that have a specific binding preference for a given target particle, molecule, assembly, ligand or moiety thereof. In this case, the probes 300, 300' have a specificity for blood antigens. The probes 300, 300' are immobilized using a robust (e.g., covalent) attachment to the glass slide or substrate 200 via the linker 310 (see FIG. 4).

Although this example is directed to blood typing, the method described is applicable to other cell types or to non-cell particles and to other types of surface molecules or moieties.

In this example, the sensing array 200 includes three capture surface regions 210, 211, 212, each having an affinity for a different red blood cell (RBC) surface antigen (i.e., A, B, or Rh), in order to determine blood type (i.e., forward typing). The sensing array is disposed in a chamber 118 and blood (optionally diluted with a suitable buffer), enters the chamber 118 through an inlet 401 (see FIG. 2A), and is disposed over the sensing array 200. The blood is allowed to settle by means of gravity, or any other suitable means (i.e., centrifugation, etc.), as described earlier herein.

FIG. 3 shows the sensing array 200 with a plurality of red blood cells 220 and white blood cells 230 settled on the surface of the capture surface regions 210-212. Optionally, excess cells and debris from the blood are removed by washing with a rinse buffer, and exit through outlet 402 (see FIG. 2A).

As shown in FIG. 4, and as described above, the red blood cells 220 have surface antigens 225, which will be detected by the sensing array 200 to determine the patient's blood type (forward typing). Since the red blood cells in this example, are from a single patient, the set of surface antigens 225 are generally identical for all red blood cells in the sample 107. The sensing array 200, shown in cross section in FIG. 4 and not to scale, has, for example, a first capture surface region 210 and a second capture surface region 211, bearing probes 300 and 300', respectively (capture surface region 212 is not shown for simplicity). Thus, in this example, the probes 300, 300' are monoclonal antibodies against red blood cell antigens, but could be any suitable bio specific or chemispecific probe molecules known in the art (e.g., polyclonal antibodies, nucleic acid probes, aptamers, fully synthetic probes, etc).

FIG. 5 shows the red blood cells 220 of FIG. 4 after settling and association with the probes 300, 300'. After settling, the antigens 225 and probes 300, 300' will be spatially proximate to one another, thereby allowing specific binding reactions to occur. The result of the binding interaction is one or more points of attachments, referred to as "tethers" 400. The tethers 400 will form exclusively, or in greater amounts, when the capture surface region 210, 211 has probes 300,300' that are specific for the antigens present on the surface of the red blood cells 220. The binding reactions occur quickly and for efficiency and speed, can be measured by a suitable detection apparatus, such as those described above, including the microscopy apparatus 10 of FIGS. 1A-1C.

In particular, and as stated above, the detection apparatus 10 is used to detect a measure of the positional fluctuation of a plurality of the red blood cells 220 in association with the capture surface regions 210, 211, etc. The positional fluctuation should depend on the number of tethers 400 that are formed, with the greater the number of tethers 400, and less movement of the particle, the more likely the antigen is present on that red blood cell. Thus, the measured positional fluctuation is used to determine the presence or absence of the specified analyte.

Making multiple such measurements of appropriate analytes allows the detection apparatus 10 to determine a blood type. For example, as described above, the standard deviation in particle or red blood cell position may be compared to a threshold value that is predetermined or derived from a control reaction having blood cells or blood-cell mimics (e.g., particles bearing RBC antigens). A measured positional fluctuation that is lower than the threshold value (indicating statistically less movement of the particle) would indicate the presence of the antigen on the cell.

Figure 6:
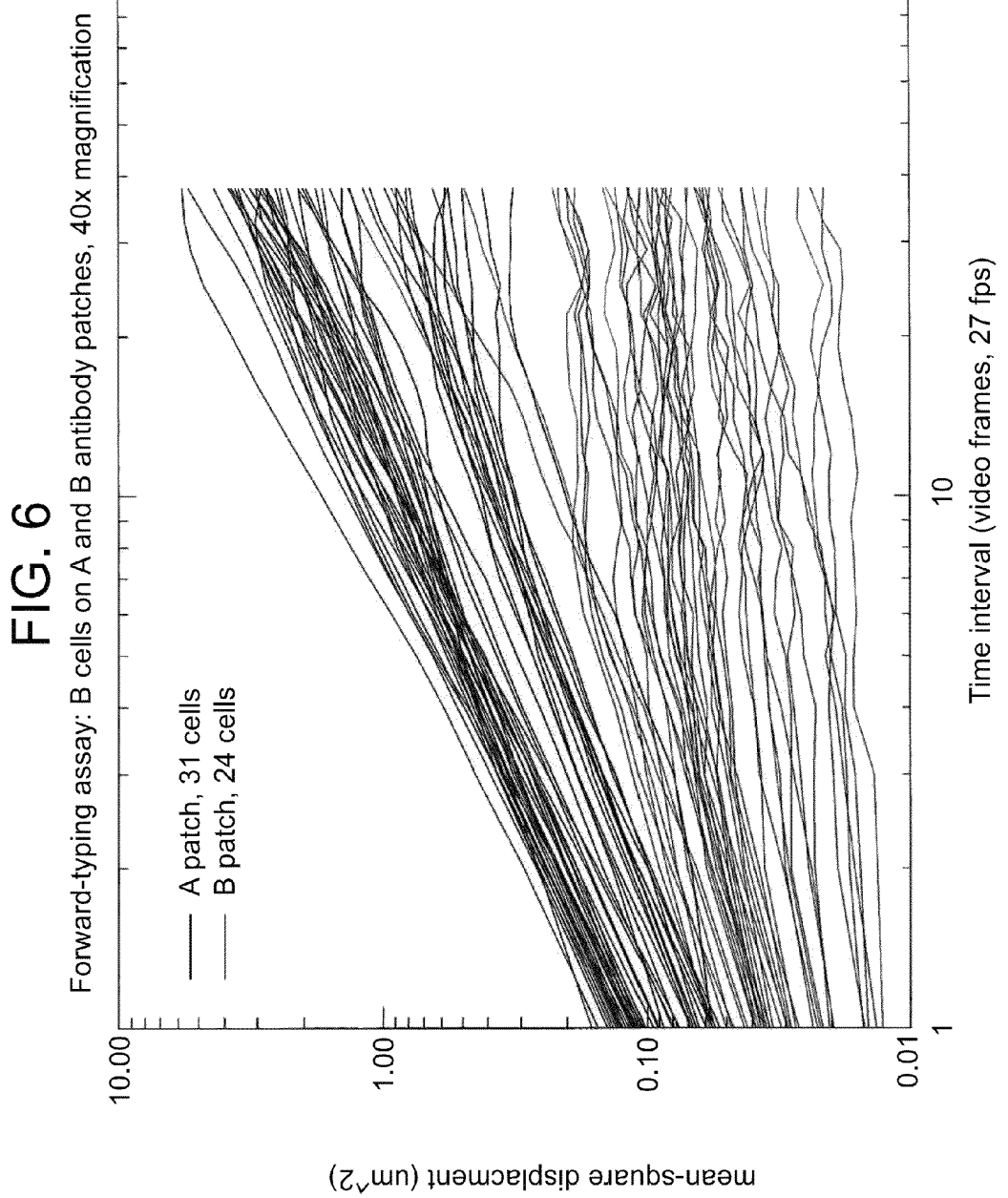
FIG. 6 shows an experiment in forward typing according to one embodiment consistent with the present invention, with the resulting graph showing an observed mean-square displacement of Group B red blood cells as a function of measurement time interval for cells dispersed on two different patches, one with anti-A antibody immobilized on the surface and another patch with anti-B immobilized on the surface. The Group B cells have a lower positional fluctuation on the Anti-B antibody patch than on the anti-A antibody patch, revealing binding of the group B cells to the anti-B patch as well as the timescales required to recognize whether binding occurs without activation.

FIG. 6 shows an experiment in forward typing, where RBCs 220 for Group B blood were tested for positional fluctuation on an Anti-A antibody patch (i.e., disposed on capture surface region 210 in FIG. 4), and an Anti-B antibody patch (i.e., disposed on capture surface region 211 in FIG. 4). The resulting graph shows the time-averaged diffusion rates for Group B (positive for antigen B) red blood cells 220 on substrate 200 with Anti-A and Anti-B antibody coatings (patches 210, 211, respectively). The results show an observed mean-square displacement of the test Group B RBCs 220 as a function of measurement time interval.

Specifically, each line in FIG. 6 represents an RBC 220. The Group B cells 220 bind to the Anti-B antibody patch (i.e., capture surface region 211), but not to the Anti-A antibody patch (i.e., capture surface region 210). Thus, the RBCs 220 on the Anti-A antibody patch 210 display higher displacements overall, and a steadily-increasing displacement for longer measurement intervals, showing free diffusion of the Group B RBCs 220 (the RBCs appear as substantially straight upward lines in the graph), whereas the RBCs 220 on the Anti-B antibody patch display a leveling-off of displacement at longer measurement times, because their distance of travel is limited by binding to the substrate 200. Although the Group B RBCs 220 on the Anti-B antibody patch 211 are tethered to the surface, in short timescales, they appear similar to the RBCs on the Anti-A antibody patch 210, but on longer time scales, they flatten out. Accordingly, there is a characteristic timescale for viewing the positional fluctuation of the particles or RBCs, of about 5-10 seconds in order to see the characteristic features of the graph, and the result that the Group B cells 220 have a lower positional fluctuation on the Anti-B antibody patch 211, which shows binding of the Group B cells.

Figure 7:
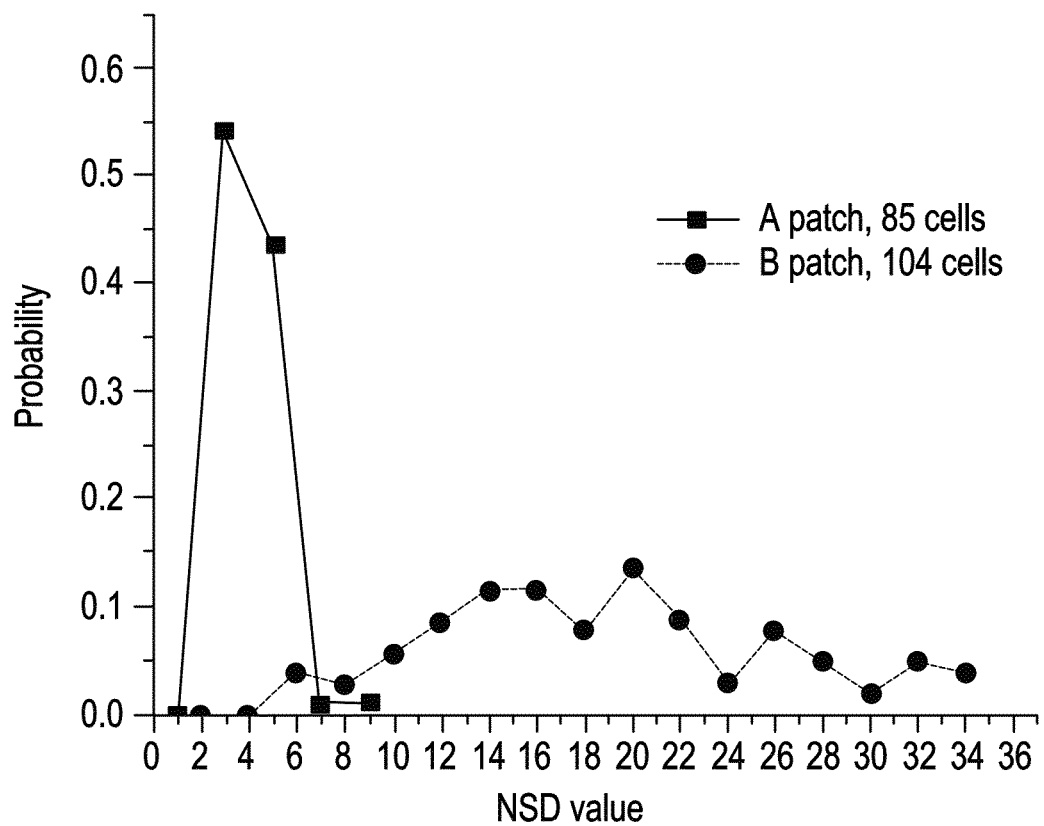
FIG. 7 shows a graph of a forward typing experiment in accordance with one embodiment consistent the present invention, where the probability distributions of the normalized standard deviation (NSD) of the red blood cells are calculated using algorithms.

FIG. 7 shows a graph of a forward typing experiment in accordance with the present invention, where a microscopy apparatus 10, for example, is used, and where the probability distributions of the normalized standard deviation (NSD) of the RBCs are calculated using the algorithms discussed above.

The forward typing experiment included Group A blood cells 220 which were disposed on Anti-A and Anti-B antibody patches 210, 211, similar to the experiment of FIG. 6. The resulting graph shows the probability distributions for the normalized standard deviation (NSD) of the Group A (having A antigen) red blood cells 220 on the capture surface regions 210, 211 of the substrate 200 coated with Anti-A and Anti-B antibodies, respectively. As stated above, the NSD is a measure of positional freedom, and the narrow, low-value distribution for the Anti-A antibody capture surface region 210, etc., indicates particles or RBCs 220 with little mobility. In other words, the vast majority of the Group A red blood cells 220 are bound to the substrate 200. By contrast, the broad distribution for the Anti-B antibody capture surface region 211, etc., indicates that most or all of the particles or RBCs 220 are diffusing freely, and are not bound.

Advantages of the present method and apparatus are not only speed in certain instances, but that the measurements are taken before equilibrium is reached, which normally takes hours to achieve using conventional techniques. In conventional methods, for example, a technician would look for large clumps of cells (hemaglutination) that are visible, often to the naked eye, including uniformly red surfaces, or white surfaces with red clumps etc., which, in certain instances, could take a lengthy amount of time. However, in the present invention, all that is required is to determine a statistically significant level of binding events of a number of individual cells, rather than a macroscopically visible average level of binding over equilibrium, which can be performed efficiently and quickly.

EXAMPLE

Reverse Grouping

Figure 8:
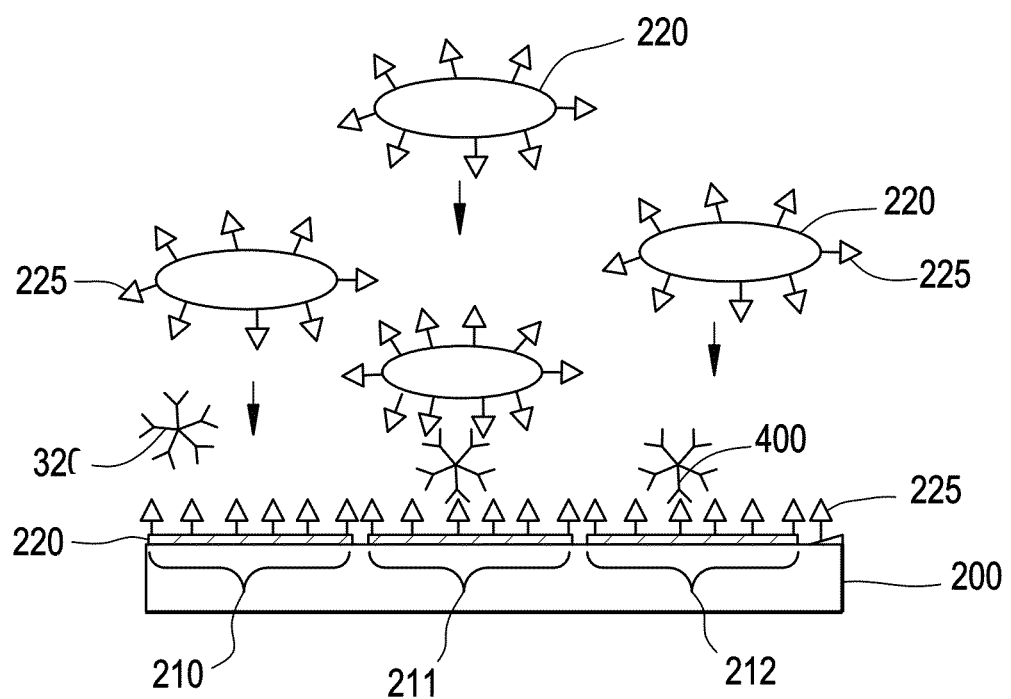
FIG. 8 depicts a sensing array or substrate in cross-section, where the sensing array which is used to identify whether a plasma sample has, for example, Anti-A and/or Anti-B antibodies therein in a reverse grouping test, according to one embodiment consistent with the present invention.

In another embodiment consistent with the present invention, FIG. 8 depicts a sensing array or substrate 200 which is used to identify whether a plasma has, for example, Anti-A and/or Anti-B antibodies therein (i.e., reverse grouping (RG)). The reverse grouping technique is essentially the same as that in forward typing described above, but the antibodies are detected based on a determination of the positional freedom of red blood cells 220 binding to antibodies 320 bound to antigens 225 of red blood cells 220 disposed on capture surface regions 210, 211 of the substrate or sensing array 200. As with the forward typing example, the microscopy apparatus 10 may be used.

More specifically, in this exemplary embodiment as shown in FIG. 8, the sensing array 200 is a glass microscope slide, prepared by techniques well known in the art and as described above, including cleaning and silanizing the slide 200 with a functional linker 310 (not shown in FIG. 8) capable of binding red blood cells 220 on capture surface regions 210, 211, 212 of the substrate or slide 200. Each capture surface region 210, 211, 212 can be made to specifically detect a particular antibody.

An aqueous solution of red blood cells 220 is introduced into a chamber 118 and settled onto the capture surface regions 210, 211, 212 (i.e., patches) of the sensing array 200 by gravity or by centrifugation or other techniques described above, etc., and are bound or stuck to the capture surface regions 210, 211, 212 by the linker 310. The aqueous solution of red blood cells 200 is removed from the chamber 118 and the bound red blood cells 220 are lysed by adding deionized water into the chamber 118 such that the red blood cells 220 lay flat on the sensing array 200, spreading out on the capture surface regions 201, 211, 212 and filling substantially all voids. The deionized water is then removed through the outlet 402 (see FIG. 2A) and a preservative solution (i.e., dextrose dissolved in water) is added and the sensing array 200 is air dried, or dried in a dessicator. The resulting sensing array 200 is covered with flattened red blood cells 220, with a thin, dry layer of preservative thereon which helps preserve the reactivity of the antigens 225 on the red blood cells 220 and increases their shelf life.

To perform the reverse grouping (RG) test, in one exemplary embodiment, plasma is added to the chamber 118 and the array 200 is incubated at approximately 25° C. The antibodies 320 in the plasma fall and coat the surface of the capture surface regions 210, 211, 212 of the sensing array 200. The antibodies 320 are IgM (immunoglobulin M) antibodies with 5 reactors thereon, so one or two of these reactors would bind to the antigens 225 sticking up from the bottom surface of the chamber 118, leaving the remainder of the reactors free. If the antibodies 320 do not bind or stick to the antigens 225 of the flattened red blood cells 220 and coat the bottom surface, indicating antibodies are present to that specific antigen, then the plasma is washed away through outlet 402 using a buffer solution, and it means that the requisite antibodies are not present. (Note that the wash step is optional for this test.)

If antibodies 320 from the plasma bind or stick to the flattened red blood cells 220, then an aqueous solution of probe red blood cells 220, with the desired antigen 225, is then introduced into the chamber 118, and the probe red blood cells 220 will fall and bind to the antibodies 320 that are bound to the antigens 225 of the flattened red blood cells 220 on the bottom surface, forming a sandwich assay.

Accordingly, if the plasma has antibodies for a particular antigen (i.e., anti-A antibodies bound in a sandwich assay to A antigens on the red blood cells 220 on the bottom surface and to A antigens on the probe red blood cells 220 in the chamber 118), then the binding reactions (i.e., number of tethers 400) would be high, and the degree of positional freedom would be low. If there is a high degree of positional freedom of the probe red blood cells 220, then the plasma does not contain the particular antigen (i.e., there are no anti-A antibodies), and the number of binding reactions would be low. In determining the positional freedom of the red blood cells 220, the detection apparatus (i.e., microscopy apparatus 10), calculates the standard deviation of the red blood cell position compared to a threshold value to determine the presence of absence of the desired antibody. The advantages of the present invention are noted above with respect to forward typing.

Example

Flattening of Cells

In one embodiment, a specifically bound particle 108, if compliant under applied forces, may be flattened (inclusive of stretching, flattening, or other changes in morphology) as successive tethers 400 are formed in the tether-forming process. This flattening of the particles 108 (i.e., red blood cells) may be observed microscopically using the microscopy apparatus 10, and may in itself indicate the presence, absence or amount of the analyte (i.e., red blood cell antigens) for which the capture surface region 210, 211, etc. has specificity.

With respect to the application of blood typing, the flattening of the particle 108 has also been observed to be associated with the loss of the central dimple of the red blood cell and this characteristic may be used to indicate the presence, absence or amount of the red blood cell antigens for which the capture surface region 210 etc., has specificity. The flattening and dimple loss may be detected automatically (e.g., by using automated microscopy and pattern recognition software of the microscopy apparatus of FIG. 1C). This flattening effect may be used alone or in conjunction with positional fluctuation measurements to automatically call the blood type.

Exemplary Embodiment—Antibody Screening
a. IgM Class Antibodies

In another embodiment consistent with the present invention, antibody screening (IgM class antibodies), is performed in the same way as reverse grouping (RG) above. Further, since people only produce IgM class antibodies right after exposure, this is a less frequent test.

b. IgG Class Antibodies

However, with respect to a more commonly performed (but more difficult) test, IgG immunoglobulin G, class antibody screening (which utilizes anti-human globulin (AHG) as compared to IgM and RG testing), is performed to look for the 18 different human antibodies, for example. In this embodiment, the techniques are similar to that of reverse grouping (RG), and the microscopy apparatus 10 of FIGS. 1A-1C, for example, may be used. However, this test does require a wash step (see below) which is not necessary in the other types of testing (i.e., IgM, RG).

Figure 9:
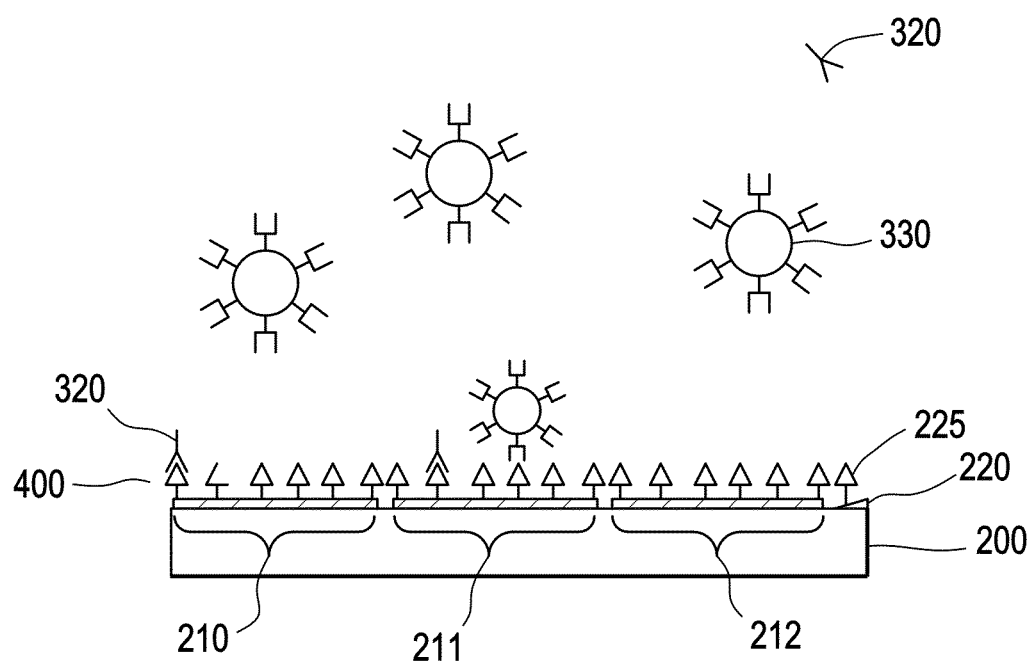
FIG. 9 is a sensing array in cross-section, where an antibody screening test for certain IgG-class blood type antibodies is performed, according to one embodiment consistent with the present invention.

More specifically, in this exemplary embodiment as shown in FIG. 9, the sensing array 200 is a glass microscope slide, prepared by techniques well known in the art and as described above, including cleaning and silanizing the slide 200 with a functional linker 310 (not shown in FIG. 9) capable of binding red blood cells 220 on capture surface regions 210, 211, 212 of the substrate or slide 200. The capture surface regions 210, 211, 212 include a blood panel from several persons, which between them express, all 18 antibodies.

As with reverse grouping (RG), an aqueous solution of red blood cells 220 is introduced into a chamber 118 and settled onto the capture surface regions 210, 211, 212 (i.e., patches) of the sensing array 200 by gravity or by centrifugation or other techniques etc., and are bound or stuck to the capture surface regions 210, 211, 212 by the linker (not shown in FIG. 9). The aqueous solution of red blood cells 200 are removed from the chamber 118 and the bound red blood cells 220 are lysed by adding deionized water into the chamber 118 such that the red blood cells 220 lay flat on the sensing array 200, spreading out on the capture surface regions 201, 211, 212 and filling substantially all voids. The deionized water is then removed through the outlet 402 (see FIG. 2A) and a preservative solution (i.e., dextrose dissolved in water) is added and the sensing array 200 is air dried, or dried in a dessicator. The resulting sensing array 200 is covered with flattened red blood cells 220, with a thin, dry layer of preservative thereon which helps preserve the reactivity of the antigens 225 on the red blood cells 220 and increases their shelf life.

To perform the IgG antibodies test, in one exemplary embodiment, plasma, mixed with a potentiator, is added to the chamber 118. The array 200 is incubated at approximately 37° C. The potentiator speeds the reaction between certain antibody/antigen reactions on the surface of the capture surface regions 210, 211, 212 of the sensing array 200. The potentiator can be chosen to drive the reaction by a number of different means, such as electrostatic means, or by precipitative means, well known in the art.

After incubation, the plasma is washed out very thoroughly through outlet 402 (see FIG. 2A) using a buffer solution, to prevent residual IgG from saturating Anti-IgG antibody particles 320. Thereafter, probe particles 330 are introduced into the chamber 118 by gravity, centrifugal, or other techniques etc., and are settled on the surface of flattened red blood cells 220. The probe particles 330 may be colloid (glass microbeads) 330 or RBCs (not shown in FIG. 9) with the appropriate surface chemistry. The Anti-IgG antibodies 320 may be used to form a bridge between the Anti-IgG antibodies 320 which have stuck to the substrate (flattened) RBCs 220, and the probe particles 330 themselves.

Thus, the Anti-IgG antibody particles 320 will bind to the surface of flattened RBCs 220. The Anti-IgG antibodies 320 can be free or bound to the probe particle 330 initially. In either case, the probe particles 330 end up binding to the antigen 225 on the bottom surface of the chamber 118, via an Anti-IgG antibody 320 of interest from the test plasma, or via an Anti-IgG antibody 320 on the probe particle 330.

Other methods can also be used, and this method can be applied to different types of antigens.

Thus, the entire class of antibodies (i.e., 18 antibodies), can be checked to see which probe red blood cells 330 bind to which capture surface regions 210, 211, 212, and whether any of the 18 antigens present.

As stated above with the other forms of screening, if there is a high degree of positional freedom of the probe particles 330, then the particular 18 antigens are not present, and the number of binding reactions would be low. In determining the positional freedom of probe particles 330, the detection apparatus (i.e., microscopy apparatus 10), calculates the standard deviation of the probe particles 330, using the algorithms described above, as compared to a threshold value to determine the presence or absence of the desired antibodies. The advantages of the present invention are noted above with respect to forward typing.

Infectious Disease Screening

In other embodiments consistent with the present invention, methods and apparatuses disclosed herein are suitable for infectious disease screening (e.g., human immunodeficiency (HIV) virus, hepatitis B virus (HBV), syphilis, human T-lymphotropic virus (HTLV), hepatitis C virus (HCV), syphillis, etc.), by testing for antibodies to these infectious agents. Many of these infectious diseases require multiple screenings to determine if the disease is present, and to prevent the blood supply system from containing the diseases.

In one embodiment, the target antibodies are taken from a blood sample, and testing is done against an array of uniquely treated surfaces to determine an antibody profile. Specifically, the target antibodies are taken from a blood sample for the purposes of detecting viral infection. Proteins that occur on the surface of a given virus may be immobilized on the surface (i.e., solid-phase) thereby being able to capture the specific antibody to that virus. In addition, particles coated with antibodies complementary to another region of the virus antibody are present in the test, such that in the presence of the target virus antibody, immobilization of particles may occur, signaling the presence of the antibody in the blood sample. Such measurements are performed in order to diagnose infection, or quantify target antibody concentration, with suitable controls.

In the present invention, the apparatuses and methods used are similar to those described above with respect to blood typing.

a) HIV

HIV tests are currently antibody, antigen, and nucleic acid tests (NAT), which are used by Western countries. The enzyme-linked immunosorbent assay (ELISA) test is used, then a NAT is used in the U.S. since 1985.

In contrast, in this exemplary embodiment, recombinant HIV antigens are attached by various known methods, such as by using a linker 310, to a substrate or sensing array 200 after the substrate 200 (i.e., glass microscope slide) is prepared by techniques well known in the art and as described above, including cleaning and silanizing the slide 200.

The substrate 200 is exposed to patient serum by introducing the serum of RBCs 220 into a chamber 118. The RBCs 220 are allowed to settle on the surface of the substrate 200 by gravity or centrifugal methods, etc., and if HIV antibodies 335 are present, the HIV antibodies 335 will bind to the HIV antigens 336 on the substrate 200, according to the methods described above, and as shown for example, in FIG. 8.

As above, the patient serum is removed through outlet 402 by washing with buffer solution, leaving specifically bound HIV antibodies 335 substantially undisturbed. A particle-labeled antibody 340 specific towards human antibody (e.g., rabbit anti-human IgG) is introduced into the chamber 118 and tested for specific binding to the HIV antibodies 335 via a measure of positional fluctuation of the particles 340.

This type of assay is particularly advantageous in the context of multiplexing because only one, or only a few types of particle labeled probes 340 may be needed to determine many types of analyte molecules. Thus, after allowing sufficient time for antibody binding, a solution of particle-labeled anti-human antibodies 340 (e.g., anti-IgG, anti-IgM, anti-IgG, and IgA or a combination thereof) may be added and allowed to bind to the capture surface regions. A measurement of positional fluctuation performed by the microscopy apparatus 10 of FIGS. 1A-1C, may then be used to probe the response of the particles 340 to reach conclusions about the patient's past pathogen exposure, immunization state, cancer prognosis or other medical state.

This technique may be applied to several, tens, or even hundreds of antigens in parallel using a few labeled particle types; for example, between one and four labeled particle types. Because so few particle types are needed, it is relatively simple to tag each of the particle types, for example, with fluorophores of differing excitation or emission wavelengths, to deconvolve the results. For example, anti-IgG and anti-IgM antibodies could be tagged with different fluorophores. Note that multiplexing using tags may apply to other assay types described in the various embodiments including those involving solid particles and cells (which may be tagged with fluorescent antibodies, for example). In another example, a patient's antibody profile may be determined with respect to numerous antigens for the purposes of diagnosing an allergy.

b) Pathogens

In another example, an analyte is coupled via a probe to a substrate. Probe antibodies with specificity for antigens commonly present on pathogens (bacteria or viruses) are covalently coupled to the substrate to form capture surface regions. A sample suspected of containing the bacteria or viruses is added to the chamber, and allowed to settle (by gravity, centrifugal or other means), and binding reactions are allowed to proceed. Probe particles with covalently attached antibodies that are specific to the pathogens are added and their degree of binding is determined by microscopic observation and quantification of their positional fluctuation using the microscopy apparatus 10. Alternately, the bound pathogens may be detected using an indirect assay as generally described in connection with FIGS. 19A and 19B.

Detection of Unique Combinations of Complementary Antigens

Depending on the desired analysis, mixtures of probe types and specificities may also be used. For example, a capture surface region 210/211/212 of a sensing array 200, with multiple immobilized monoclonal antibodies, may be used to detect the presence of cells that bear a unique combination of complementary antigens (e.g., certain cancer or stem cells).

Exemplary Embodiments in Chemistry

In other exemplary embodiments, the methods of the present invention may include variants on the chemistry and techniques, and with reference to FIGS. 4-5 and 8-9, as follows.

Bioinert Moieties

Figure 17:
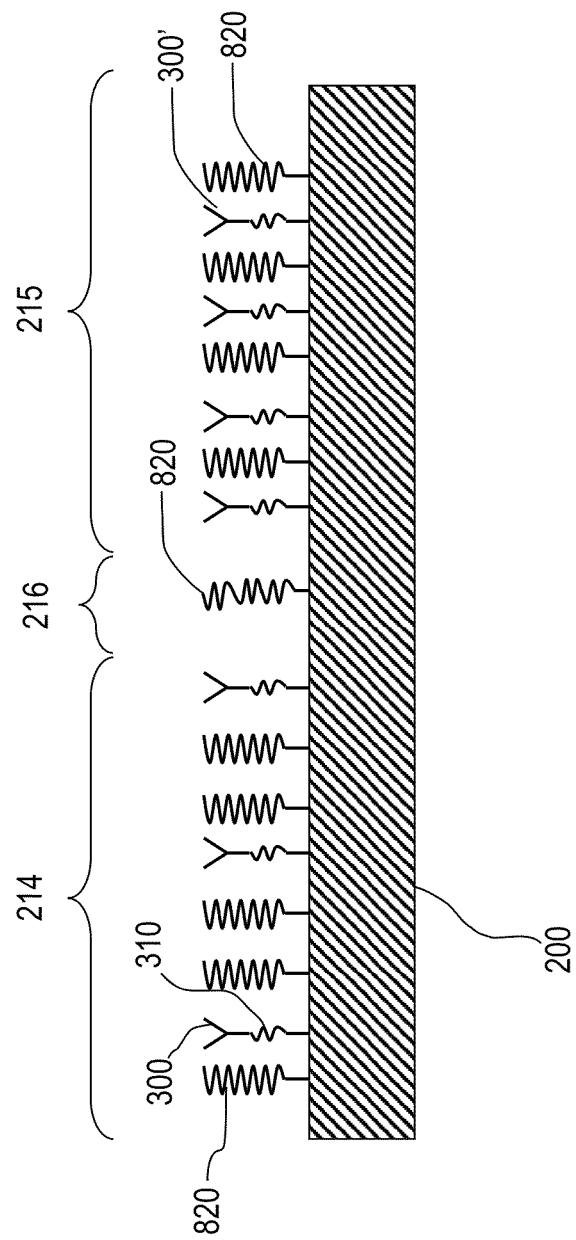
FIG. 17 is a cross-section showing capture surface regions on a substrate that include both probes and bioinert moieties, according to one embodiment consistent with the present invention.

FIG. 17 shows capture surface regions 214 and 215 on a substrate 200, that include both probes 300, 300' and bioinert moieties 820. The bioinert moieties 820 may be, for example, hydrophilic polymers such as polyethylene glycol moieties linked to the substrate 200 via a silane linkage 310. The linker 310 may also be bioinert or have a bioinert component. The bioinert moieties 820 serve to reduce the probe 300, 300' density with a minimal or negative contribution to nonspecific binding interactions between the cells (not shown) and the capture surface regions 214, 215.

Bioinert moieties 820 may also be included on regions 216 between capture surface regions 214, 215. The areal density of probes 300,300' may also be altered by combining the probes 300, 300' with a reactive but bioinert reagent—e.g., glycine when amine-reactive crosslinkers are used, or cysteine when sulfhydryl reactive crosslinkers are used.

Direct Assay—Analyte Coupled to Substrate

In one the embodiment consistent with the present invention, the analyte 226 may be first attached to a substrate 200 and probed with particles 800 or further probes and particles, as described with respect to FIGS. 18A-19B, below.

In the embodiment schematically illustrated in FIGS. 18A-8B, a direct assay involves binding or capturing an analyte 226, 226' on the substrate 200 and measuring the positional fluctuation of a reporting particle 800, having probes 300, 300' affixed to its surface. For example, a 0.01 to 100 micron diameter glass or plastic bead 800 with immobilized antibodies, for example, may be used to probe a target analyte 226' that is specifically or nonspecifically bound to (or captured by) the substrate 200. The analyte 226, 2006' may be covalently or noncovalently attached to the substrate 200. The probe 300, 300' and label 800 may also be combined into a single biological entity; e.g., a natural or genetically engineered cell expressing a surface protein that acts as a probe.

In particular, in FIG. 18A, an analyte antigen 226, for example, is bound to a capture surface region 210 and a particle 800 with immobilized antibody probes 300 is contacted with and bound to the capture surface region 210. The positional fluctuation is then measured by the known methods described above, using a microscopy apparatus 10. If the antibody 300 recognizes the antigen 226 as is shown in FIG. 18A, there will be binding between them, and thus, a lesser positional fluctuation than the situation shown in FIG. 18B, in which the antibody 300 does not recognize a non-binding antigen 226' (i.e., no binding takes place).

Alternately, the target analyte 226 may be an antibody, and the probe 300 on the particle 800 may be an antigen (see FIG. 5, for example). The analyte 226 could also be part of a cell surface where the cell is adhered to the substrate 200.

Indirect Assay—Probe Complex

An indirect assay involves detecting a characteristic of a second probe 300 (see FIG. 19A) that is bound to the first probe 320 to form a complex (e.g., a biomolecular complex) that presents a cognate binding partner to a readout particle 800. The second probe 300 may be specific for a chemical moiety of the first probe 320, or for a label of the first probe 320 (particulate or otherwise). Further (ternary, quaternary, etc) complexes may also be used. Further examples of complexes are also given in connection with the embodiments of FIGS. 20-21. Like the direct assay described above, the observed particle 800 characteristic is the positional fluctuation of the particle 800 which provides a measure of its positional freedom.

Figure 19A:
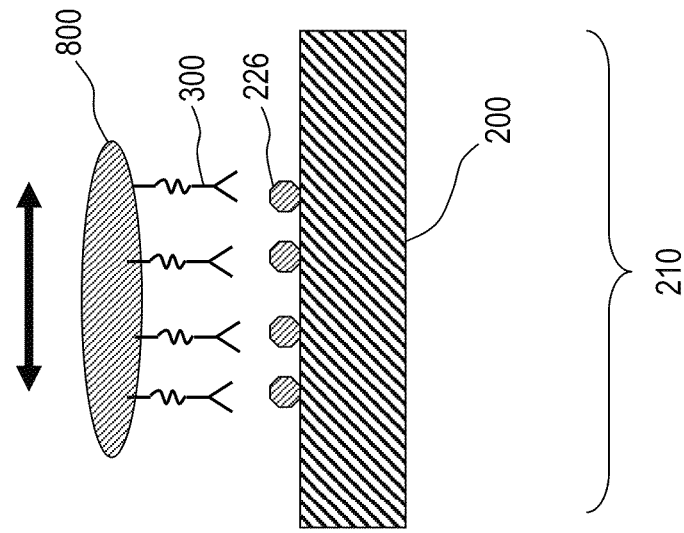
FIG. 19A is a cross-section showing an indirect assay of a second probe bound to a first probe to form a complex (e.g., a biomolecular complex) that presents a cognate binding partner to a readout particle.

In the exemplary embodiment illustrated in FIG. 19A, unlabeled monoclonal mouse antibodies 320 may be used as a first probe 320 and contacted with immobilized target antigen 226 (e.g., directly immobilized on substrate 200 or integral to an immobilized cell). The second probe 300 may be a particle 800 labeled with attached probe moieties 300 that are polyclonal rabbit anti-mouse antibodies. The second probe particles 300 may be contacted with the first probe antibodies 320 according to the methods described above, allowed to bind, and tested for specific binding interactions by observing the fluctuation responses of the particle 800 (i.e., under the influence of Brownian motion) using the appropriate microscopy apparatus 10.

Figure 19B:
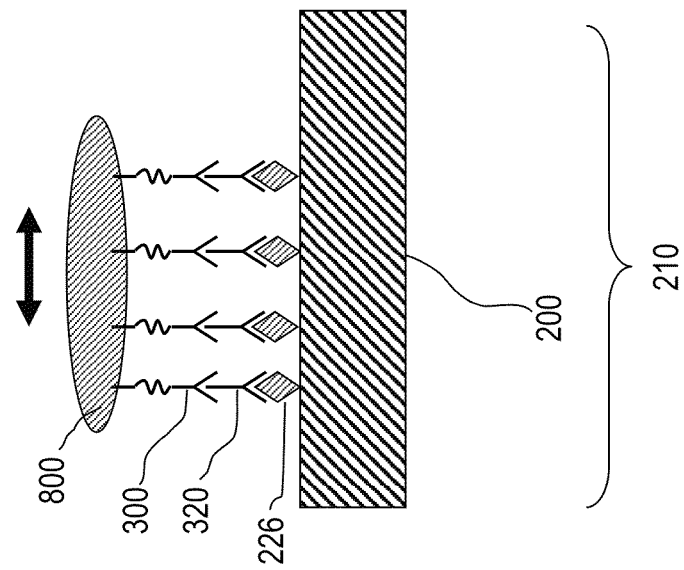
FIG. 19B shows lack of a specific binding reaction, according to one embodiment consistent with the present invention.

As shown in FIG. 19B, lack of a specific binding reaction results in a corresponding difference in the measurement of positional fluctuation and a resulting greater positional freedom of the particle 800.

Competitive Assays

Conventional competitive assays involve detecting an event associated with displacement of a bound analyte or reporter or other molecule. However, the competitive assay is usually performed in a serial manner, yielding few data points.

By contrast, the competitive assay of the present invention, as described herein, may be performed in a parallel manner, i.e., by obtaining a positional fluctuation measurement for multiple particles concurrently or in rapid succession. As a result, more data points may be obtained for higher-confidence results and/or more types of targets may be tested.

Figure 20:
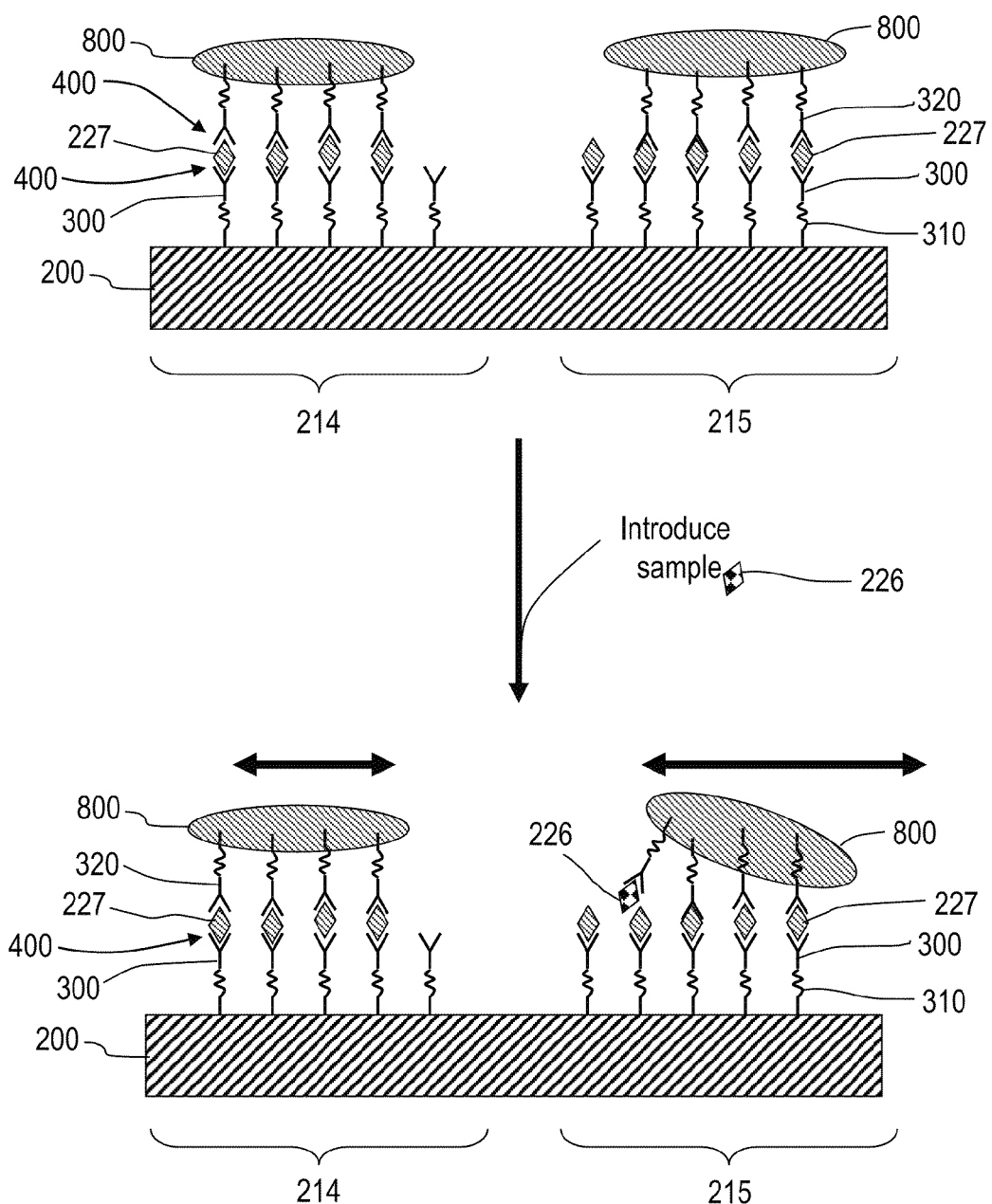
FIG. 20A is a cross-section of a competitive assay, showing a ternary sandwich structure formed at the capture surface regions of a substrate.
FIG. 20B shows where the analyte molecules displace the placeholder molecules given a suitable time to approach equilibrium, or the analyte molecules may block binding if introduced before the placeholder molecules, according to one embodiment consistent with the present invention.
Figure 21:
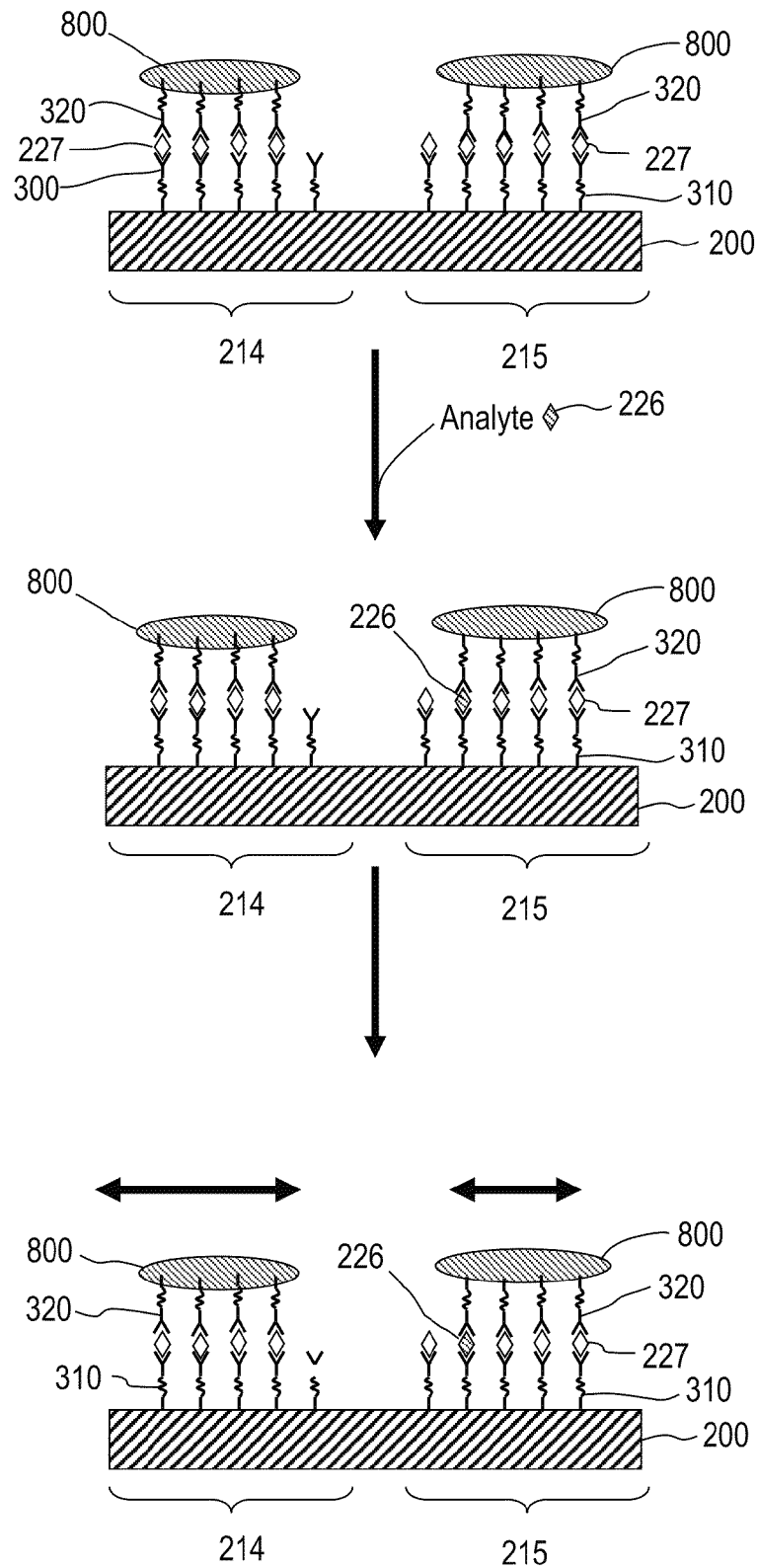
FIG. 21 is a cross-section which shows a reaction scheme for a competitive assay in which the placeholder molecules have a lower affinity for the probes than the analyte molecules, according to one embodiment consistent with the present invention.

FIGS. 20 and 21 illustrate some exemplary embodiments of assay configurations that utilize the determination of the positional freedom of a particle, to determine binding interactions.

As shown in the FIG. 20A, ternary sandwich structures are formed at the capture surface regions 214, 215 of a substrate 200. The sandwich structures are comprised of (i) substrate 200 bound probes 300', (ii) placeholder molecules 227, and (iii) particle-bound probes 320 immobilized on particles 800. The placeholder molecules 227 have a specific affinity for both the substrate-bound and particle bound probes 300, 320, respectively. The placeholder molecules 227 may have a binding potential for the probes 300, 320 that is similar to that of an analyte of interest in the target sample.

For example, the placeholders 227 may be recombinant forms of antigens of interest. Additionally, substrate-bound probes 300 may have differing affinities or specificities to various analytes of interest, and may be pre-assembled as ternary complexes (which are a form of tether 400) with suitable placeholder molecules 227 and particle-bound probes 320.

When a sample is added having analyte molecules 226 with an affinity for the probes 300, 320, as shown in FIG. 20B, the analyte molecules 226 will tend to displace the placeholder molecules 227, given a suitable time to approach equilibrium, to a degree that depends on relative binding constants and mass action. If the particles 800 and the sandwich structures on the capture surface regions 214, 215 interact in a polyvalent manner (i.e., with an avidity), under intermediate concentrations of the added analyte 226, only some of the placeholder molecules 227 will tend to be competitively displaced, and the tethers 400 correspondingly disrupted. This competitive displacement state may be detectable as differences in positional fluctuation measurements by a microscopy apparatus 10, as described above.

In an alternative embodiment, FIG. 21 shows a reaction scheme for a competitive assay in which the placeholder molecules 227 have a lower affinity for the probes 300, 320 than the analyte molecules 226. Capture surface regions 214 and 215 on substrate 200 have probes 300, and particles 800 have probes 320, that are specific for placeholder molecules 227, but greater affinity for analytes 226. As a result, if the placeholder molecules 227 are competitively displaced by target analyte 226 from an added sample, the binding interaction between the capture surface region 215 and the particle 800 will be increased in strength. This may be detected by the microscopy apparatus 10 as a decrease in measured positional fluctuation of the particle 800 in capture surface region 215, as compared to capture surface region 214. If a capture surface region 214 has an affinity for a non-cross-reacting analyte, binding forces for sandwich structures in this capture surface region 214 will be unperturbed. As with the other assay embodiments, this process may be performed in a parallel manner on multiple particles (e.g. 3, 5, 10, 100 or more particles).

Analyte Specificity

Figure 22:
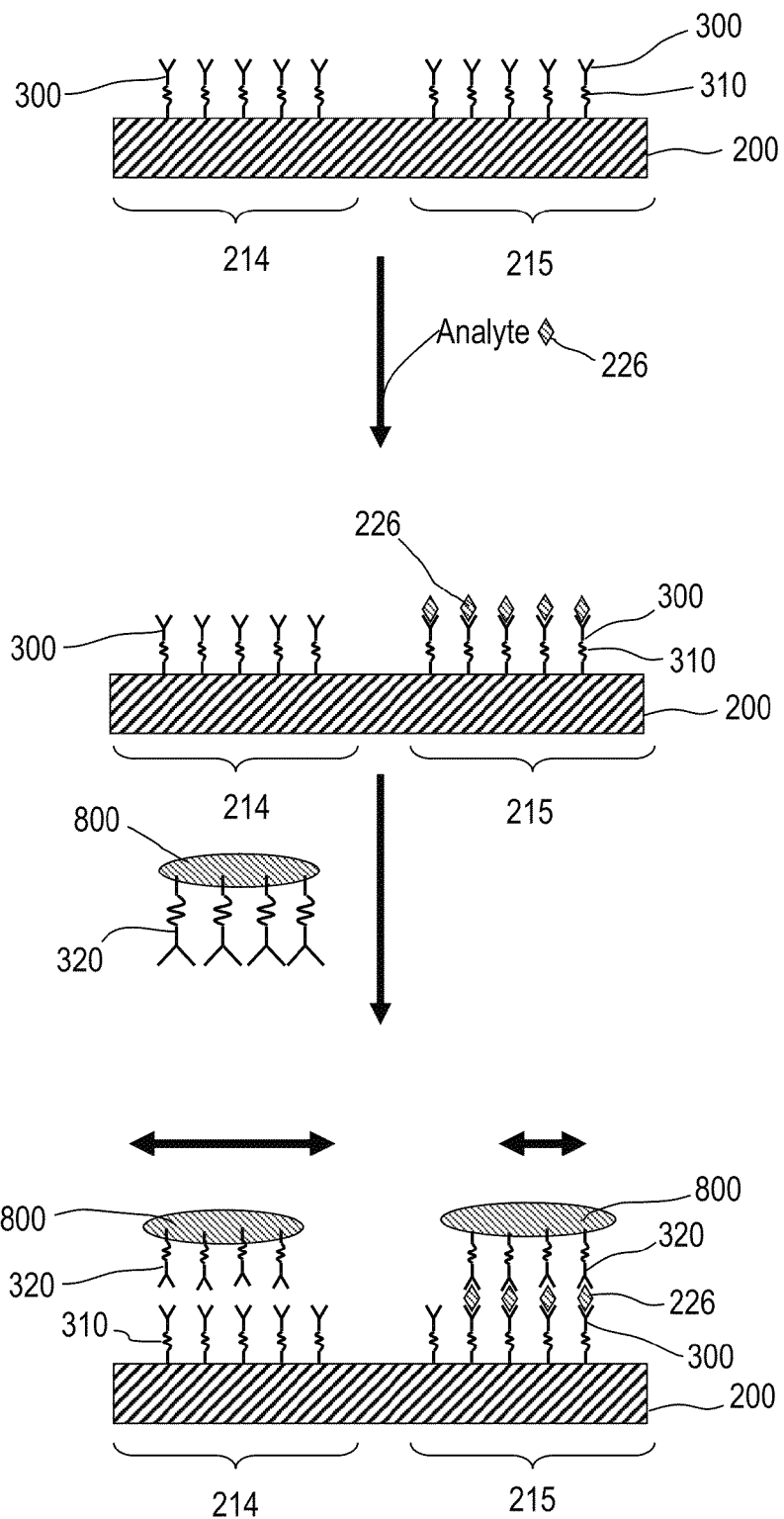
FIG. 22 is a cross-section which shows a sandwich assay along the lines of FIG. 21, where the capture surface regions have specificities for different analytes, according to one embodiment consistent with the present invention.

FIG. 22 shows a sandwich assay along the lines discussed above with respect to competitive assays. The capture surface regions 214, 215 of substrate 200 have specificities for different analytes, with capture surface region 215 having a specific affinity for analyte 226 and capture surface region 214 having a specificity for a different analyte.

A liquid containing analyte 226 is dispensed into the chamber 118 and onto the capture surface regions 214, 215. Given the right conditions (i.e., incubation, etc.), the analytes 226 bind to the probes 300 in capture surface region 215. A reporting particle 800 bearing probes 320, having specific affinity for analyte 226 is added. The reporting particle 800 will also have affinity for the analyte complementary to capture surface region 214, or else another particle with such affinity will also be included. After settling by gravity, centrifugal, or other means, the positional fluctuation of particle 800 is determined using the microscopy apparatus 10. A small mobility of particle 800 in capture surface region 215 is indicative of binding, and the presence of analyte 226 in a sandwich structure. If there is a relatively larger mobility of particle 800, as in capture surface region 214, then there are no binding reactions.

Covalent Tethers

Although FIG. 20 illustrates the use of non-covalent tethers, the use of covalent tethers may also be possible. For example, a nucleic acid oligo extension and ligation assay may be used to covalently link specifically-formed tethers. Other enzymatic, chemical or photochemical linking mechanisms that are known in the art may also be employed.

Screening Molecule Libraries

In this embodiment, the assay of FIGS. 18A-18B, for example, is used to screen a library of molecules. A library of molecules is generated, often using combinatorial chemistry approaches (i.e., for ligands), or with other methods such as buying a library of substances. Thus, the library may contain small-molecules (e.g., potential drug leads), biomolecules, or conjugates of potential ligands with encoding information (e.g. DNA-coded small molecule libraries on beads or yeast-display libraries of antibodies).

The library of molecules could be used in a spatially-resolved manner, in which case the location (such as the patch or capture surface region 210 etc. on the substrate 200, or the particular well of a well-plate or microfluidic cartridge) reveals which substance gave rise to a positive signal.

In one embodiment, the library of substances is bound to particles and then the particles are mixed together. Thus, there would be a large number of particles where each particle is coated with a single compound taken from a library of many thousands of compounds. The particles are mixed together in order such that it is possible to perform a single experiment on thousands of compounds at once, rather than thousands of experiments on a single compound.

At the end of the experiment, in order to identify which substance(s) gave rise to binding (or, in some cases, prevented binding), the following steps are taken:

(a) measuring the particles which are bound (or unbound), using the apparatus and methods of the present invention (i.e., determining binding of the particles using a microscopy apparatus 10);

(b) extracting those particles of interest (i.e., which are coated with the substance of interest), using known techniques such as micropipettes, magnetic manipulation of beads, or optical trapping systems; and (c) determining the nature of the substance which coats the particle (i.e., by sequencing it if it is DNA, or by other known methods), to determine which substance or substances gave the desired response.

The particles having desirable properties may be further characterized, amplified, or used for other testing. Thus, molecules may be identified which have a given specificity for diagnostic testing or for drug development, for example.

Washing Step

Because of the variations in positional freedom and resulting measurable positional fluctuation of the positive and negative particles, these may be discriminated without the need for a washing step. Thus, in general, assays performed using the apparatus and methods of the present invention, do not require a washing step (exceptions are noted above where a washing step is part of the process which precedes the introduction of probe particles).

Washing steps can disrupt the specific binding of analytes to the target, or of probes to the analytes. Although in conventional techniques, unbound portions of labels are washed away, since in the present invention, the labels are attached to larger particles which fall to the surface and are visible, there is no requirement for a washing step in these embodiments.

Alternately, less stringent washing may be employed than for conventional assays. The adhered particles may be washed, as in a conventional immunoassay, to eliminate spuriously retained particles. In this case, the washing may be gentler than would be required for a conventional immunoassay because bound and unbound particles may be discriminated based on the measurements of positional fluctuation described herein. As a result, assay data may be of higher quality (e.g., higher sensitivity or dynamic range) than would be achieved using the conventional techniques. As a result, a greater signal and/or dynamic range may be achieved.

Sensing Array Identified (I.D.).

The sensing array 200 or other substrate used with the methods described above, may include a machine readable identifier 205 such as a bar code or radio-frequency identification (RFID) tag (see FIG. 3). The identifier 205 may contain a unique identifier (e.g., a serial number). The identifier 205 may be used to look up (e.g., from a compact disc, the internet, etc.) information regarding the source of the chip, lot number, the specificity of the capture surface region 210, 211, etc., on the sensing array 200, calibration data, or other quality control data, machine operation or analysis protocols. The identifier 205 may be associated with the final assay results and a patient identifier in a medical records system. Some such data may also be directly encoded on the identifier 205. The identifier 205 may also be used with other embodiments of the present invention including those described herein, for assaying molecules in solution. The identifier 205 may also include information that allows customized operation of an automated microscopy system 10, for example. For example, the identifier 205 may contain coordinates of the capture surface regions 210, 211, 212 on the sensing array 200, calibration data, suggested illumination intensity, or the like.

As noted above, the sensing array 200 may be prepared using various techniques known in the art. For example, a glass microscope slide 200 (see FIG. 3, for example) may be cleaned and silanized with a functionalized linker 310 capable of binding the probe or probe complex (i.e., 220), as is well known in the art. (See also, "*Immobilized Biomolecules in Analysis: A Practical Approach*" by Toney Cass and Frances Ligler, Oxford University Press, 1998, as well as various, publications in the field of microarrays, biochips, and protein arrays including U.S. Patent Publication 2005/0048219, the contents of which are incorporated by reference in its entirety.)

Control Capture Surface Regions

In another embodiment consistent with the present invention, capture surface region 210, 211, 212 with multiple immobilized monoclonal antibodies may be used to detect one of two, or more types of cells, in which case, at least one further analysis step will be needed to resolve the cell type, if desired. In general, control and dummy/blank capture surface regions 210, 211, 212 and particles may also be included for quality control.

Particle Size

The size of the particles 800 (see FIG. 21, for example) may be chosen to enhance analysis of positional freedom. The number of potential binding sites is proportional to the cross-sectional area of the particle, and scales with $r^2$ for discs (e.g., RBCs), and linear for spherical particles. As a result, for smaller particles 800, a greater number of particles 800 may need to be examined. Using too small of a particle 800 (for a given particle density) may slow settling, while movement of the particle 800 along the surface is reduced. A sufficient particle size and density also prevents diffusion away from the substrate 200, which may simplify the analysis of positional freedom. Thus, the embodiments of the invention disclosed here may have the feature of using a particle size that is sufficient to achieve rapid settling, while possessing sufficient mobility for fast and accurate analysis.

Tether Length

In one embodiment consistent with the present invention, the position of a particle 800 may be measured in relation to a fiduciary reference (not shown). The reference may be associated with the substrate 200 or with the optics of an analyzing microscope.

In another embodiment consistent with the present invention, the particle motion used to determine positional freedom may be much larger that the length of the tethers 400. For example, the tethers 400 may be on the order of 10 nm in length (ranging between 2 nm to 50 nm, for example), with detected motion on the order of 100 nm or more.

In yet another embodiment consistent with the present invention, the detection of positional freedom includes estimating the length of the tether 400 and determining whether a cell 220 or particle 800 travels a distance that is greater than the tether length. The recorded data from the microscopy apparatus 10, may be filtered by the computer program to exclude travel of less than such a predetermined threshold distance. For example, such travel may be recorded as an "event" in the database. Multiple such events (e.g., 100-10,000 events) may be recorded in the database and analyzed by the computer program to obtain a statistically satisfactory measurement. Depending on the tether length and threshold value, a statistically satisfactory data set may be obtained by the computer program, by observing the particle for between 1 and 30 seconds.

Reference Value

In another embodiment consistent with the present invention, a particle (e.g., RBC 220, particle 800) that is adhered to a capture surface region 210, etc., is determined to have the specific binding target of the capture surface region 210 present on its surface if it fails to move greater than a predetermined certain distance after a predetermined certain amount of time, or predetermined certain number of observations.

Also, as stated above, the particle fluctuation measured by the microscopy apparatus 10 may be compared to a predetermined reference value (i.e., statistically determined from many calibration runs on control samples) to determine whether it likely corresponds to a bound or an unbound particle. In another embodiment, the collection of fluctuation measurements can be compared to the collection of fluctuation measurements from reference samples of known character.

Experimental Examples

The following examples are directed to blood typing (discussed further herein).

Figure 12:
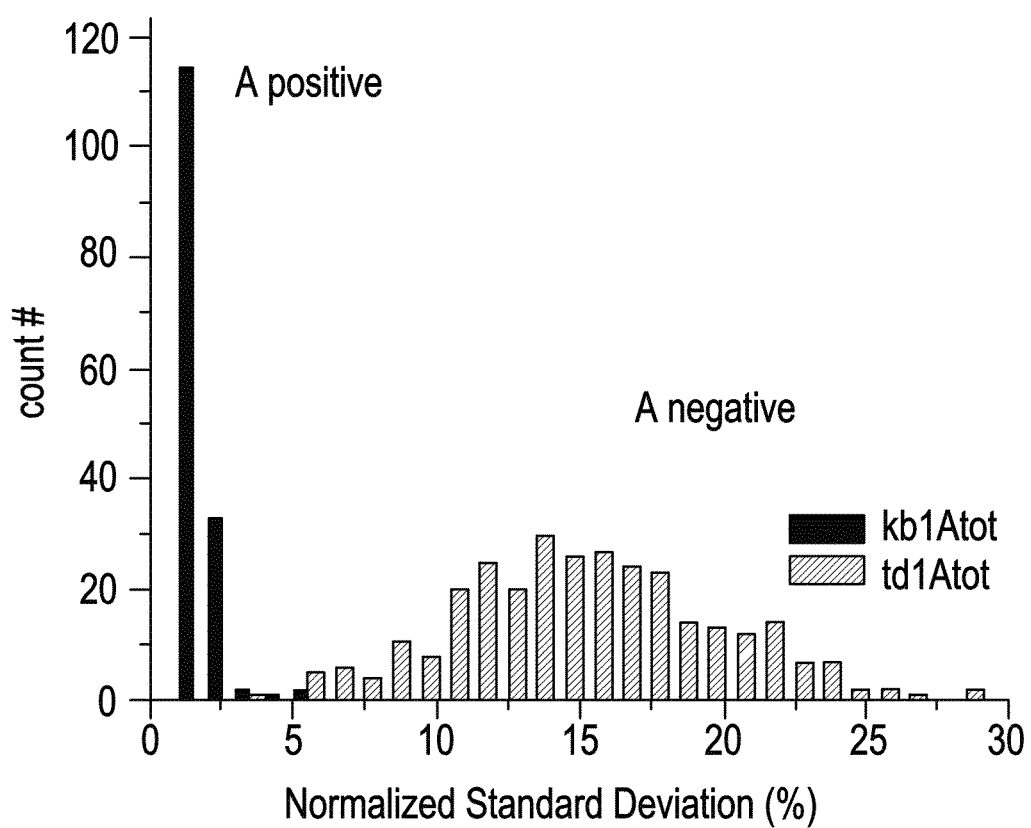
FIG. 12 shows plots of normalized standard deviation histograms, which measures the positional freedom of two different red blood cell samples (cells which are positive for the A antigen and cells which are negative for the A antigen) measured on an anti-A coated surface, according to one embodiment consistent with the present invention.

FIG. 12 shows plots of normalized standard deviation ("NSD") (which measures positional freedom) histograms of two different samples measured on an anti-A antibody coated surface. The black histogram is from measurements of red blood cells that are positive for the A antigen (i.e., A type). These cells were dispersed on a surface with immobilized anti-A antibody. The red histogram is from measurements of red blood cells that are negative for the A antigen (i.e., B type or A negative). These cells were dispersed on another surface with immobilized anti-A antibody. The NSD of each cell is plotted, indicating the magnitude of the intensity fluctuations each cell generated while it was on the surface, reflecting the amount of movement of the cell on the surface.

The B-type cells (red histogram) demonstrate high normalized standard deviation values, indicating the cells were free to diffuse and confirming the lack of any immobilizing interaction between the B type antigens on the red blood cell surface and the anti-A antibody attached to the solid substrate (i.e., coverslip). The A type cells (black histogram) demonstrate a narrow distribution of low normalized standard deviation values, indicating that these cells were immobilized due to the presence of specific bonds formed between the A type antigens on the red blood cell surface and the anti A antibody attached to the solid substrate. These plots clearly show the capability to distinguish specifically bound red blood cells (i.e., due to A-antigen/anti-A antibody bond formation) from non-bound cells using the NSD measurement protocol. Thus, these plots also show the capability of embodiments of the invention to forward-type red blood cells for the presence of A-antigen.

In this example, measurements were taken 10-20 minutes after the cells were dispersed into the sample chambers and data was acquired for approximately 10 seconds yielding a statistical image of pixel intensity fluctuations (i.e., normalized standard deviation image) calculated from 60 frames.

Figure 13:
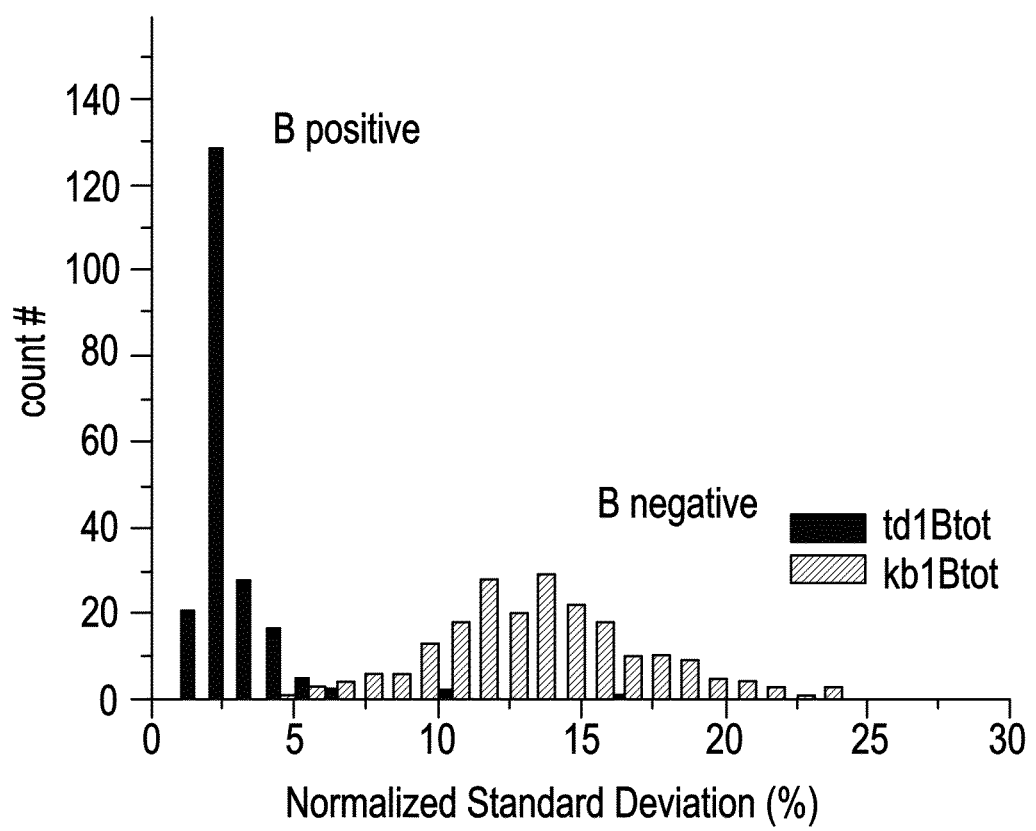
FIG. 13 shows plots of NSD histograms of two different red blood cell samples, one sample which is positive for the B antigen and one which is negative for the B antigen, measured on an anti-B coated substrate surface, according to one embodiment consistent with the present invention.

FIG. 13 shows plots of NSD histograms of two different samples, in this instance, of one of A type blood (red histogram) and the other of B type blood (black histogram), measured on an anti-B antibody coated substrate surface. The red histogram is from measurements of red blood cells that are negative for the B antigen (i.e., A type or B negative). These cells were dispersed on another surface with immobilized anti-B antibody. The NSD of each cell is plotted, indicating the magnitude of the intensity fluctuations each cell generated while it was on the surface, reflecting the amount of movement of the cell on the surface.

The A-type cells (red histogram) demonstrate high NSD values, indicating the cells were free to diffuse and confirming the lack of any immobilizing interaction between the A type antigens on the red blood cell surface and the anti-B attached to the solid substrate (i.e. coverslip). On the other hand, the B-type cells (black histogram) demonstrate a narrow distribution of low NSD values, indicating that these cells were immobilized due to the presence of specific bonds formed between the B-type antigens on the red blood cell surface and the anti-B attached to the solid substrate. These plots clearly show the capability to distinguish specifically bound red blood cells (i.e. due to B-antigen/anti-B bond formation) from non-bound cells using the NSD measurement protocol. Thus, this data demonstrates the capability of embodiments of the invention in forward-type red blood cells for the presence of B-antigen.

In this example, measurements were taken 10-20 minutes after the cells were dispersed into sample chambers and data was acquired for approximately 10 seconds yielding a statistical image of pixel intensity fluctuations (i.e. normalized standard deviation image) calculated from 60 frames.

Figure 14:
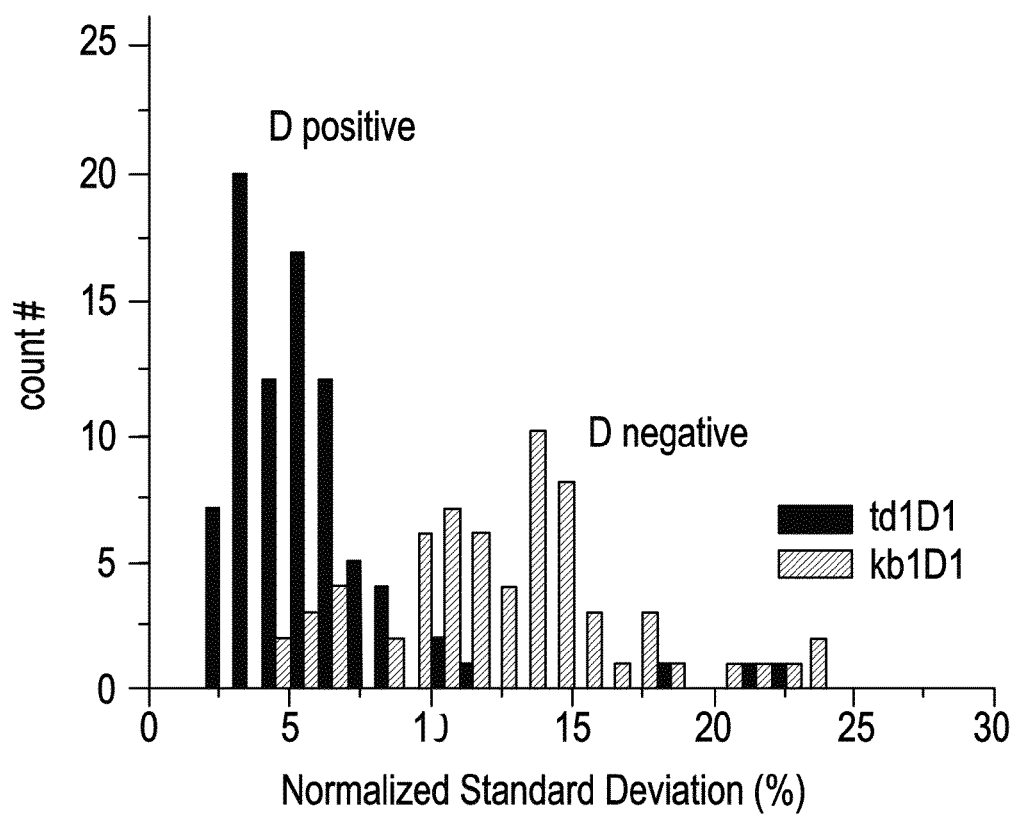
FIG. 14 shows plots of NSD histograms of two different red blood cell samples: one sample where the blood cells are negative for the D antigen and another where the D antigen is present on the cells, measured on an anti-D coated substrate surface, according to one embodiment consistent with the present invention.

FIG. 14 shows plots of NSD histograms of two different samples: one of D negative blood (red histogram) and the other of D positive blood (black histogram) measured on an antiD coated substrate surface. Each type of red blood cell was dispersed on a separate surface with immobilized anti-D antibody. The NSD of each cell is plotted, indicating the magnitude of the intensity fluctuations each cell generated while it was on the surface and, therefore, reflecting the amount of movement of the cell on the surface.

The D-negative type cells (red histogram) demonstrate high normalized standard deviation values, indicating the cells were free on the whole free to diffuse and confirming the lack of any dominant immobilizing interaction between the antigens on the red blood cell surface and the anti-D antibody attached to the solid substrate (i.e., coverslip). The D positive type cells (black histogram) demonstrate a lower NSD values, indicating that more of these cells were immobilized due to the presence of specific bonds formed between the D positive type antigens on the red blood cell surface and the anti-D antibody attached to the solid substrate. These distributions do show some overlap, although the means of each distribution are still distinctly different. Nonetheless, the plots clearly show the capability to distinguish the largely specifically bound group of red blood cells (i.e., due to D-antigen/anti-D antibody bond formation) from the largely non-specifically bound group of cells using the NSD measurement protocol. Thus, the data demonstrate the capability of embodiments of the invention to forward type a collection of red blood cells for the presence of D-antigen.

In this example, measurements were taken 10-20 minutes after the cells were dispersed into the sample chambers and data was acquired for approximately 10 seconds yielding a statistical image of pixel intensity fluctuations (i.e., normalized standard deviation image) calculated from 60 frames.

Figure 15:
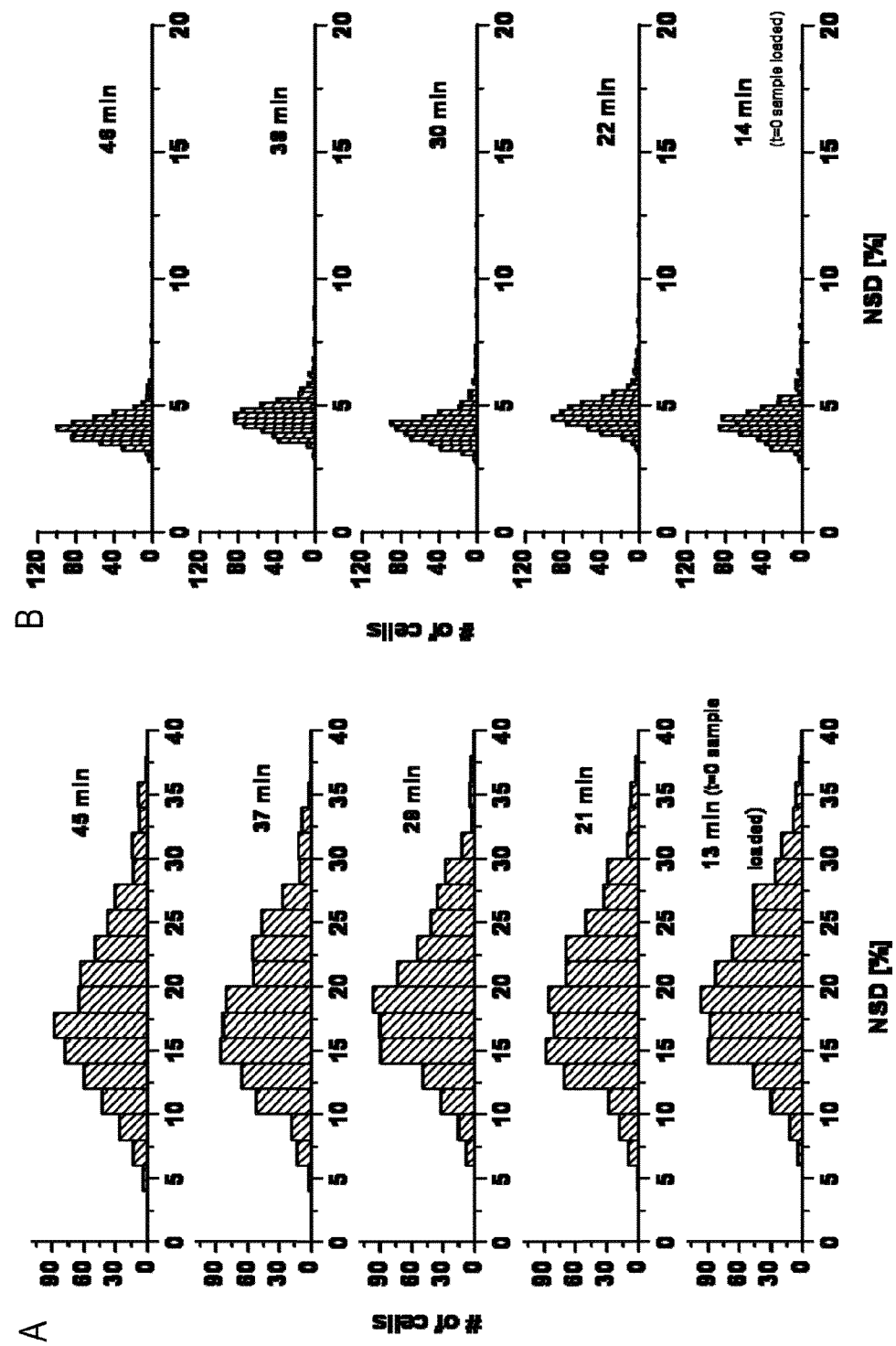
FIG. 15A shows a series of NSD histograms for a sample of red blood cells dispersed over a surface prepared with the B antigen, in the presence of anti-A, taken at different times, according to one embodiment consistent with the present invention.
FIG. 15B shows a time series of histograms under similar conditions to those in FIG. 15A, except that the surface has type-A antigens on it, according to one embodiment consistent with the present invention.

FIG. 15A shows a series of NSD histograms for a sample of red blood cells, taken at different times. The sample consists of type-A red blood cells in the presence of a high concentration of anti-A IgM class antibody (100 nM) in synthetic plasma onto a surface with B antigens on a glass coverslip surface. The B antigen surface was prepared by coating a glass coverslip with lysed type B red blood cells. This measurement configuration is similar to a reverse blood typing method wherein the plasma of a subject is tested for the presence or absence of naturally occurring antibodies by detecting the extent of binding between blood cells of known type on surfaces of known antigen type. The presence of binding in reverse methods indicates the presence of antibodies that are able to simultaneously bind the blood cells and the surface, thereby immobilizing them (i.e., reducing their positional fluctuations).

The bottom histogram in FIG. 15A was measured 13 minutes after type A cells dispersed in synthetic plasma with 100 nM anti-A antibody was introduced onto a surface with B antigens. Each histogram was generated by an analysis (cellular NSD calculation) of a sequence of 40 image frames acquired at a rate of 5 frames per second. The cells are able to diffuse, as evidenced by the high average values of observable NSD. The cells show similar diffusive behavior at later times as well, as may be seen by the similarity of the histograms measured at the 21, 29, 37 and 45 minute time marks.

FIG. 15B shows a time series of histograms under similar conditions to those in FIG. 15A, except that the surface was prepared to have type-A antigens on it (unlike the type-B antigen surface measurements of FIG. 15A) by preparing it with lysed type-A red blood cells. A high concentration of anti-A antibody (100 nM) was chosen to ensure that A cells were bound to the type-A surface (as was visually confirmed).

The first measured histogram (bottom histogram), taken 14 minutes after the cells were introduced onto the surface, shows that the cells are immobilized (low average NSD and narrow width). At later times the cells remain bound as well, as seen by the similar NSD histograms at the 22, 30, 38 and 46 minute measurements. Comparison of the histograms of FIGS. 15A and 15B allows us to choose a threshold value for NSD to determine whether a cell is bound or not. A threshold value of 7% NSD under these conditions is appropriate, with a majority of the cells in the unbound population of FIG. 15A being above this threshold, and the majority of cells in the bound population of FIG. 15B being below this threshold.

Figure 16:
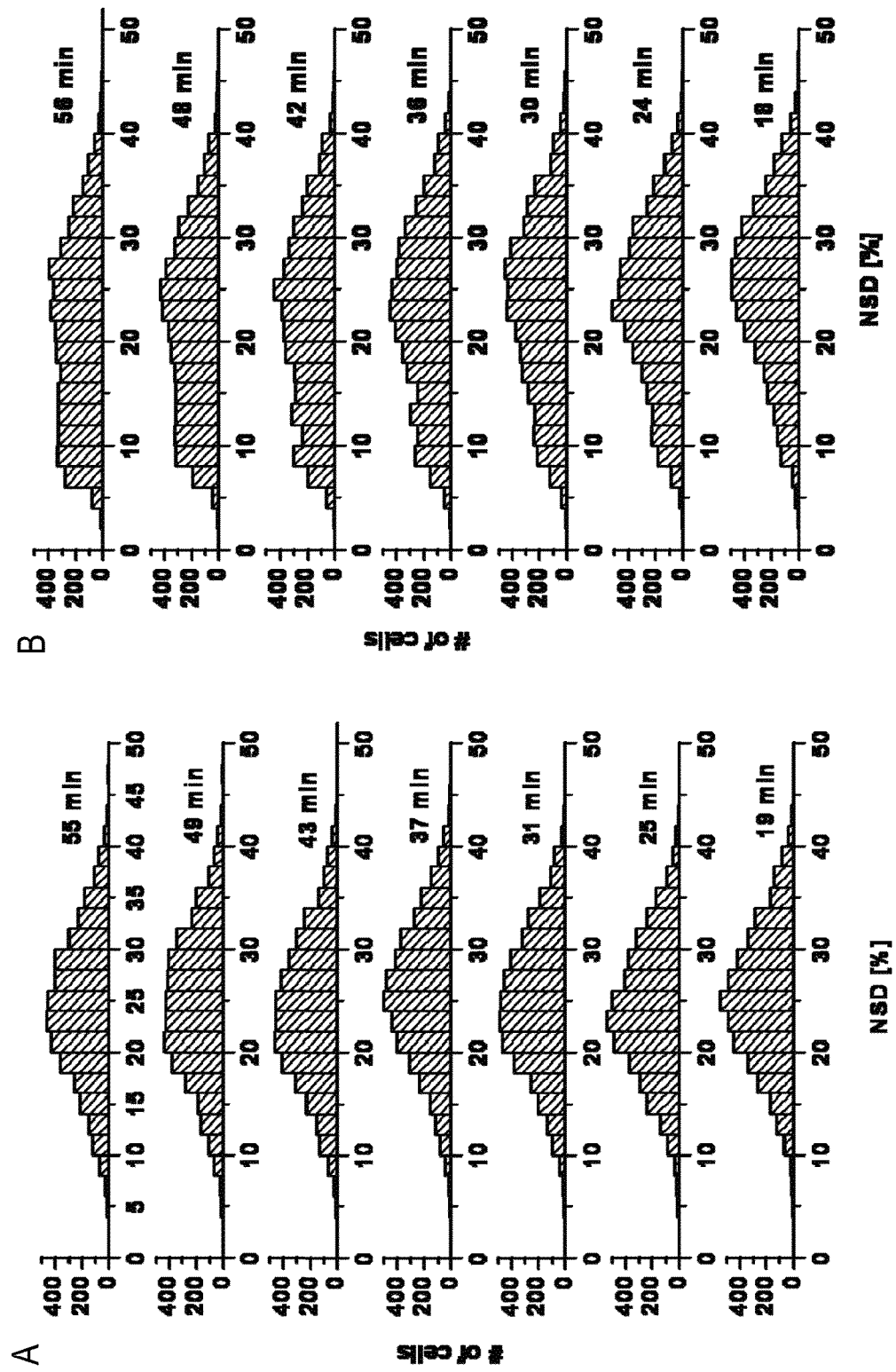
FIGS. 16A and 16B are histograms under conditions similar to the conditions measured in FIGS. 15A and 15B, except that a much lower concentration of antibody was used; according to one embodiment consistent with the present invention.

FIGS. 16A and 16B are similar to the conditions measured in FIGS. 15A and 15B except that a much lower concentration of antibody was used; only 1 nM of anti-A antibody was present in the synthetic plasma. In FIG. 16A, the NSD measurement protocol indicates that the A-type cells in synthetic plasma containing 1 nM anti-A antibody dispersed on the B-type surface are mostly unbound when first measured at 19 minutes after the sample was introduced onto the surface. Subsequent measurements at the 25, 31, 37, 43, 49, and 55 minute mark show similar behavior.

In FIG. 16B, the A-type cells in synthetic plasma containing 1 nM anti-A antibody were measured after being introduced onto a surface with A-type antigens. After 18 minutes, a slightly higher fraction of cells with low NSD values can be detected over the control set of cells (i.e., unbound cells) measured in FIG. 16A. With time, this low NSD fraction increases in magnitude, as can be seen by the progressive leftward shift in the histograms. The low 1 nM concentration of anti-A decreases the rate at which bonds between the cells and the surface are made, in comparison to the much faster binding interaction between the cells and the surface when 100 nM anti-A antibody was used (see FIG. 15B, where practically all cells were found to be bound within 14 minutes).

In summary, FIGS. 15A, 15B, 16A and 16B demonstrate that a range of antibody concentrations can be detected in a plasma solution using the red blood cells' NSD measurements on antigen coated surfaces.

Further embodiments of the present invention are based on the discovery that for at least some probe-types, nonspecific binding of settled particles occurs at a faster rate than specific binding. As a result, it has been discovered that one can measure a positional fluctuation signal based on early time points after settling of the particles. This early positional fluctuation may be subtracted from a positional fluctuation measurement based on later time points.

In other words, the computation of positional fluctuation may include a step in which the computer program operates to calculate a measure related to the time evolution of the particle position and optionally corrects for nonspecific binding that occurs with a greater kinetic time-constant than the time-constant for nonspecific binding. As noted above, this may be done through curve-fitting or other algorithms known in the arts of kinetic or molecular assay technology.

Thus, it should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A method of measuring a degree of binding between particles in a solution and a surface comprising:
    imaging a plurality of particles in a fluid in a sample holder using an image apparatus,
    wherein said sample holder includes a sample chamber having at least one capture surface region with which said particles interact;
    acquiring a time series of images of said plurality of particles using a camera; and
    measuring a positional freedom for at least some of said particles as a statistical measure which describes a time dependent positional evolution of each of said particles in a predetermined neighborhood surrounding each of said particles, said statistical measure being expressed as one of a variance, standard deviation, root mean square (RMS) travel, or autocorrelation function of a position of each of said particles, associated with said time series of images.

2. The method of claim 1, further comprising:
    suspending said plurality of particles in said fluid in said sample chamber under illumination from an illumination source of said imaging apparatus;
    wherein said sample holder is part of a flow device.

3. The method of claim 1, further comprising:
    applying an activating means to said particles in said fluid.

4. The method of claim 3, further comprising:
    moving said fluid in said sample chamber during measurement of said positional freedom, using said activating means.

5. The method of claim 1, further comprising:
    settling said particles in the sample chamber according to one of a gravity-based system, a centrifugal-based system, a flow-based system, a diffusion-based system, a magnetic-based system, or a holographic optical tweezing system.

6. The method of claim 1, wherein said at least one capture surface region binds probes that can form complexes with said particles.

7. The method of claim 1, further comprising:
    determining a positional freedom of each of said particles, using a processor, to determine a presence, absence or amount of an analyte.

8. The method of claim 1, wherein said imaging apparatus is an optical microscopy apparatus comprising a holographic imaging apparatus.

9. The method of claim 8, wherein said camera is from said optical microscopy apparatus; and said images are analyzed using a processor.

10. The method of claim 9, wherein said determination of said positional freedom is performed by measuring variations in light scattered from at least one of said particles in a predetermined neighborhood of said at least one capture surface region for a predetermined time, using said processor.

11. The method of claim 10, wherein said neighborhood of said at least one capture surface region is a predetermined boundary around a position of a known one of said particles where motion is observed.

12. The method of claim 10, wherein said positional freedom is determined by computing an average of multiple acquired images of said particles, computing an average difference between successive image frames of said particles, and computing a pixel-wise variation in intensity throughout said time series of said images, using said processor.

13. The method of claim 10, wherein an analysis of a statistical distribution of pixel intensity values is calculated, using said processor, for each of said particles, from which a distribution of positional freedom and a distribution of binding degrees of each of said particles, is obtained.

14. The method of claim 8, further comprising:
    automatically focusing on said capture surface region and finding one or more of said plurality of particles;
    selecting said one or more of said plurality of particles for analysis;
    obtaining said time series of images as a sequence of acquired images, of said plurality of particles using said camera; and
    determining said positional freedom of at least some of said plurality of particles using one of pattern recognition routines, size and shape data, absorbance data, fluorescence microscopy data, or other spectral data or other non-spectral measurements.

15. The method of claim 14, wherein a time elapsed between said acquired images and a length of said time series is determined by a computer, by particle type, imaging method, and particles being measured.

16. The method of claim 14, wherein said focusing includes:
    propagating out-of-focus images to different distances to allow a focus to be determined numerically.

17. The method of claim 16, further comprising:
    associating a focus measure with each of said numerically propagated images, to obtain an extremum in said focus measure, thereby allowing a single stage movement of said optical microscopy apparatus, to position said plurality of particles in a required focal position.

18. The method of claim 17, further comprising:
    acquiring said out-of-focus images upon which to perform numerical propagation calculations, using a focusing camera.

19. The method of claim 18, wherein said focusing camera is placed at an imaging plane different to that of said camera used for acquiring said sequence of images of said plurality of particles.

20. The method of claim 19, wherein focusing calculations are performed from images collected from said focusing camera which is positioned in said imaging plane that is out-of-focus compared to said camera used for acquiring said sequence of images of said plurality of particles.

21. The method of claim 18, wherein said focusing camera is the same as said camera used for acquiring said sequence of images of said plurality of particles; and
    wherein an image for focusing purposes is collected after controlled defocusing of an image of said plurality of particles.

22. The method of claim 18, further comprising:
    repeating the selection and determining steps with said propagating step, until a termination threshold is met, said termination threshold being met by one of a predetermined number of particles being analyzed in total, or a predetermined number of particles analyzed in each said capture surface region, an elapse of a maximum time period, or a surpassing of a statistical measure of error.

23. The method of claim 14, further comprising:
determining said positional freedom by computing a pixel-wise standard deviation of said sequence of images taken by said camera.

24. The method of claim 14, further comprising:
generating a sequence of intermediate images using said sequence of images acquired by said camera, which are computed as an absolute value of a pixel-wise difference in successive input images;
determining an output image by averaging said intermediate images; and
determining individual particle fluctuation values by averaging or summing values of said output image in said predetermined neighborhood of each of said plurality of particles.

25. The method of claim 14, further comprising:
determining individual particle fluctuation values by calculating a root-mean-squared value of inter-frame movement of said sequence of images.

26. The method of claim 25, wherein tracked positions of said plurality of particles over a plurality of frames are used to compute exact real-space interframe displacements of said plurality of particles over a plurality of frame intervals;
wherein particle displacements are averaged at each of said plurality of frame intervals to yield an average particle movement at each of said plurality of frame intervals.

27. The method of claim 26, wherein tracked positions are employed and average interframe displacements are computed and used to indicate an error condition in cases where said average interframe displacements achieve a predetermined high level, indicating a degree of unintended vibration or impact to said plurality of particles.

28. The method of claim 27, wherein said tracked positions are used in conjunction with said activation means to yield particle fluctuation values under controlled activation.

29. The method of claim 28, wherein said activation means includes one of a pneumatic or hydraulic pressure oscillator, a piezoelectric hydraulic actuator, a piezoelectric stage oscillator, a pneumatic or hydraulic valving or perturbation device, a thermal actuator, acoustic radiation, or well cap activation.

30. The method of claim 29, wherein said activation means achieves multiple forcing intervals, where forcing is uniform within a given interval; and
wherein said particle tracking identifies a given force by identifying a position of one of said plurality of particles during a given forcing interval.

31. The method of claim 8, wherein said imaging apparatus includes digital video microscopy, use of a quadrant photodiode, microscopy with coherent illumination, measurements of scattered light, holographic microscopy, and evanescent wave techniques.

32. The method of claim 1, further comprising:
computing a positional freedom distribution of said particles, using a processor.

33. The method of claim 32, further comprising:
incorporating a weighting effect into calculation of said positional freedom distribution.

34. The method of claim 1, wherein said particles are blood cells.

35. The method of claim 34, wherein said blood cells are red blood cells, and forward typing of said red blood cells is performed, wherein blood cells contain specific antigens which bind with capture surface regions containing specific antibodies.

36. The method of claim 34, wherein said blood cells are red blood cells, and reverse grouping of one of a plasma or serum sample is performed, wherein said red blood cells contain or lack specific blood group antigens which can bind with target antibodies which links to antigens of red blood cells disposed on said capture surface regions.

37. The method of claim 34, wherein said blood cells are flattened red blood cells.

38. The method of claim 1, wherein a presence or absence of an analyte on the surface or surrounding solution of at least one of said particles is measured.

39. The method of claim 38, wherein the method is used to screen antibodies.

40. The method of claim 1, wherein the method is used to screen for infectious disease.

41. The method of claim 1, wherein the method is used to screen a library of molecules.

42. The method of claim 1, wherein each of said plurality of particles that is adhered to said capture surface region, is determined to have a specific binding target of said capture surface region present on a surface thereon when each of said adhered plurality of particles fails to move greater than a predetermined distance after a predetermined amount of time or a predetermined number of observations.

43. The method of claim 42, further comprising:
measuring positional data of a time-series of observations in relation to a fiduciary marking of a first surface region of said sample holder, or a microscope stage, or of other particles or microscopic objects.

44. The method of claim 1, further comprising:
determining said measure of positional freedom for each of said particles individually, or for multiple particles.

45. The method of claim 44, wherein said measure of positional freedom is determined for multiple particles; and
wherein images of multiple particles are manipulated mathematically or computationally, which does not require identification of individual particles.

46. The method of claim 45, further comprising:
acquiring successive images of said multiple particles at two or more times using a camera, and using a digital comparison of said successive images to parameterize a time-dependent autocorrelation function or time-dependent probability function.

47. The method of claim 1, wherein an identity of said capture surface region is determined from one of machine-readable markers, or from knowledge of a fluidic cartridge orientation with respect to reference markings.

48. The method of claim 1, further comprising:
obtaining calibration data for one or more samples of said plurality of particles.

49. The method of claim 48, wherein two calibration samples are measured and a calibration threshold value of positional freedom measurement is obtained; and
wherein measurements of said positional freedom of said plurality of particles are compared to said calibration threshold, to determine a presence or absence of binding interactions.

* * * * *